United States Patent
Wnuk et al.

(10) Patent No.: US 10,954,178 B1
(45) Date of Patent: Mar. 23, 2021

(54) SYNTHESIS OF HALOINDENES

(71) Applicants: Stanislaw F. Wnuk, Miami, FL (US); Md Abu Hasan Howlader, Miami, FL (US)

(72) Inventors: Stanislaw F. Wnuk, Miami, FL (US); Md Abu Hasan Howlader, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 17/005,626

(22) Filed: Aug. 28, 2020

(51) Int. Cl.
  *C07C 17/357* (2006.01)
  *C07C 23/18* (2006.01)
(52) U.S. Cl.
  CPC ............ *C07C 17/357* (2013.01); *C07C 23/18* (2013.01); *C07C 2602/08* (2017.05)
(58) Field of Classification Search
  CPC .... C07C 23/18; C07C 2602/08; C07C 17/357
  See application file for complete search history.

(56) References Cited

PUBLICATIONS

Caputto, M., et al., "Thiosemicarbazones Derived From 1-Indanones as New Anti-Trypanosoma Cruzi Agents." Bioorganic & Medicinal Chemistry, 2011, 19: 6818-6826.
Duan, Y., et al., "Recyclable Hypervalent-Iodine-Mediated Dehydrogenative α, β'-Bifunctionalization of β-Keto Esters Under Metal-Free Conditions." Chemistry-A European Journal, 2015, 21(37): 13052-13057.
Duan, Y., et al., "Recyclable Hypervalent-Iodine-Mediated Dehydrogenative α, β'-Bifunctionalization of β-Keto Esters Under Metal-Free Conditions, Supporting Information." Chemistry-A European Journal, 2015, 21(37): S0-S80.
Guan, X., et al., "Design, Synthesis and Evaluation of Indene Derivatives as Retinoic Acid Receptor α Agonists." Molecules, 2017, 22(32): 1-16.
Miller, R.B., et al., "Synthesis of Isoquinolines from Indenes." The Journal of Organic Chemistry, 1980, 45: 5312-5315.

*Primary Examiner* — Jafar F Parsa
(74) *Attorney, Agent, or Firm* — Saliwanchik, Lloyd & Eisenschenk

(57) ABSTRACT

The subject invention provides an expedited synthesis of 5, 6, and 7-iodoindenes from the corresponding aminoindan-1-ones in more than 70% yield, employing readily available precursors and reagents. A three-step sequence involves diazotization-iodination of aminoindan-1-one followed by reduction and dehydration. The method has a general character and can be extended for the preparation of various 4-, 5-, 6- or 7-haloindenes using different halogen sources for diazotization-halogenation reaction.

16 Claims, 50 Drawing Sheets

Overall yield >70%

SYNTHESIS OF HALOINDENES

BACKGROUND OF THE INVENTION

The haloindenes are convenient precursors in organic and biologically-targeted syntheses. For example, 6-bromoindene is used to prepare ethylene-bis (indenyl) ligand via Suzuki coupling. The 4-, 5-, or 6-bromo (or chloro)indenes are utilized in the synthesis of inhibitors of the $Na^+/H^+$ exchanger and histone lysine specific demethylases. Moreover, 5- and 6-bromoindene are used to study the mechanism of dioxygenase-catalyzed benzylic hydroxylation of indene. The 6-chloroindene serves as precursor for the synthesis of 6-chloro-N-hydroxy-1H-indene-2-carboxamide, used to study the structure-activity relationships of neurotoxin A protease inhibitors, as well as fullerene-based photovoltaic acceptor materials. Haloindenes can also be used to synthesize halo-substituted isoquinoline derivatives. Indene molecule ($C_9H_8$) has received considerable attention from the combustion and physical (organic) chemistry communities as a potential building block of non-planar polycyclic aromatic hydrocarbons (PAHs) such as corannulene ($C_{20}H_{10}$)—a precursor to fullerenes such as $C_{60}$ and $C_{70}$. Different indenyl radicals can act as a precursor for the molecular mass growth process to form non-planner PAH.

Pyrolysis of bromoindenes produces resonance-stabilized and thermodynamically most stable 1-indenyl π radical which was found to be non-effective precursor for the molecular mass growth processes of PAH in extraterrestrial and combustion environments.

There is only one method for the preparation of more reactive 5- or 6-iodoindene, which requires expensive intermediates and several steps. The reported yields for 5- or 6-iodoindenes were only 20% and 7% (Miller, R. B.; Frincke, J. M. Synthesis of isoquinolines from indenes. *J. Org. Chem* 1980, 45, 5312). The 5-nitroindene and 6-nitroindene were used as precursors for such preparation, respectively.

Thus, there is a need for developing methods for synthesizing haloindenes, in particular, iodoindenes including 4-, 5-, 6-, and 7-iodoindenes isomers, with high yield and purity, which are simple and do not require the use of expensive and/or unstable reagents and/or intermediates.

BRIEF SUMMARY OF THE INVENTION

The subject invention provides methods for preparing various substituted indenes including haloindenes, for example, 4-, 5-, 6- or 7-haloindenes. The method comprises a diazotization-halogenation reaction using different halogen sources. In specific embodiments, the subject invention provides methods for synthesizing 4-, 5-, 6- or 7-chloroindenes, bromoindenes, fluoroinfenes and/or iodoindenes.

In one embodiment, the method for synthesizing a haloindene comprises or consists of: mixing a nitrite compound and one or more halogen sources with aminoindan-1-one to produce haloindanone; adding a reducing agent to said haloindanone to produce haloindanol; and adding an acid to said haloindanol to produce the haloindene.

In one embodiment, the aminoindan-1-one is selected from 4-, 5-, 6-, or 7-aminoindan-1-one. The nitrite compound may be, for example, t-BuONO and/or isoamyl nitrite. The halogen source may be one or more of, for example, $X_2$, $CuX_n$ (n=1 or 2), NXS, $CH_mX_o$ (m=1 or 2; o=1, 2 or 3), $NOBX_4$, KX and HX (wherein X=Cl, F, Br, or I). In a specific embodiment, halogen sources may be, for example, $CuCl_2$ for chlorination, $CHBr_3$ for bromination, $I_2$, CuI, $CH_2I_2$, KI and/or HI for iodination, and nitrosonium tetraborofluoride ($NOBF_4$) for fluorination to produce haloindan-1-ones. Preferably, the reducing agent is $NaBH_4$. The acid is preferably, HCl or $H_2SO_4$.

In preferred embodiments, the subject invention provides methods for expeditious synthesis of iodoindenes such as 5-, 6-, and 7-iodoindenes from the corresponding aminoindan-1-ones in more than 70% yield, employing readily available precursors and ubiquitous reagents. In a specific embodiment, the method according the subject invention comprises a three-step process involving diazotization-iodination of aminoindan-1-one followed by reduction and dehydration. The high-yielding method of the subject invention for the synthesis of iodoindenes can employ iodoindan-1-ones and/or aminoindan-1-ones as convenient precursors.

In one embodiment, the method for synthesizing an iodoindene comprises or consists of: mixing a nitrite compound and one or more iodine sources with aminoindan-1-one to produce iodoindanone; adding a reducing agent to said iodoindanone to produce iodoindanol; and adding an acid to dehydrate said iodoindanol.

In one embodiment, aminoindan-1-one is selected from 4-, 5-, 6-, or 7-aminoindan-1-one. The nitrite compound is, for example, t-BuONO or isoamyl nitrite. The iodine source may be one or more of, for example, $I_2$, CuI, $CH_2I_2$, KI, NIS and HI. Preferably, the reducing agent is $NaBH_4$, and the acid is HCl or $H_2SO_4$.

The method according to the subject invention allows preparing expensive 5-iodoindene and unreported 7-iodoindene in high yields utilizing readily available and cost-effective reagents. Advantageously, it avoids the use of expensive nitroindenes, and potentially explosive trifluoroperacetic acid. This represents a significant improvement in overall yield from indanone-1 or aminoindan-1-one. The method of the subject invention also avoids oxidation to 5-nitroindan-1-one with trifluoroperacetic acid and does not require reduction step to the unstable 6-aminoindene intermediate.

In one embodiment, the subject invention provides a method for synthesizing 5-iodoindene, the method comprising or consisting of: mixing 6-aminoindan-1-one with a nitrite compound and one or more iodine sources to produce 6-iodo-1-indanone; adding a reducing agent to said 6-iodo-1-indanone to produce 6-iodo-1-indanol; and adding an acid to dehydrate said 6-iodo-1-indanol to produce 5-iodoindene.

In one embodiment, the subject invention provides a method for synthesizing 6-iodoindene, the method comprising or consisting of: mixing 5-aminoindan-1-one with a nitrite compound and one or more iodine sources to produce 5-iodo-1-indanone; adding a reducing agent to said 5-iodo-1-indanone to produce 5-iodo-1-indanol; and adding an acid to said 5-iodo-1-indanol to produce 6-iodoindene.

In one embodiment, the subject invention provides a method for synthesizing 7-iodoindene, the method for synthesizing 7-iodoindene comprising: mixing a nitrite compound and one or more iodine sources with 4-aminoindan-1-one to produce 4-iodo-1-indanone; adding a reducing agent to said 4-iodo-1-indanone to produce 4-iodo-1-indanol; and adding an acid for dehydrating said 4-iodo-1-indanol to produce 7-iodoindene.

In a specific embodiment, the nitrite compound is t-BuONO. The iodine source comprises one or more of, for example, $I_2$, CuI, $CH_2I_2$, KI, HI, and NIS. Preferably, the iodine source is a mixture of $I_2$, CuI, and $CH_2I_2$, the reducing agent is $NaBH_4$, and the acid for dehydrating 5-iodo-1-indanol is HCl.

In preferred embodiments, the yield of iodoindenes by the methods of the subject invention is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99%. The yield of each intermediate product from each step of the methods according to the subject invention is also at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99%.

The iodoindenes synthesized according to the subject invention can serve as effective substrates for the regioselective Stille coupling with vinyl stannanes and for Sonogashira coupling with alkynes in the presence of triethylamine.

DETAILED DESCRIPTION OF THE INVENTION

Figure 1:
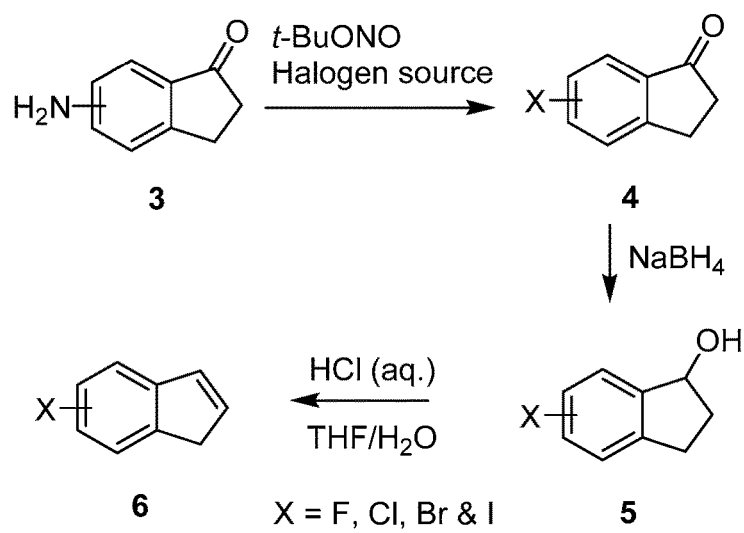
FIG. 1 shows the general scheme for the synthesis of haloindenes 6 from aminoindan-1-ones 3.

The subject invention provides methods for preparing various substituted indenes including haloindenes, for example, 4-, 5-, 6- or 7-haloindenes. The method comprises a diazotization-halogenation reaction using different halogen (X=Cl, F, Br, or I) sources. In specific embodiments, the subject invention provides methods for synthesizing 4-, 5-, 6- or 7-chloroindenes, bromoindenes, fluoroinfenes and/ or iodoindenes.

In one embodiment, the method for synthesizing a haloindene comprises or consists of:

optionally, a step of nitrating indan-1-one with a source compound for a nitro group, optionally, in the presence of an acid, to afford nitroindan-1-one;

optionally, a step of reducing nitroindan-1-one to aminoindan-1-one in the presence of a reducing agent;

a step of diazotizating and halogenating aminoindan-1-one to afford haloindanone in the presence of one or more halogen sources;

a step of reducing haloindanone to haloindanol with a second reducing agent; and a step of dehydrating haloindanol with a second acid.

In one embodiment, the step of nitrating indan-1-one comprises mixing indan-1-one with a source compound for a nitro group, optionally in the presence of an acid. Preferably, the source compound for a nitro group can be, for example, HNO$_3$, potassium nitrate, ammonium nitrate, and/ or sodium nitrate. The acid can be, for example, trifluoroacetic acid, trifluoroacetic anhydride, acetic anhydrides, acetic acid and sulfuric acid. In specific embodiments, the step of nitrating indan-1-one comprises mixing indan-1-one with a combination selected from, KNO$_3$/H$_2$SO$_4$, HNO$_3$/ HCl, HNO$_3$/H$_2$SO$_4$, HNO$_3$/HoAc, HNO$_3$/acetic anhydrides, HNO$_3$/trifluoroacetic anhydride, and ammonium nitrate/trifluoroacetic anhydride. The step of nitrating indan-1-one produces nitroindan-1-one, for example, 6-nitro- and/or 4-nitroindan-1-one with high yields.

In one embodiment, the method for synthesizing a haloindene comprises a step of reducing nitroindan-1-one to afford aminoindan-1-one, the step comprising adding a reducing agent to nitroindan-1-one. The reducing agent may be, for example, iron in an acidic media. Preferably, the acidic media is NH$_4$Cl. The acidic media may also be an acid such as hydrochloric acid, sulfuric acid, or acid known in the art. Optionally, the reducing reaction occurs in the presence of a solvent, such as EtOH, and/or MeOH.

In one embodiment, the reducing reaction may occur at an elevated temperature, for example, from about 50° C. to about 90° C., from about 55° C. to about 90° C., from about 60° C. to about 90° C., from about 65° C. to about 90° C., from about 70° C. to about 90° C., from about 75° C. to about 90° C., or from about 75° C. to about 85° C.

In one embodiment, the method for synthesizing a haloindene comprises a step of diazotization-halogenation of aminoindan-1-one to produce haloindanone, the step comprising mixing a nitrite compound, and one or more halogen sources, with aminoindan-1-one. The diazotization occurs in the presence of a nitrite compound, while the halogenation occurs in the presence of one or more halogen sources.

In one embodiment, the nitrite compound may be, for example, t-BuONO and/or isoamyl nitrite. The halogen source may be one or more of, for example, $X_2$, $CuX_n$ (n=1 or 2), NXS, $CH_mX_o$ (m=1 or 2; o=1 2, or 3), $NOBX_4$, KX and HX (wherein X=Cl, F, Br, or I).

The diazotization-halogenation may also occur in the presence of a solvent, such as THF. In a specific embodiment, halogen sources may be, for example, $CuCl_2$ for chlorination, $CHBr_3$ for bromination, and nitrosonium tetraborofluorate ($NOBF_4$) for fluorination to produce haloindan-1-ones.

In one embodiment, the diazotization-halogenation may occur at an elevated temperature, for example, from about 50° C. to about 90° C., from about 50° C. to about 85° C., from about 50° C. to about 80° C., from about 50° C. to about 75° C., from about 55° C. to about 75° C., from about 60° C. to about 75° C., or from about 60° C. to about 70° C.

In one embodiment, the method for synthesizing a haloindene comprises a step of reducing haloindanone to haloindanol, the step comprising adding a second reducing agent to haloindanone. The second reducing agent may be the same or different from the reducing agent in the step of reducing nitroindan-1-one to aminoindan-1-one. Preferably, the second reducing agent may be, for example, $NaBH_4$. Optionally, this step also occurs in the presence of a solvent e.g., EtOH, or a solvent mixture, e.g., THF/MeOH, and $EtOH/H_2O$.

In one embodiment, the method for synthesizing a haloindene comprises a step of dehydrating haloindanol, the step comprising adding a second acid to haloindanol. The second acid may be the same or different from the acid used in the step of nitration of indan-1-one and/or the step of diazotization-halogenation of aminoindan-1-one. Preferably, the second acid may be, for example, HCl. More preferably, the second acid is aqueous HCl in $THF/H_2O$.

In one embodiment, the subject invention provides methods for expeditiously synthesizing a haloindene comprising a three-step process (FIG. 1) involving diazotization-iodination of aminoindan-1-one followed by reduction and dehydration. Specifically, the method comprises or consists of: diazotizing and iodinating aminoindan-1-one to produce haloindanone in the presence of one or more halogen sources; reducing haloindanone to haloindanol with a reducing agent; and dehydrating haloindanol with an acid.

In one embodiment, the method for synthesizing a haloindene comprises or consists of: providing a precursor, the precursor being aminoindan-1-one; mixing a nitrite compound, and one or more halogen sources with aminoindan-1-one for diazotization and iodination to produce haloindanone; adding a reducing agent for reducing haloindanone to produce haloindanol; and adding an acid for dehydrating haloindanol.

In one embodiment, the method for synthesizing one or more haloindenes comprises or consists of:

a step of nitrating indan-1-one with a source compound for a nitro group, optionally, in the presence of an acid, to afford nitroindan-1-one;

a step of reducing nitroindan-1-one to aminoindan-1-one in the presence of a reducing agent;

a step of diazotizating and halogenating aminoindan-1-one to afford haloindanone in the presence of a nitrite compound and one or more halogen sources;

a step of reducing haloindanone to haloindanol with a second reducing agent; and a step of dehydrating haloindanol with a second acid.

In one embodiment, the method for synthesizing one or more haloindenes further comprises one or more steps of separating different indene isomers from a mixture of products after each step of the method.

In one embodiment, the haloindenes include chloroindenes, bromoindenes, fluoroinfenes and iodoindenes. Preferably, the haloindenes are selected from 4-, 5-, 6-, and 7-chloroindenes, bromoindenes, fluoroinfenes and iodoindenes. The subject invention also provides methods for synthesizing chloroindenes, bromoindenes, fluoroinfenes and/or iodoindenes with high yields. The high-yielding methods of the subject invention for the synthesis of haloindenes can employ iodoindan-1-ones or aminoindan-1-one as convenient precursors.

In one embodiment, the yield of haloindenes by the methods of the subject invention is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99%. The yield of each intermediate product from each step of the methods for synthesizing haloindenes is also at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99%.

In one embodiment, the subject invention provides a method for synthesizing an iodoindene comprising or consisting of:

optionally, a step of nitrating indan-1-one with a source compound for a nitro group, optionally, in the presence of an acid, to afford nitroindan-1-one;

optionally, a step of reducing nitroindan-1-one to aminoindan-1-one in the presence of a reducing agent;

a step of diazotizating and iodinating aminoindan-1-one to produce iodoindanone in the presence of a nitrite compound and one or more iodine sources;

a step of reducing iodoindanone to iodoindanol with a second reducing agent; and dehydrating iodoindanol with a second acid.

In one embodiment, the method for synthesizing an iodoindene comprises a step of nitrating indan-1-one, the step comprising mixing indan-1-one with a source compound for a nitro group, optionally, in the presence of an acid. Preferably, the source compound for the nitro group can be, for example, $HNO_3$, potassium nitrate, ammonium nitrate, and/or sodium nitrate. The acid can be, for example, trifluoroacetic acid, trifluoroacetic anhydride, acetic anhydrides, acetic acid and sulfuric acid. In specific embodiments, the step of nitrating indan-1-one comprises mixing indan-1-one with a combination selected from, $KNO_3/H_2SO_4$, $HNO_3/HCl$, $HNO_3/H_2SO_4$, $HNO_3/HoAc$, $HNO_3/$ acetic anhydrides, $HNO_3$/trifluoroacetic anhydride, and ammonium nitrate/trifluoroacetic anhydride. The step of nitration of indan-1-one affords nitroindan-1-one, for example, 6-nitro- and 4-nitroindan-1-one with a high yield.

In one embodiment, the method for synthesizing an iodoindene comprises a step of reducing nitroindan-1-one to afford aminoindan-1-one, the step comprising adding a reducing agent to nitroindan-1-one. The reducing agent may be, for example, iron in an acidic media. Preferably, the reducing agent comprises iron powder in $NH_4Cl$. The acidic media may also be an acid such as hydrochloric acid, sulfuric acid or acid disclosed above. Optionally, the reducing reaction occurs in the presence of a solvent such as EtOH, and/or MeOH. The reducing reaction may occur at an elevated temperature.

In one embodiment, the method for synthesizing an iodoindene comprises a step of diazotizating and iodinating aminoindan-1-one to produce iodoindanone, the step comprising mixing a nitrite compound and one or more iodine sources with aminoindan-1-one. The diazotization occurs in the presence of a nitrite compound, such as t-BuONO or isoamyl nitrite. The iodine source may be one or more of, for example, $I_2$, CuI, $CH_2I_2$, KI, HI, and NIS. Preferably, the iodine source comprises a mixture of iodine compounds selected from $I_2$, CuI, $CH_2I_2$, KI, HI, and NIS. More preferably, the iodine source comprises a mixture of $I_2$, CuI, and $CH_2I_2$. The diazotization-iodination may also occur in the presence of a solvent, such as THF. The diazotization-iodination may occur at an elevated or lower temperature.

In one embodiment, the method for synthesizing an iodoindene comprises a step of reducing iodoindanone to iodoindanol, the step comprising adding a second reducing agent to iodoindanone. The second reducing agent may be the same or different from the reducing agent in the step of reducing nitroindan-1-one to aminoindan-1-one. Preferably, the second reducing agent may be, for example, $NaBH_4$. Optionally, this step also occurs in the presence of a solvent, e.g., EtOH, or a solvent mixture, e.g., THF/MeOH, and EtOH/$H_2O$.

In one embodiment, the method for synthesizing an iodoindene comprises a step of dehydrating iodoindanol, the step comprising adding a second acid to iodoindanol. The second acid may be the same or different from the acid used in the step of nitration of indan-1-one and/or the step of diazotization-iodination of aminoindan-1-one. Preferably, the second acid may be, for example, HCl. More preferably, the second acid is aqueous HCl in THF/$H_2O$.

Figure 2:
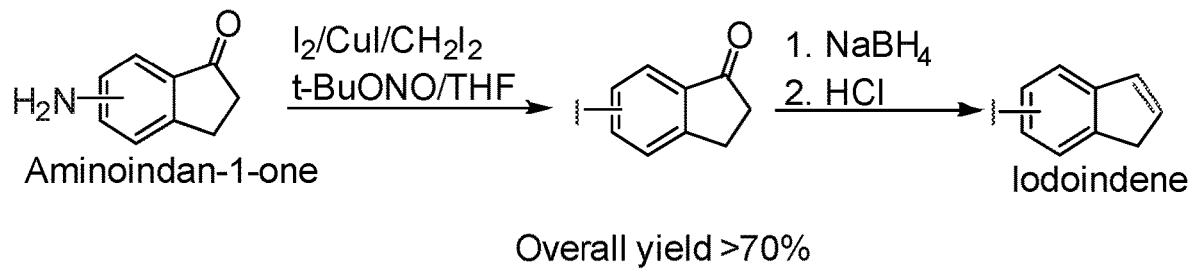
FIG. 2 shows the general scheme for synthesizing iodoindenes from aminoindan-1-one.

In certain embodiments, the subject invention provides methods for expeditious synthesis of iodoindene, e.g., 4-, 5-, 6-, and 7-iodoindenes from the corresponding aminoindan-1-ones in more than 70% yield, employing readily available precursors and reagents. In a specific embodiment, the method according to the subject invention comprises a three-step process (FIG. 2) involving diazotization-iodination of aminoindan-1-one followed by reduction and dehydration.

In one embodiment, the method for expeditious synthesizing an iodoindene comprises or consists of: providing a precursor, the precursor being aminoindan-1-one; mixing a nitrite compound, and one or more iodine sources with aminoindan-1-one for diazotization and iodination to produce iodoindanone; adding a reducing agent for reducing iodoindanone to produce iodoindanol; and adding an acid for dehydrating iodoindanol.

In specific embodiments, the iodoindene is selected from 4-, 5-, 6-, and 7-iodoindenes. The one or more iodine sources are selected from $I_2$, CuI, $CH_2I_2$, KI, NIS and HI. The reducing agent is $NaBH_4$. The acid is HCl. The nitrite compound is t-BuONO or isoamyl nitrite. Aminoindan-1-one is selected from 4-, 5-, 6-, or 7-aminoindan-1-one.

In one embodiment, the subject invention provides straightforward methods for synthesizing 5-, 6-, and 7-iodoindenes isomers from 6-, 5-, and 4-aminoindanones.

In one embodiment, the subject invention provides a method for synthesizing 5-iodoindene, the method comprising or consisting of:

optionally, mixing indan-1-one with a source compound for a nitro group, optionally, in the presence of an acid, to produce 6-nitroindan-1-one;

optionally, adding a reducing agent to 6-nitroindan-1-one to produce 6-aminoindan-1-one;

mixing 6-aminoindan-1-one with a nitrite compound and one or more iodine sources to produce 6-iodo-1-indanone;

adding a second reducing agent to 6-iodo-1-indanone to produce 6-iodo-1-indanol; and adding a second acid to dehydrate 6-iodo-1-indanol to produce 5-iodoindene.

In one embodiment, the subject invention provides a method for synthesizing 7-iodoindene, the method comprising or consisting of:

optionally, mixing indan-1-one with a source compound for a nitro group, optionally, in the presence of an acid, to produce 4-nitroindan-1-one;

optionally, adding a reducing agent to 4-nitroindan-1-one to produce 4-aminoindan-1-one;

mixing 4-aminoindan-1-one with a nitrite compound and one or more iodine sources to produce 4-iodo-1-indanone;

adding a second reducing agent to 4-iodo-1-indanone to produce 4-iodo-1-indanol; and adding a second acid to dehydrate 4-iodo-1-indanol to produce 7-iodoindene.

In one embodiment, the subject invention provides a method for synthesizing 5-iodoindene and 7-iodoindene, the method comprising or consisting of:

mixing indan-1-one with a source compound for a nitro group, optionally, in the presence of an acid, to produce a mixture of 6-nitroindan-1-one and 4-nitroindan-1-one;

adding a reducing agent to 6-nitroindan-1-one and 4-nitroindan-1-one to produce 6-aminoindan-1-one and 4-aminoindan-1-one;

mixing 6-aminoindan-1-one and 4-aminoindan-1-one with a nitrite compound and one or more iodine sources to produce 6-iodo-1-indanone and 4-iodo-1-indanone;

adding a second reducing agent to 6-iodo-1-indanone and 4-iodo-1-indanone to produce 6-iodo-1-indanol and 4-iodo-1-indanol; and adding a second acid to 6-iodo-1-indanol and 4-iodo-1-indanol to produce 5-iodoindene and 7-iodoindene.

In one embodiment, the method for synthesizing 5-iodoindene and 7-iodoindene further comprises separating each isomer from a mixture of products after each step of the method. Preferably, the method for synthesizing 5-iodoindene and 7-iodoindene further comprises a step of separating 6-nitroindan-1-one and 4-nitroindan-1-one prior to the step of reducing 6-nitroindan-1-one and 4-nitroindan-1-one to produce 6-aminoindan-1-one and 4-aminoindan-1-one in the presence of a reducing agent.

The method according to the subject invention allows preparing expensive 5-iodoindene and unreported 7-iodoindene in high yields utilizing readily available and cost-effective reagents. Advantageously, it avoids the use of expensive nitroindenes, unstable aminoindenes and potentially explosive trifluoroperacetic acid. This represents a significant improvement in overall yield from indanone-1 or aminoindan-1-one. The method of the subject invention also avoids oxidation to 5-nitroindan-1-one with trifluoroperacetic acid and does not require a reduction step to the unstable 6-aminoindene intermediate.

In one embodiment, the subject invention provides a method for synthesizing 6-iodoindene, the method comprising or consisting of:

mixing 5-aminoindan-1-one with a nitrite compound and one or more iodine sources to produce 5-iodo-1-indanone;

adding a reducing agent to 5-iodo-1-indanone to produce 5-iodo-1-indanol; and adding an acid to 5-iodo-1-indanol to produce 6-iodoindene.

In one embodiment, the nitrite compound may be, for example, t-BuONO. The iodine source comprises one or more of, for example, $I_2$, CuI, $CH_2I_2$, KI, HI, and NIS. Preferably, the iodine source is a mixture of $I_2$, CuI, and $CH_2I_2$. The diazotization-iodination reaction may also occur in the presence of a solvent, such as THF. Preferably, the reducing agent is, for example, $NaBH_4$. Optionally, the reducing step occurs in the presence of a solvent or a solvent mixture, e.g., THF/MeOH. Preferably, the acid for dehydrating 5-iodo-1-indanol is, for example, HCl. More preferably, the acid for dehydrating 5-iodo-1-indanol is aqueous HCl in THF/$H_2O$.

In one embodiment, the yield of 5-, 6-, or 7-iodoindene by the method of the subject invention is at least about 70%, about 75%, about 80%, about 85%, about 90%, about 91%, about 92%, about 93%, about 94%, about 95%, about 96%, about 97%, about 98% or about 99%. The yield of each intermediate product from each step of the method for synthesizing 5-, 6-, or 7-iodoindene is also at least about 70%, about 75%, about 80%, about 85%, about 90%, about 91%, about 92%, about 93%, about 94%, about 95%, about 96%, about 97%, about 98% or about 99%.

In one embodiment, the subject invention also provides methods of using the haloindenes synthesized by the methods of the subject invention. The iodoindenes synthesized according to the subject invention can serve as effective substrates for the regioselective Stille coupling with vinyl stannanes and for Sonogashira coupling with alkynes in the presence of triethylamine. For example, the iodoindenes were regio- and steroselectively converted to the corresponding (E)-bromovinylindenes utilizing Stille coupling with trans-1,2-bis(tributylstannyl)ethylene followed by bromodestannylation with NBS. Sonogashira coupling of iodoindenes with terminal alkyne in the presence of $Et_3N$ gave isomeric alkynylindenes.

The subject invention also provides regioselective alkenylation and further alkynylation of these compounds because the enyne species formed in these processes represent potential reaction products of a indenyl radicals with vinylacetylene and hence the iodoindenes synthesized according to the subject invention can serve as calibration compounds in studying the growth mechanism of PAH.

The subject invention provides a composition comprising a haloindene synthesized by the method of the subject invention. Preferably, the composition comprises 4-, 5-, 6-, or 7-iodoindene synthesized by the method of the subject invention. More preferably, the composition comprises 4- or 7-iodoindene synthesized by the method of the subject invention.

In one embodiment, the composition comprises a suitable solvent, carrier, vehicle and/or excipient. "Carrier," "vehicle" or "excipient" may include any and all solvents, dispersion media, and the like. Except insofar as any conventional media or agent is incompatible with the active ingredient, its use in the chemical compositions of the invention is contemplated. Supplementary active ingredients can also be incorporated into the compositions.

Further, the subject invention provides a kit comprising a composition of haloindene, e.g., 4-, 5-, 6-, or 7-iodoindene, and optionally, a container containing the composition of haloindene. The kit may also comprise a suitable solvent, carrier, vehicle and/or excipient. The kit may further comprise an instruction of using the composition of haloindene. In one embodiment, the haloindene is in a dry form such as a solid or powder. In another embodiment, the haloindene has been dissolved in a suitable solvent, carrier, vehicle and/or excipient.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., subranges within the disclosed range), specific embodiments therein are intended to be explicitly included.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed.

EXAMPLES

Experimental Section

General Information. $^1$H NMR spectra at 600 MHz and $^{13}$C NMR at 101 MHz were recorded in $CDCl_3$ unless otherwise noted. All chemical shift values are reported in parts per million (ppm) and referenced to the residual solvent peaks of $CDCl_3$ (7.26 ppm) or DMSO-$d_6$ (2.50 ppm) for $^1$H NMR and $CDCl_3$ (77.16 ppm) or DMSO-$d_6$ (39.52 ppm) peaks for $^{13}$C NMR spectra, with coupling constant (J) values reported in Hz. HRMS were recorded in TOF (APCI) negative or positive mode unless otherwise noted. Reaction progress was monitored by TLC on Merck Kieselgel 60-$F_{254}$ sheets with product detection by 254-nm light. Products were purified by column chromatography using Merck Kiselgel 60 (230-400 mesh). Reagent grade chemicals were used and solvents were purchased from commercial suppliers and used without further purification unless otherwise specified. Compounds 2a and 2b were prepared by nitration of indan-1-one 1.

Figure 3A:
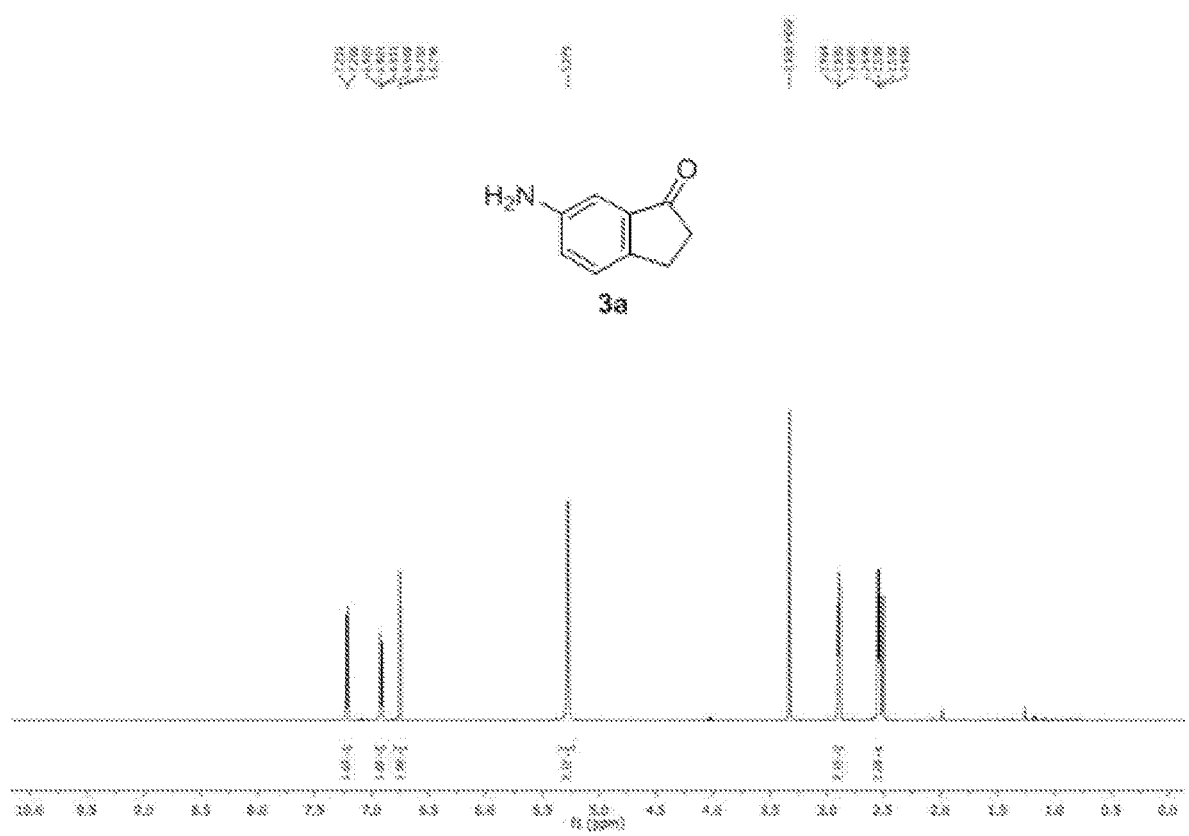
FIGS. 3A-3B show $^1$H NMR and $^{13}$C NMR spectra of compound 3a in DMSO.
Figure 3B:
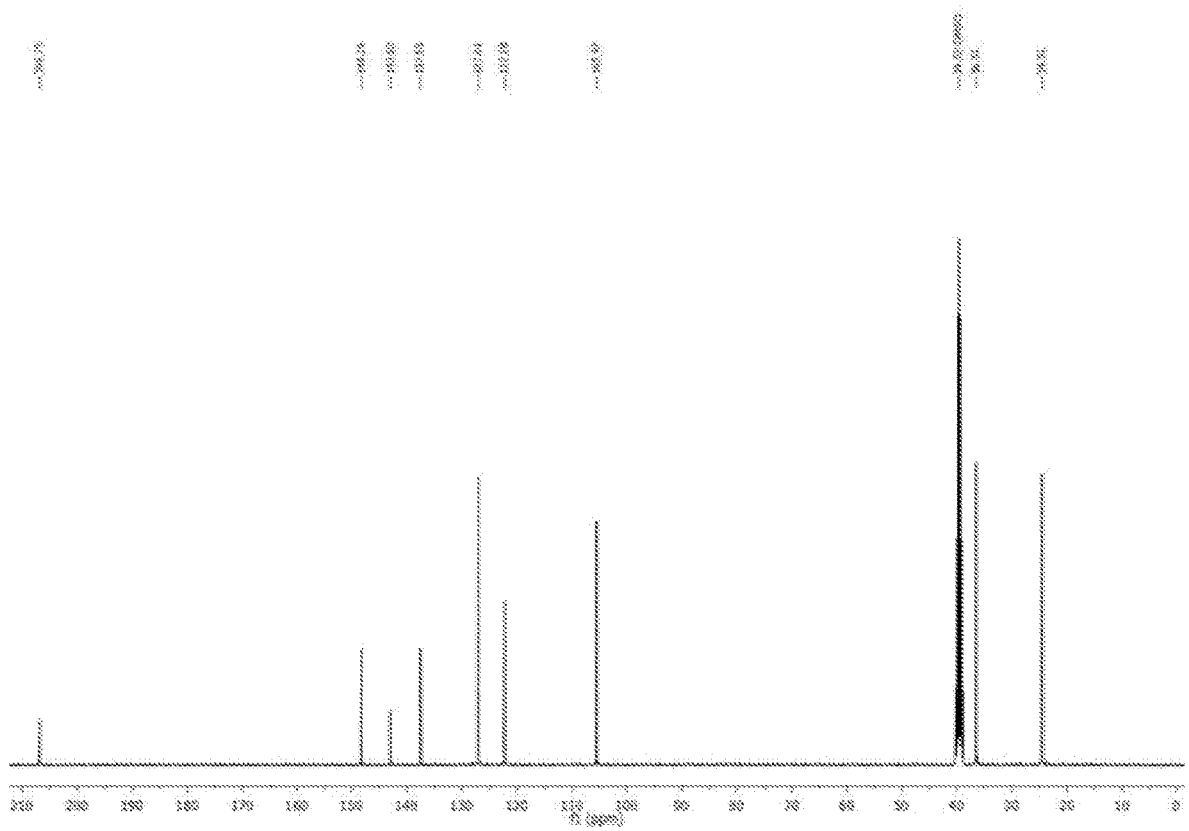

6-Amino-1-indanone (3a). Procedure A. Iron powder (6.14 g, 110 mmol) was added to the solution of $NH_4Cl$ (5.89 g, 110 mmol) in $H_2O$/EtOH (80 mL, 1:1) in 250 mL flask equipped with a stir bar. The mixture was stirred at 60° C. for 30 min to activate the iron powder. Then 6-nitro-1-indanone 2a (3.0 g, 16.9 mmol) was added and the temperature of reaction mixture was raised to 80° C. and stirring was continued for another 45 min. The mixture was cooled with ice-bath, basified with dilute aqueous NaOH to pH ~12 and was filtered to remove solid residue. The filtrate was concentrated under reduced pressure and extracted with EtOAc. The organic phase was separated, dried over anhydrous $Na_2SO_4$, filtered, and evaporated. The residue was purified by column chromatography (20→40% EtOAc/hexane) to give 3a (2.27 g, 91%) (FIG. 3): $^1$H NMR (600 MHz, DMSO-$d_6$) δ 2.52-2.59 (m, 2H), 2.86-2.93 (m, 2H), 5.28 (s, 2H), 6.75 (d, J=2.4 Hz, 1H), 6.92 (dd, J=7.8, 2.4 Hz, 1H), 7.21 (d, J=7.8 Hz, 1H); $^{13}$C NMR (101 MHz, DMSO-$d_6$) δ 24.51, 36.51, 105.47, 122.28, 127.01, 137.55, 143.02, 148.26, 206.75.

Figure 4A:
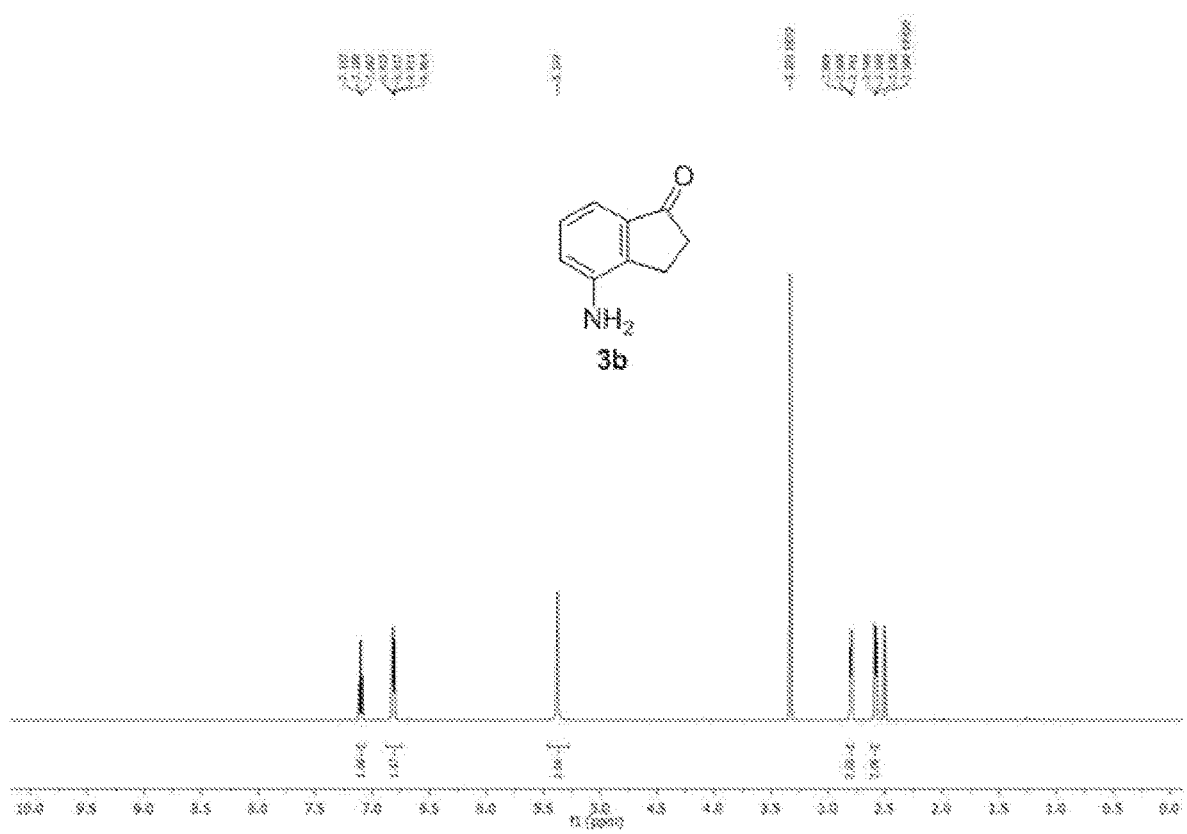
FIGS. 4A-4B show $^1$H NMR and $^{13}$C NMR spectra of compound 3b in DMSO.
Figure 4B:
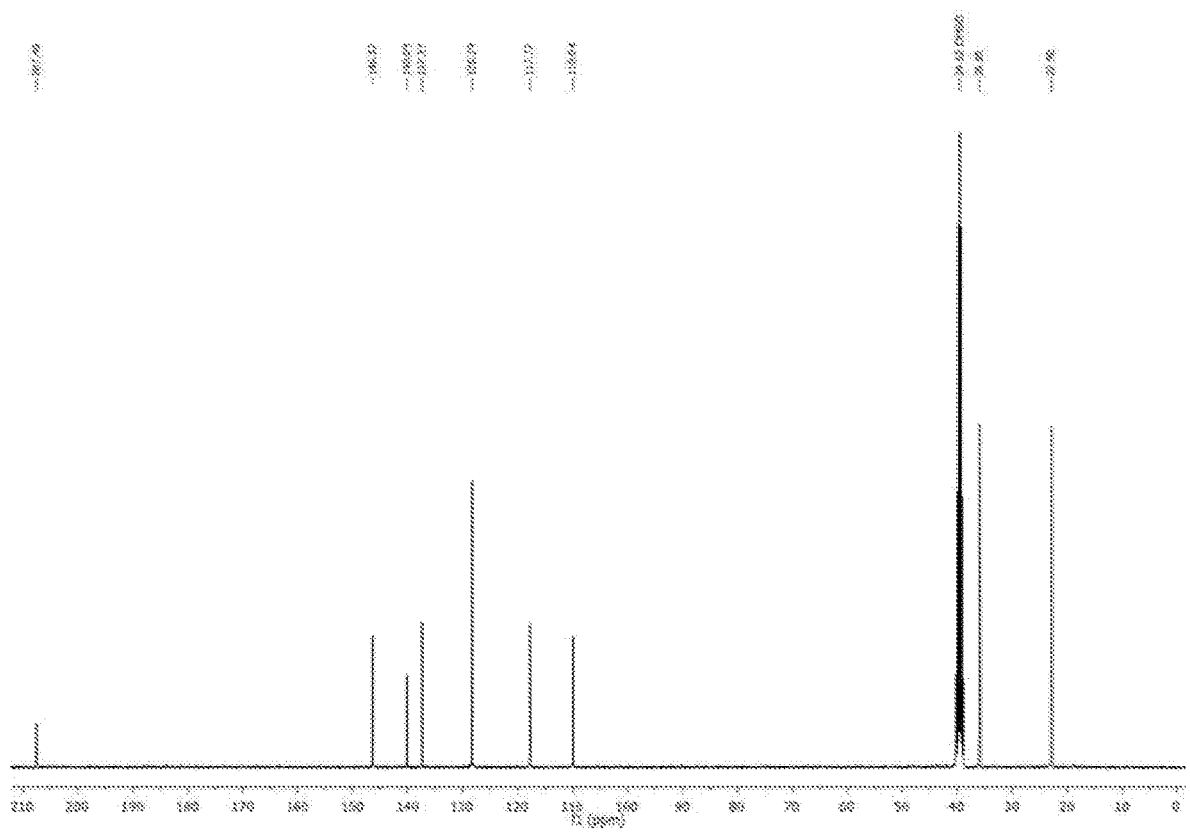

4-Amino-1-indanone (3b). Treatment of 2b (1.12 g, 6.3 mmol) with Iron powder/$NH_4Cl$ by Procedure A (column chromatography; 20→40% EtOAc/hexane) gave 3b (837 mg, 90%) (FIG. 4): $^1$H NMR (600 MHz, DMSO-$d_6$) δ 2.55-2.62 (m, 2H), 2.78-2.84 (m, 2H), 5.38 (s, 2H), 6.81 (d, J=7.8 Hz, 1H), 6.82 (d, J=7.2 Hz, 1H), 7.10 (t, J=7.8 Hz, 1H); $^{13}$C NMR (101 MHz, DMSO-$d_6$) δ 22.90, 35.85, 110.04, 117.77, 128.29, 137.37, 140.09, 146.37, 207.45; HRMS (TOF, APCI) m/z calcd for $C_9H_8NO$ 146.0600 [M−H]$^−$, found 146.0601.

Figure 5A:
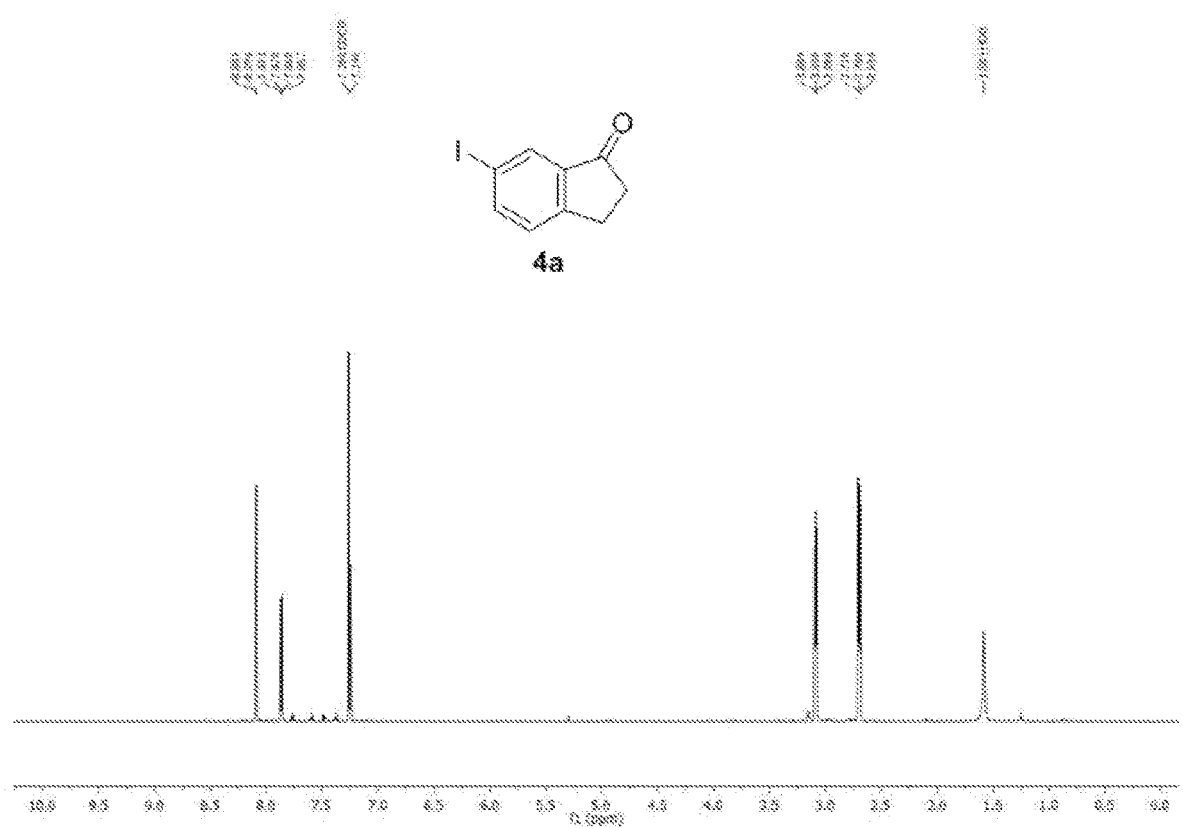
FIGS. 5A-5B show $^1$H NMR and $^{13}$C NMR spectra of compound 4a in CDCl$_3$.
Figure 5B:
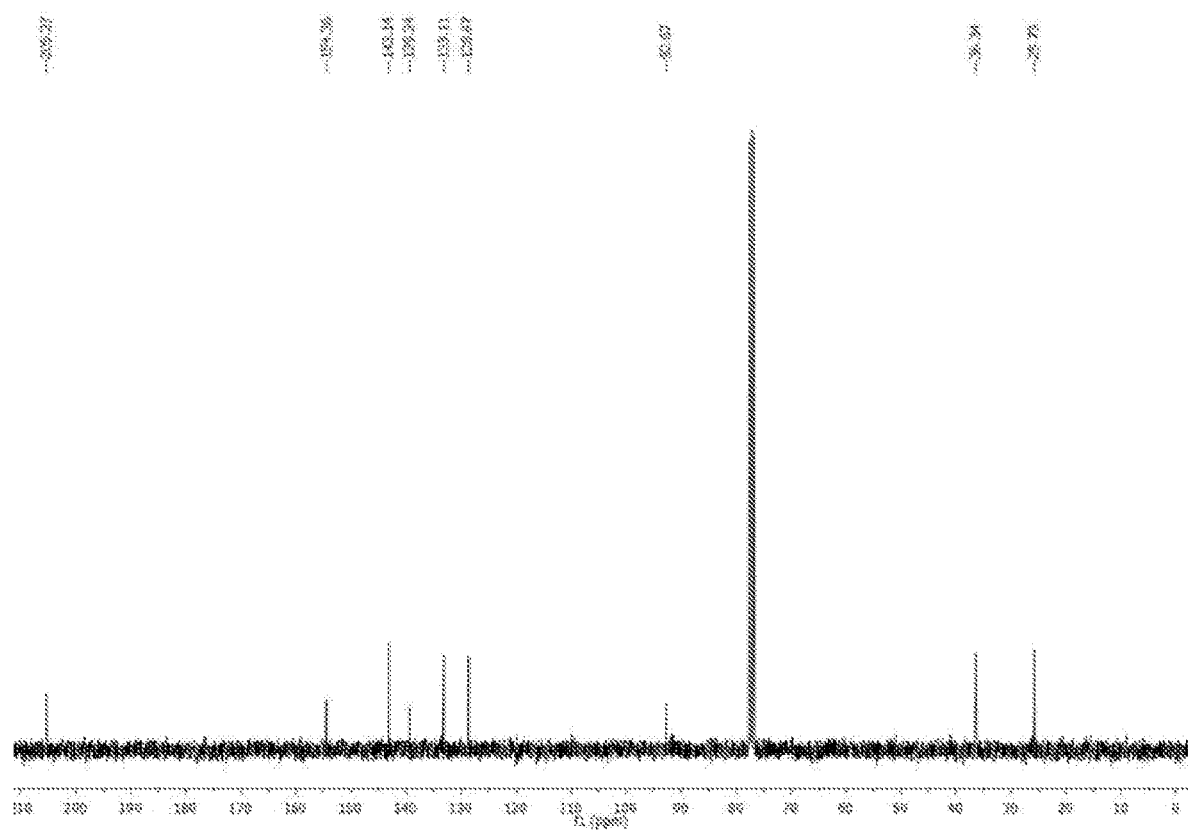

6-Iodo-1-indanone (4a). Procedure B. Iodine (5.17 g, 20.4 mmol), CuI (4.66 g, 24.5 mmol), $CH_2I_2$ (4.93 mL, 61.2 mmol), and tert-butyl nitrite (7.3 mL, 61.2 mmol) were added to a solution of 3a (3.0 g, 20.4 mmol) in dry THF (40 mL). The reaction mixture was stirred at 66° C. for 30 min, cooled to room temperature (rt), and filtered. The filtrate was concentrated under reduced pressure and extracted with EtOAc. The organic phase was separated, dried over anhydrous $Na_2SO_4$, filtered, and evaporated. The residue was purified by column chromatography (10→20% EtOAc/hexane) to give 4a (4.9 g, 93%) (FIG. 5): $^1$H NMR (600 MHz, CDCl$_3$) δ 2.69-2.72 (m, 2H), 3.07-3.11 (m, 2H), 7.25 (d, J=8.4, 1H), 7.87 (dd, J=7.8, 1.8 Hz, 1H), 8.09 (d, J=1.8 Hz, 1H); $^{13}$C NMR (75 MHz, CDCl$_3$) δ 25.73, 36.34, 92.67, 128.67, 133.11, 139.34, 143.14, 154.36, 205.27; HRMS (TOF, APCI) m/z calcd for $C_9H_6IO$ 256.9469 [M−H]$^−$, found 256.9470.

Figure 6A:
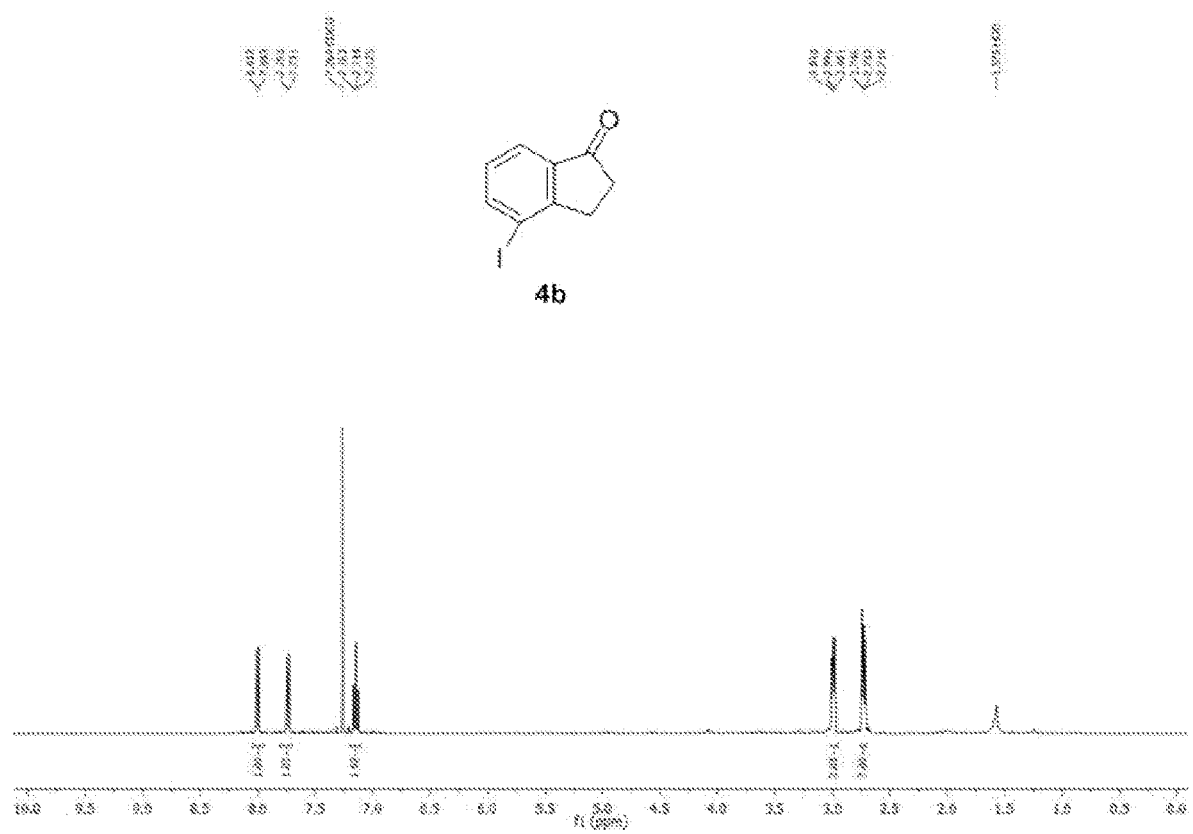
FIGS. 6A-6B show $^1$H NMR and $^{13}$C NMR spectra of compound 4b in CDCl$_3$.
Figure 6B:
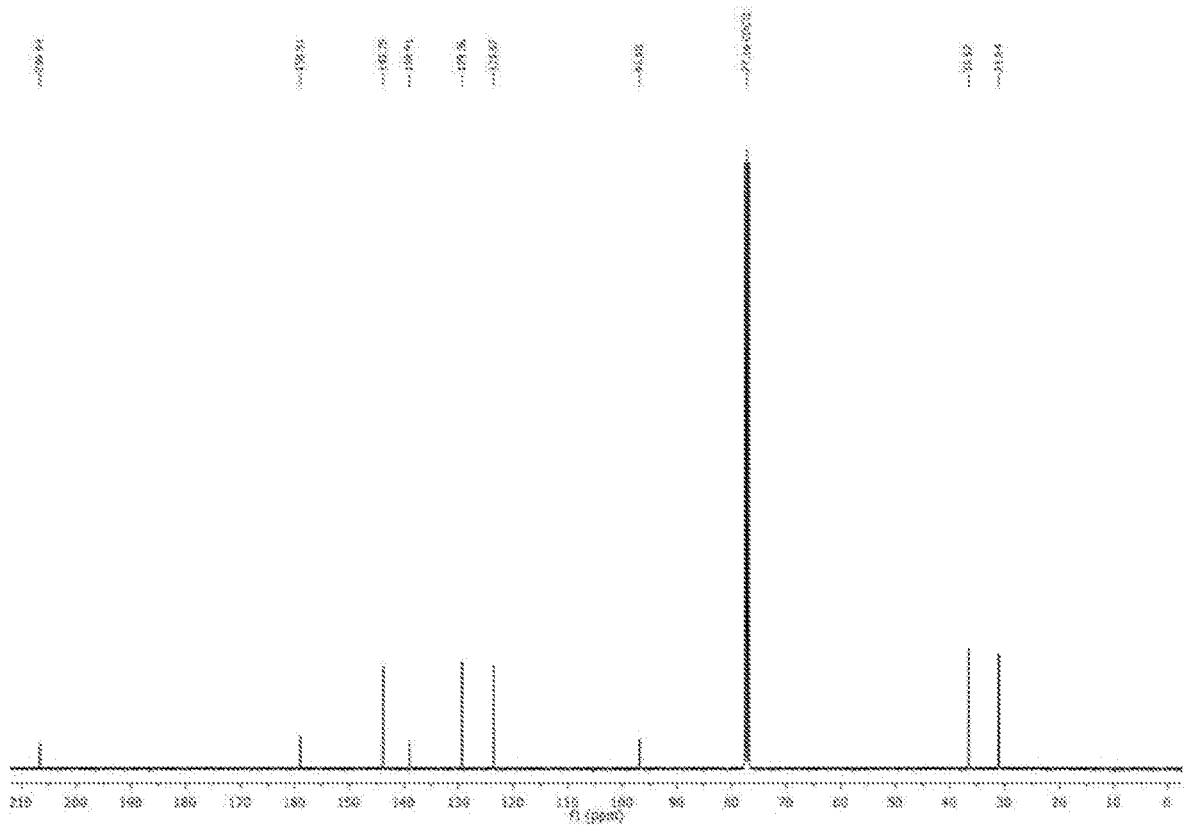

4-Iodo-1-indanone (4b). Treatment of 3b (736 mg, 5.0 mmol) with tert-butyl nitrite by Procedure B (column chromatography; 10→20% EtOAc/hexane) gave 4b (1.17 g, 90%) (FIG. 6): $^1$H NMR (400 MHz, CDCl$_3$) δ 2.71-2.76 (m, 2H), 2.95-3.02 (m, 2H), 7.14 (t, J=7.6 Hz, 1H), 7.74 (d, J=7.6 Hz, 1H), 8.00 (d, J=7.6 Hz, 1H); $^{13}$C NMR (101 MHz, CDCl$_3$) δ 31.04, 36.57, 96.80, 123.57, 129.36, 138.91, 143.75, 158.91, 206.64; HRMS (TOF, APCI) m/z calcd for $C_9H_6IO$ 256.9469 [M−H]$^−$, found 256.9470.

Figure 7A:
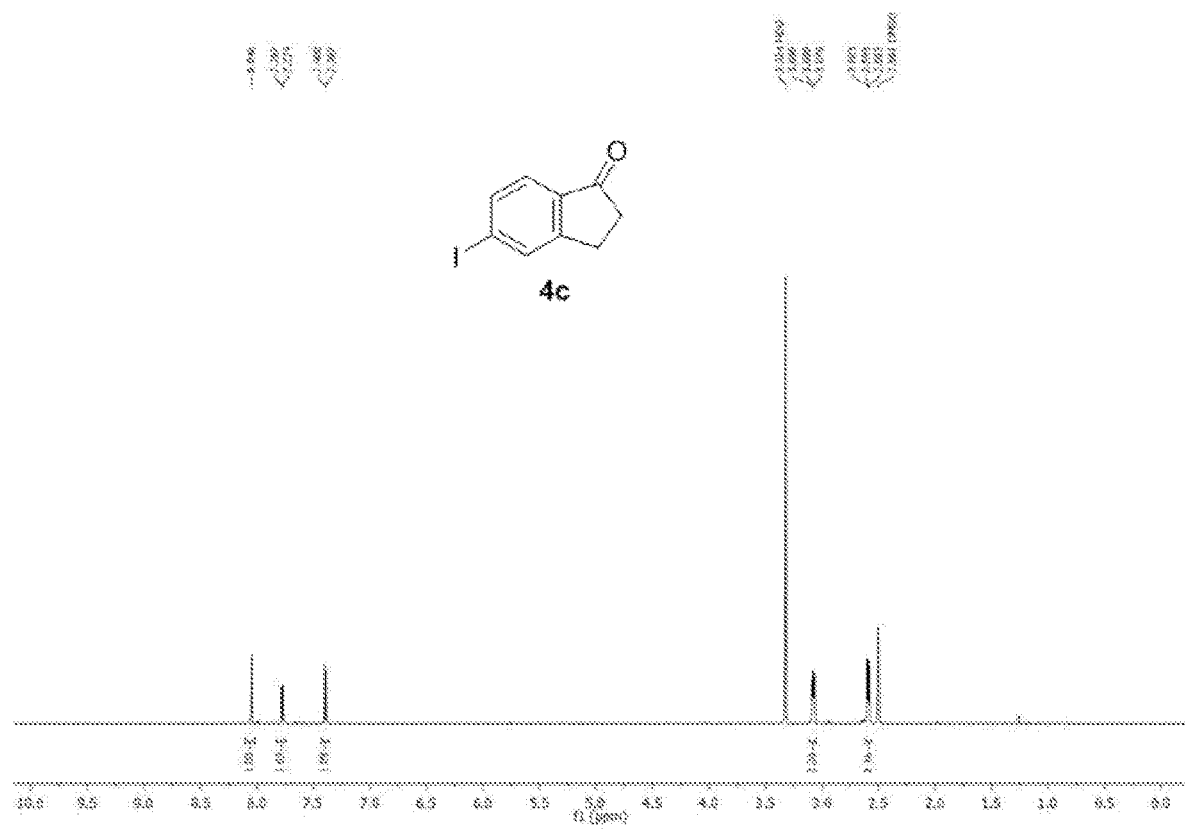
FIGS. 7A-7B show $^1$H NMR and $^{13}$C NMR spectra of compound 4c in DMSO.
Figure 7B:
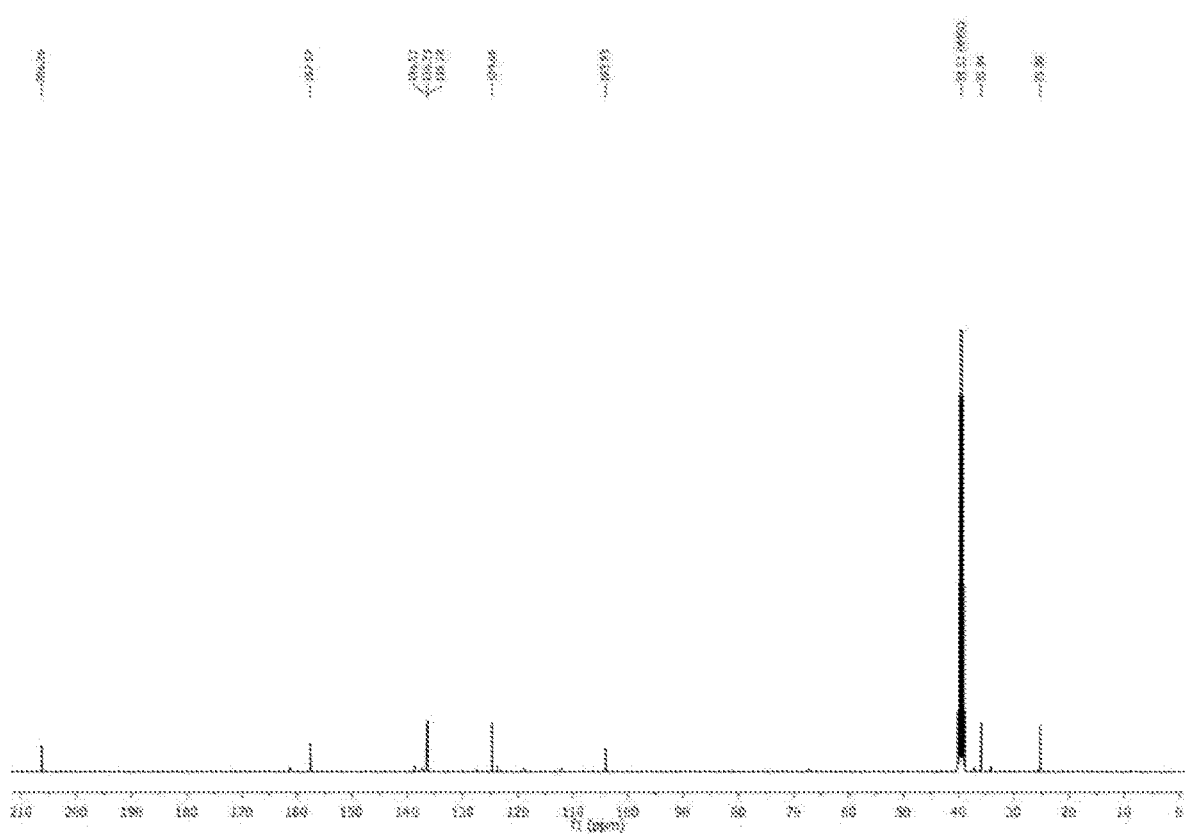

5-Iodo-1-indanone (4c). Treatment of 3c (2.5 g, 19.0 mmol) with tert-butyl nitrite by Procedure B (column chromatography; 10→20% EtOAc/hexane) gave 4c (4.42 g, 90%) (FIG. 7): $^1$H NMR (600 MHz, DMSO-$d_6$) δ 2.56-2.62 (m, 2H), 3.06-3.11 (m, 2H), 7.39 (d, J=7.8 Hz, 1H), 7.78 (d, J=7.8 Hz, 1H), 8.05 (s, 1H); $^{13}$C NMR (101 MHz, DMSO-$d_6$) δ 25.30, 35.94, 103.93, 124.65, 136.28, 136.33, 136.52, 157.57, 206.26; HRMS (TOF, APCI) m/z calcd for $C_9H_6IO$ 256.9469 [M−H]$^−$, found 256.9470.

Figure 8A:
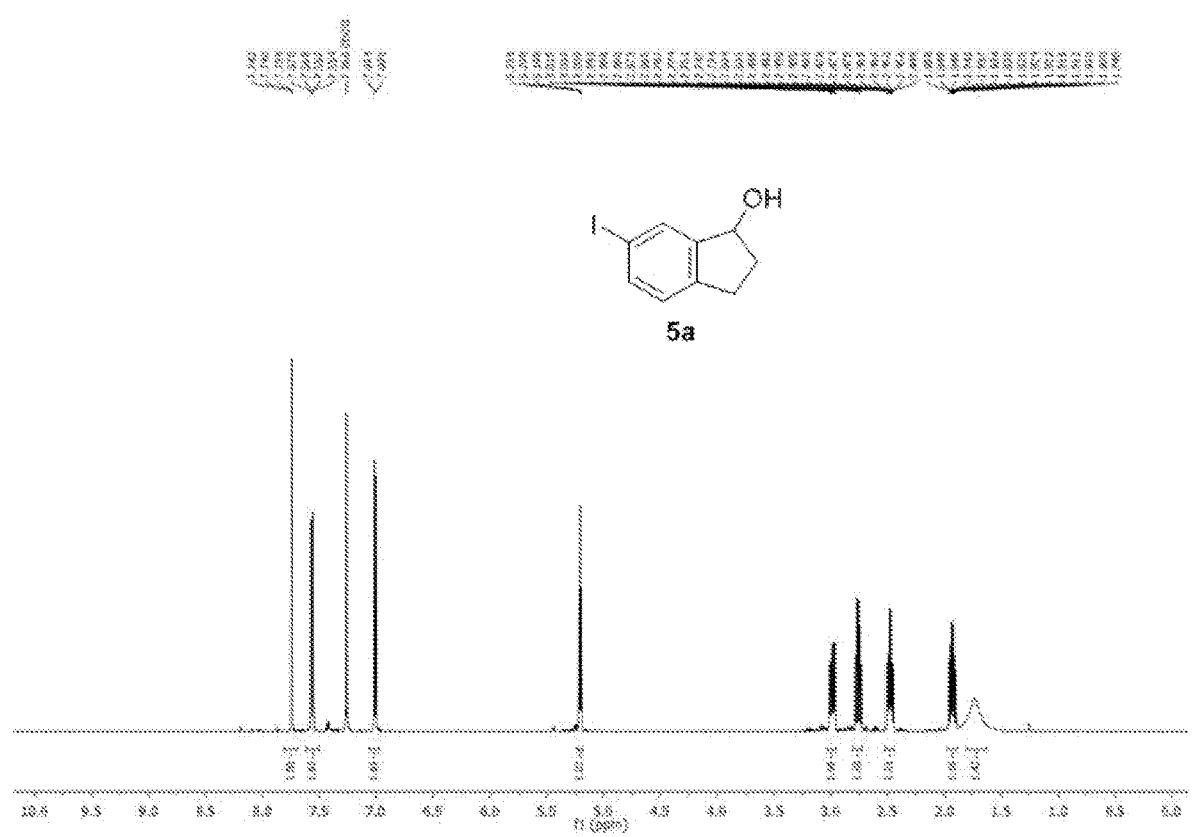
FIGS. 8A-8B show $^1$H NMR and $^{13}$C NMR spectra of compound 5a in CDCl$_3$.
Figure 8B:
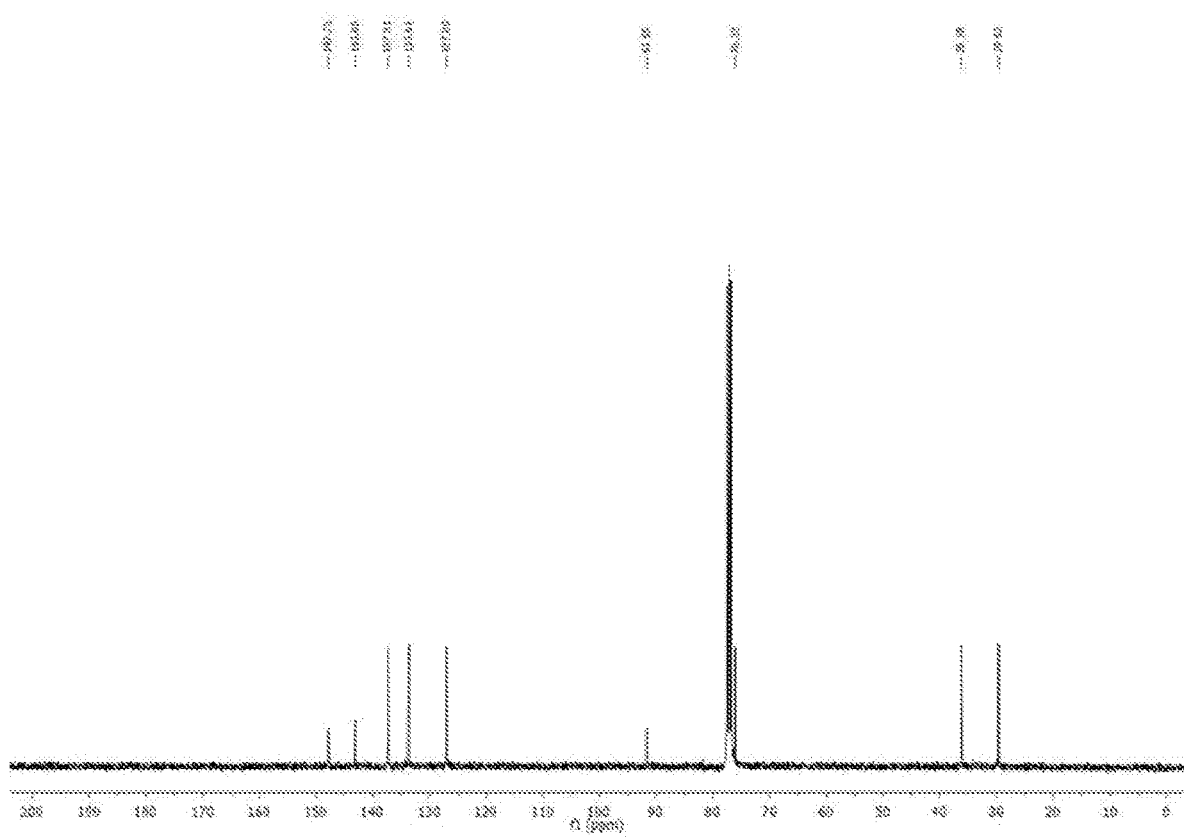

6-Iodo-1-indanol (5a). Procedure C. $NaBH_4$ (2.1 g, 55.5 mmol) was added portion wise to a stirred solution of 4a (3.62 g, 14.0 mmol) in dry MeOH/THF (60 mL, 2;1) at 0° C. (ice-bath). After 5 min, the reaction mixture was allowed to warm to ambient temperature and stirring was continued for 30 min. Water (10 mL) was then added to quench the reaction. The mixture was concentrated under reduced pressure and extracted with EtOAc. The organic phase was separated, dried over anhydrous $Na_2SO_4$, filtered, and evaporated. The residue was purified by column chromatography (20→40% EtOAc/hexane) to give 5a (3.57 g, 98%) as a white solid (FIG. 8): $^1$H NMR (600 MHz, CDCl$_3$) δ 1.74 (brs, 1H), 1.90-1.96 (m, 1H), 2.45-2.51 (m, 1H), 2.73-2.79 (m, 1H), 2.99 (ddd, J=16.2, 8.4, 4.2 Hz, 1H), 5.21 (t, J=6.2 Hz, 1H), 7.01 (d, J=7.8 Hz, 1H), 7.56 (dd, J=7.8, 1.8 Hz, 1H), 7.74 (s, 1H); $^{13}$C NMR (101 MHz, CDCl$_3$) δ 29.62, 36.18, 76.12, 91.65, 127.00, 133.61, 137.31, 143.06, 147.75; HRMS (TOF, APCI) m/z calcd for $C_9H_8IO$ 258.9625 [M−H]$^−$, found 258.9626.

Figure 9A:
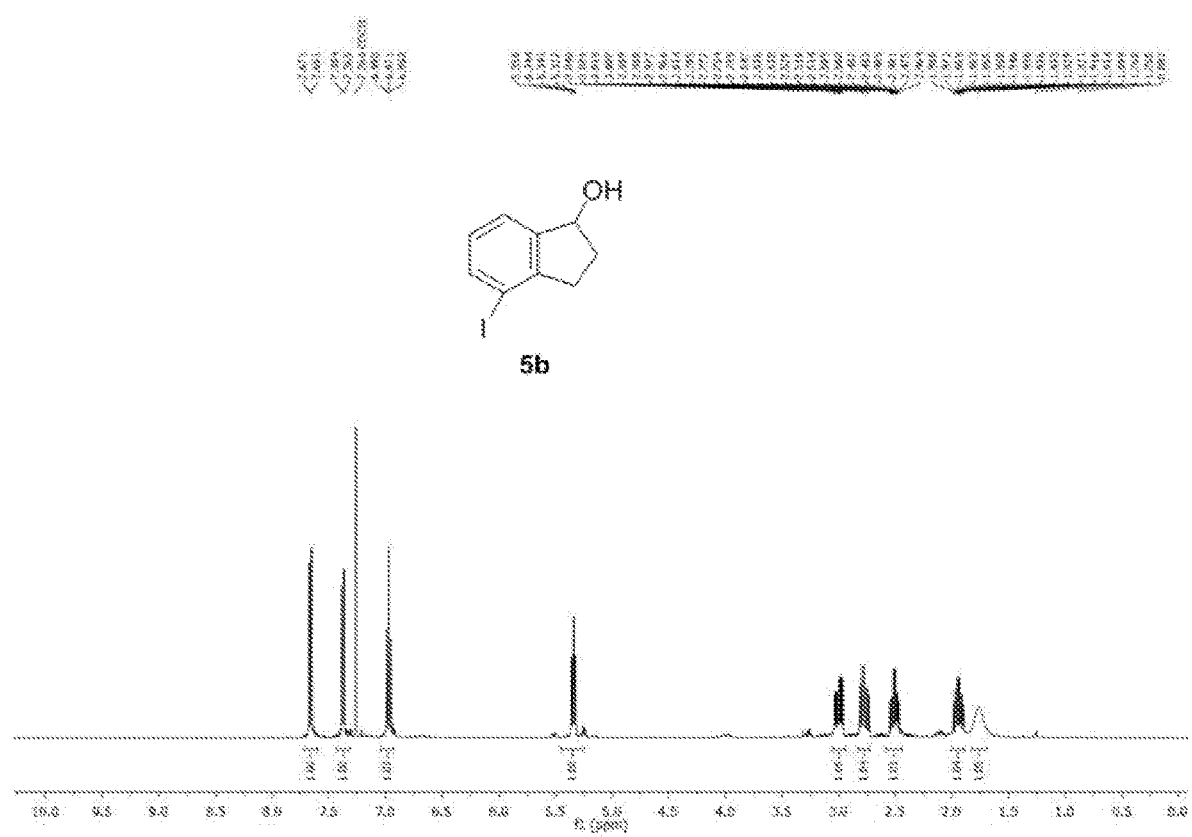
FIGS. 9A-9B show $^1$H NMR and $^{13}$C NMR spectra of compound 5b in CDCl$_3$.
Figure 9B:
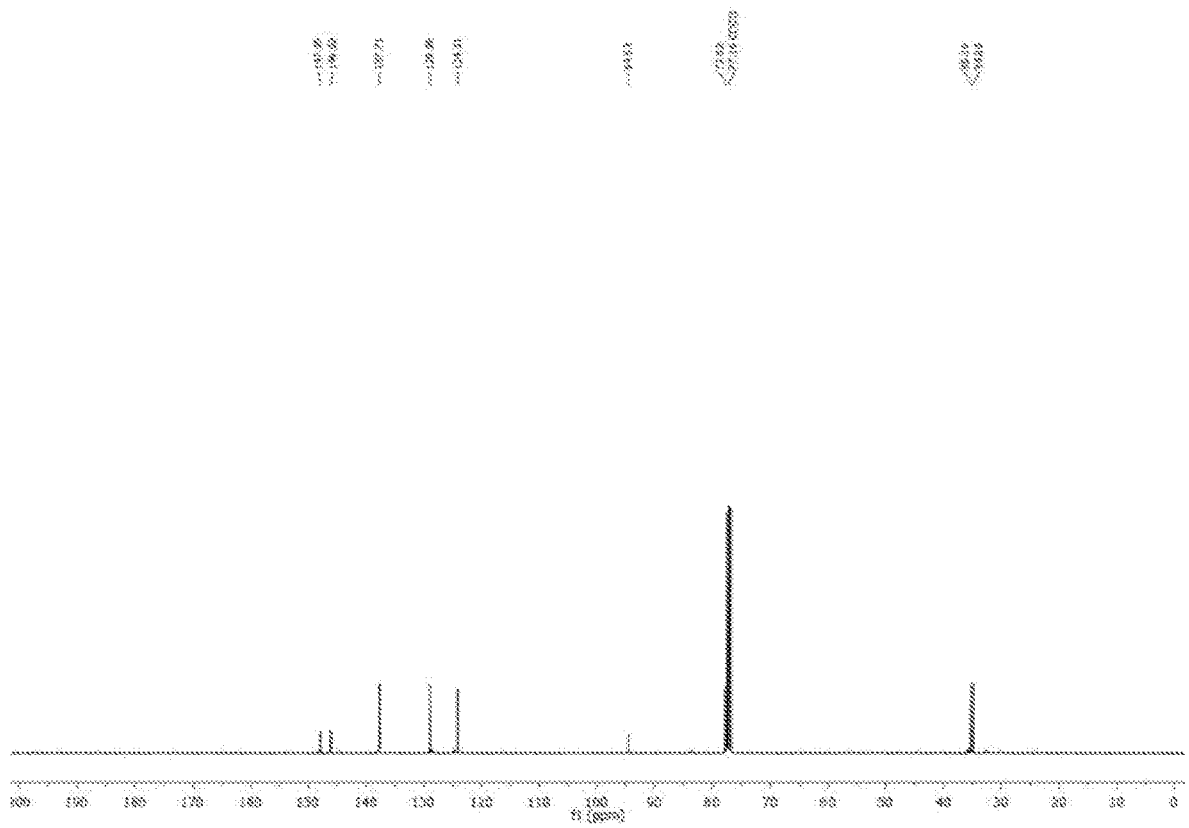

4-Iodo-1-indanol (5b). Treatment of 4b (220 mg, 0.77 mmol) with $NaBH_4$ by Procedure C (column chromatography; 20→40% EtOAc/hexane) gave 5b (198 g, 99%) (FIG. 9): $^1$H NMR (400 MHz, CDCl$_3$) δ 1.77 (brs, 1H), 1.89-2.00 (m, 1H), 2.46-2.55 (m, 1H), 2.73-2.83 (m, 1H), 3.00 (ddd, J=16.4, 8.8, 4.4 Hz, 1H), 5.34 (dd, J=6.8, 5.2 Hz, 1H), 6.97 (t, J=7.6 Hz, 1H), 7.37 (d, J=7.6 Hz, 1H), 7.66 (d, J=8.0 Hz, 1H); $^{13}$C NMR (101 MHz, CDCl$_3$) δ 34.80, 35.26, 77.82, 94.53, 124.11, 128.86, 137.71, 146.02, 147.85; HRMS (TOF, APCI) m/z calcd for $C_9H_8IO$ 258.9625 [M−H]$^−$, found 258.9625.

Figure 10A:
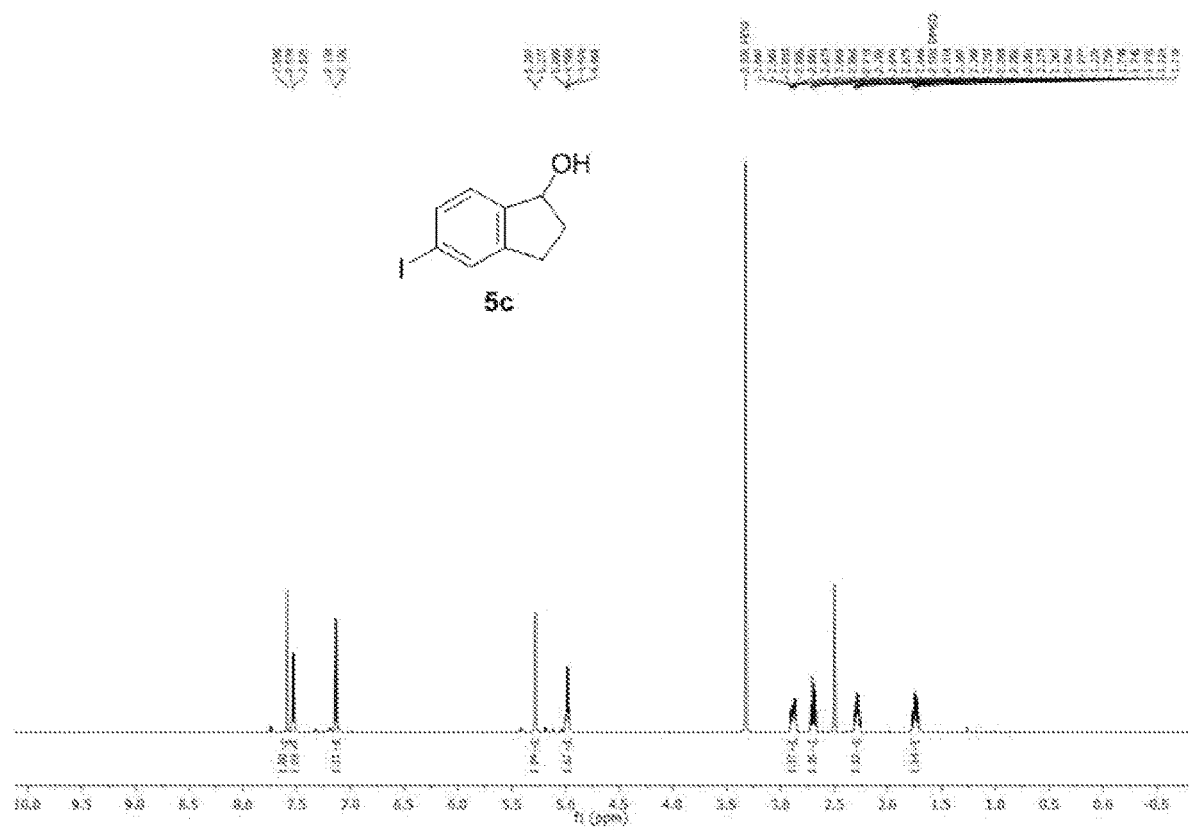
FIGS. 10A-10B show $^1$H NMR and $^{13}$C NMR spectra of compound 5c in DMSO.
Figure 10B:
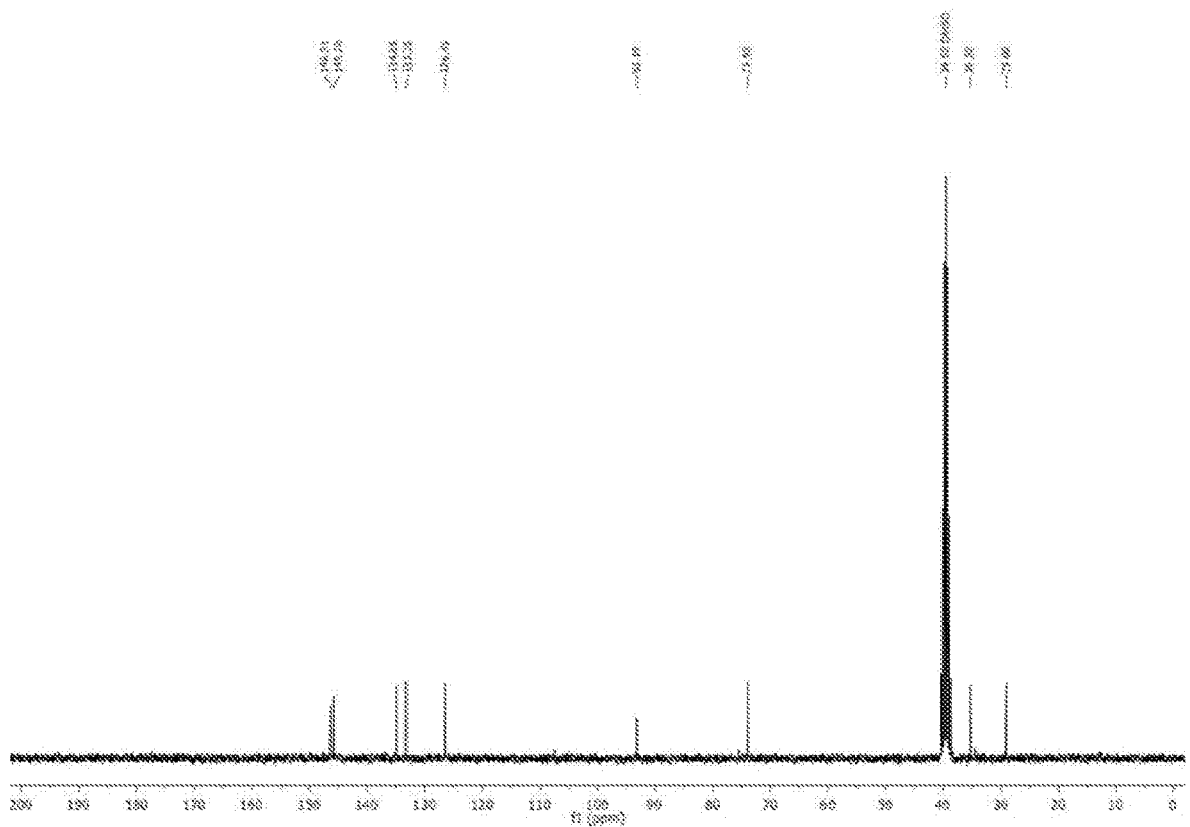

5-Iodo-1-indanol (5c). Treatment of 4c (3.36 g, 13.0 mmol) with $NaBH_4$ by Procedure C (column chromatography; 20→40% EtOAc/hexane) gave 5c (3.31 g, 98%) (FIG. 10): $^1$H NMR (600 MHz, DMSO-$d_6$) δ 1.71-1.78 (m, 1H),), 2.26-2.32 (m, 1H), 2.66-2.73 (m, 1H), 2.88 (ddd, J=15.6, 8.4, 3.6 Hz, 1H), 4.98 (dd, J=12.6, 6.0 Hz, 1H), 5.28 (d, J=6.0 Hz, 1H), 7.13 (d, J=7.8 Hz, 1H), 7.53 (d, J=7.8 Hz, 1H), 7.59 (s, 1H); $^{13}$C NMR (75 MHz, DMSO-$d_6$) δ 29.00, 35.32, 73.93, 93.19, 126.45, 133.25, 134.85, 145.70, 146.31; HRMS (TOF, APCI) m/z calcd for $C_9H_8IO$ 258.9625 [M−H]$^−$, found 258.9626.

Figure 11A:
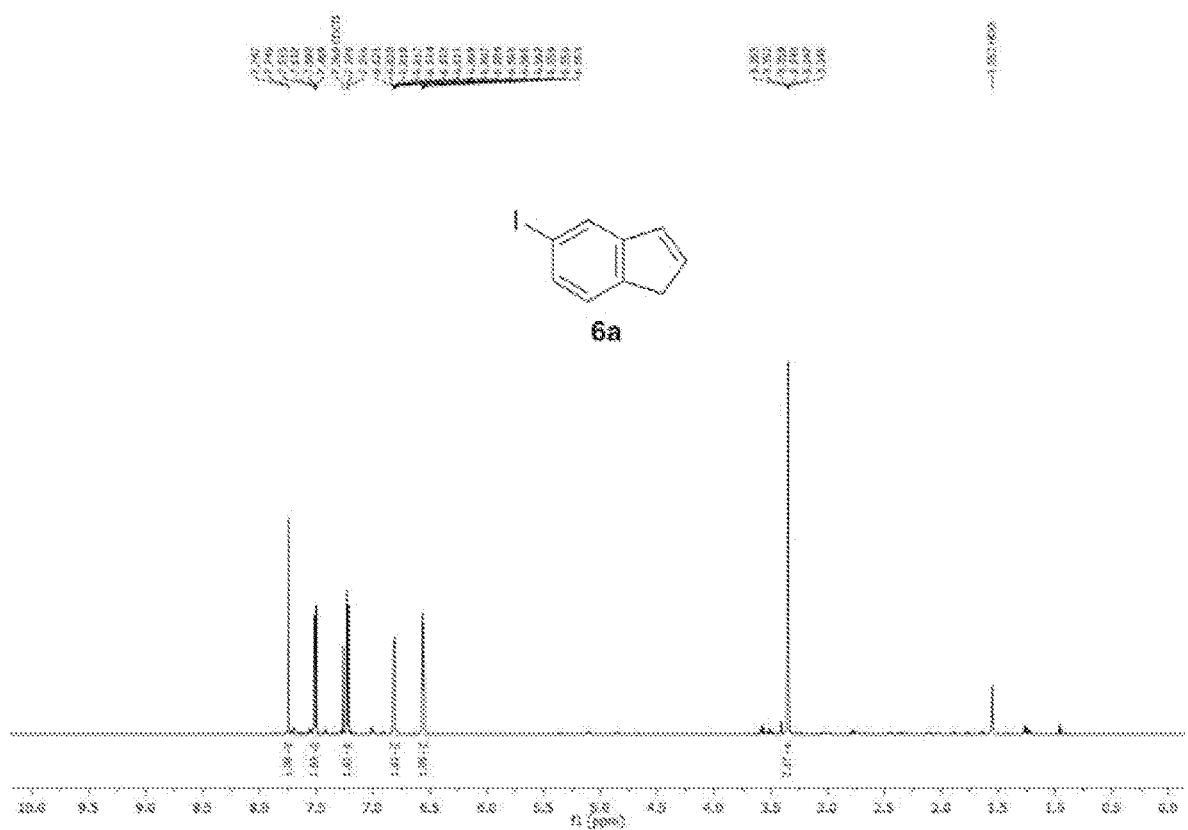
FIGS. 11A-11B show $^1$H NMR and $^{13}$C NMR spectra of compound 6a in CDCl$_3$.
Figure 11B:
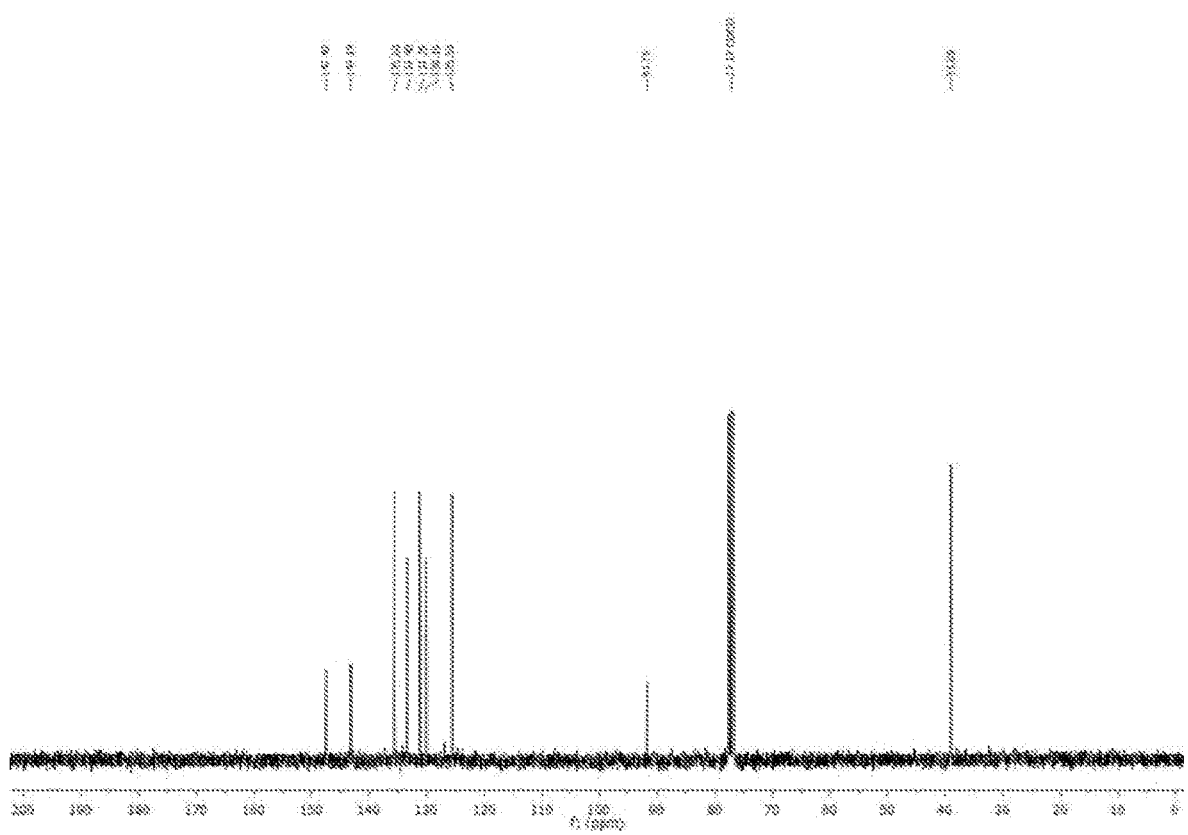

5-Iodoindene (6a). Procedure D. Alcohol 5a (3.0 g, 11.5 mmol) was dissolved in THF/$H_2O$ (40 mL, 1:1). Aqueous 6 N HCl (10.0 mL, 60 mmol) was then added and the resulting mixture was refluxed at 105° C. for 24 h. The reaction mixture was concentrated under reduced pressure to approximately 20 mL and was transferred to a separatory funnel and extracted with EtOAc. The organic phase was separated, dried over anhydrous $Na_2SO_4$, filtered, and evaporated at reduced pressure. The residue was purified by column chromatography (n-hexane) to give 6a (2.28 g, 82%) as a white solid (FIG. 11): $^1$H NMR (600 MHz, CDCl$_3$) δ 3.34-3.36 (m, 2H), 6.56 (dt, J=5.4, 1.8 Hz, 1H), 6.80-6.82 (m, 1H), 7.22 (d, J=7.8 Hz, 1H), 7.51 (dd, J=7.8, 1.8 Hz, 1H), 7.75 (d, J=1.2 Hz, 1H); $^{13}$C NMR (75 MHz, CDCl$_3$) δ 39.00, 91.76, 125.59, 130.15, 131.25, 133.40, 135.60, 143.19, 147.42: HRMS (TOF, APCI) m/z calcd for $C_9H_6I$ 240.9519 [M−H]$^−$, found 240.9518.

Figure 12A:
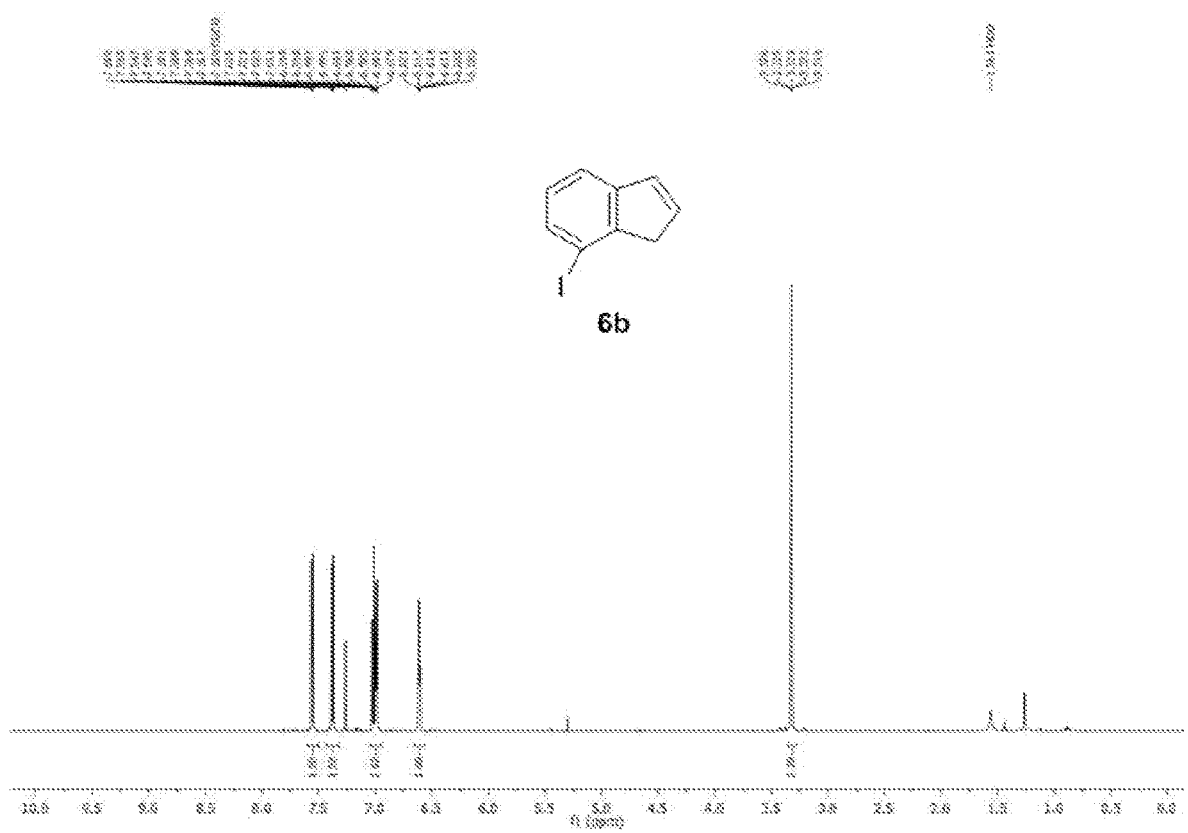
FIGS. 12A-12B show $^1$H NMR and $^{13}$C NMR spectra of compound 6b in CDCl$_3$.
Figure 12B:
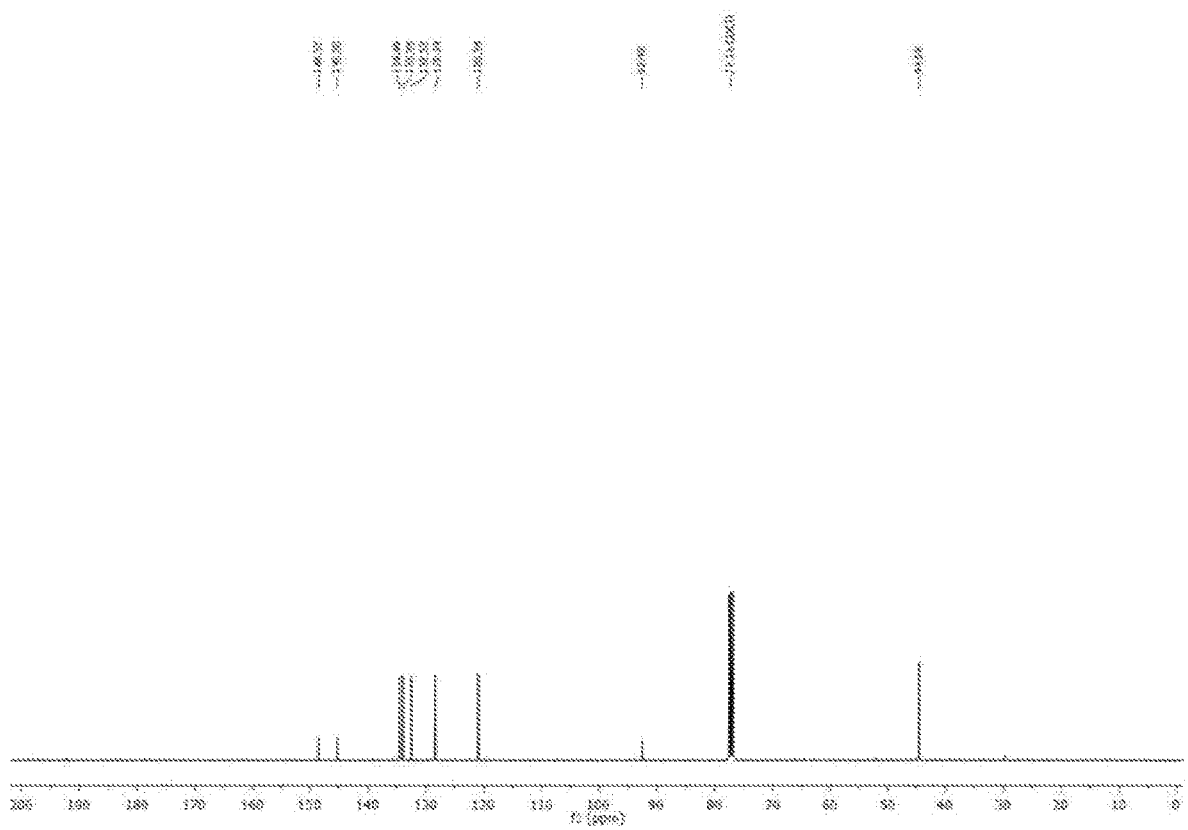

7-Iodoindene (6b). Treatment of 5b (180 mg, 0.69 mmol) with 6 N HCl by Procedure D (column chromatography; n-hexane) gave 6b (134 mg, 80%) (FIG. 12): $^1$H NMR (600

MHz, CDCl$_3$) δ 3.32-3.33 (m, 2H), 6.61 (dt, J=5.4, 1.8 Hz, 1H), 6.95-7.04 (m, 2H), 7.37 (dd, J=7.8, 1.2 Hz, 1H), 7.55 (dd, J=7.8, 1.2 Hz, 1H); $^{13}$C NMR (101 MHz, CDCl$_3$) δ 44.58, 92.48, 120.94, 128.34, 132.52, 133.99, 134.49, 145.30, 148.52; HRMS (TOF, APCI) m/z calcd for C$_9$H$_6$I 240.9519 [M−H]$^−$, found 240.9517.

Figure 13A:
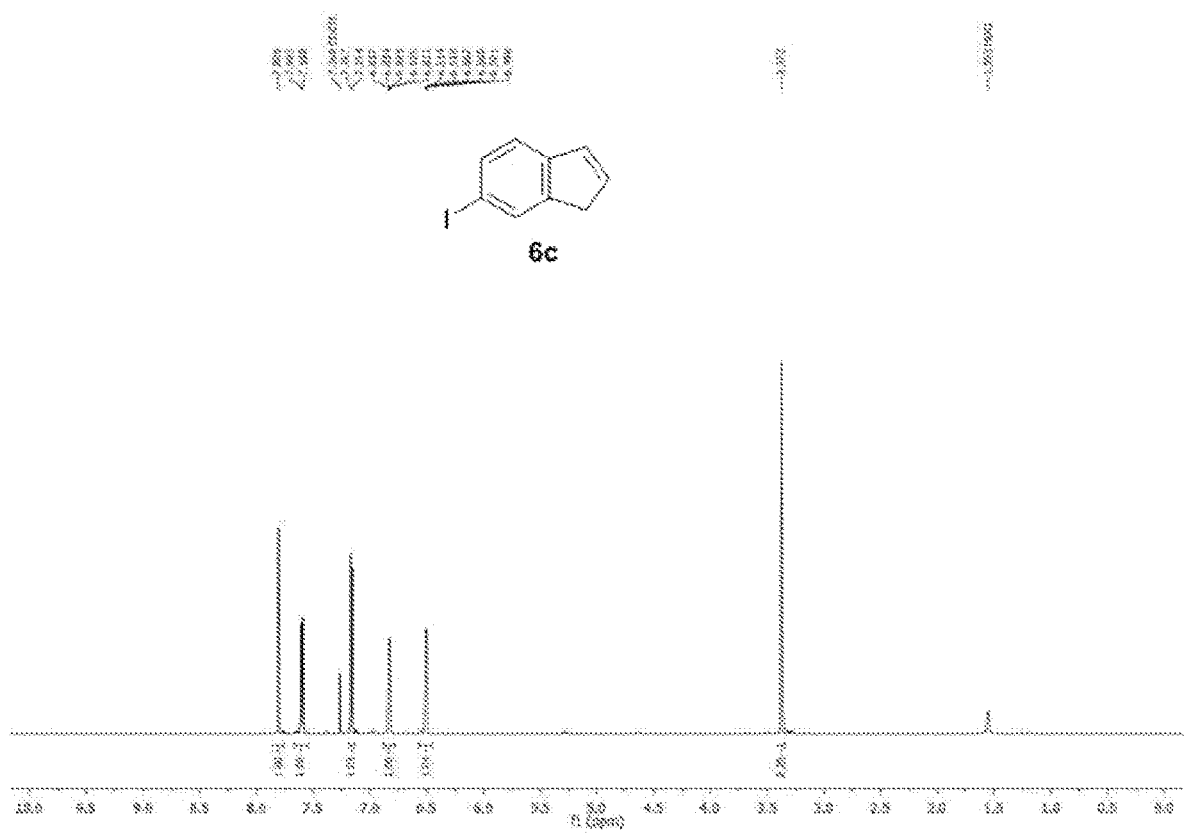
FIGS. 13A-13B show $^1$H NMR and $^{13}$C NMR spectra of compound 6c in CDCl$_3$.
Figure 13B:
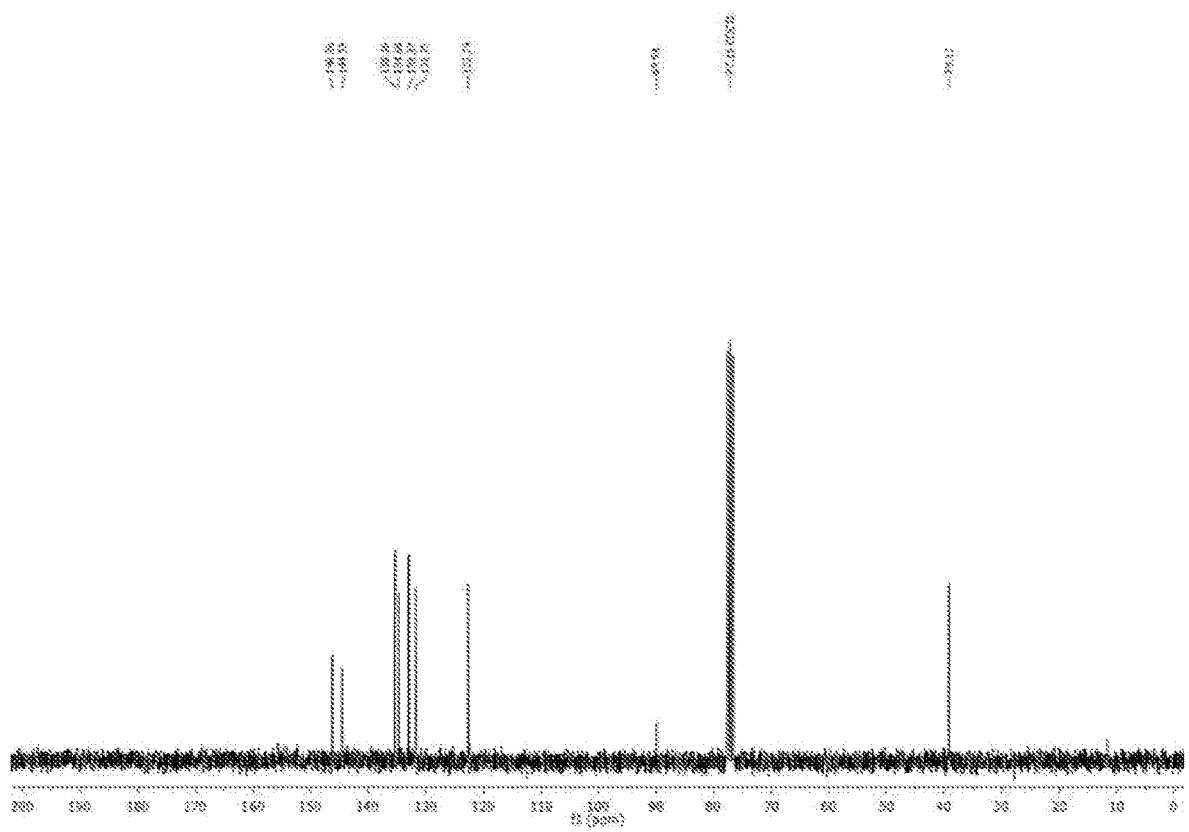

6-Iodoindene (6c). Treatment of 5c (3.0 g, 11.5 mmol) with 6 N HCl by Procedure D (column chromatography; n-hexane) gave 6c (2.23 g, 80%) (FIG. 13): $^1$H NMR (600 MHz, CDCl$_3$) δ 3.37 (s, 2H), 6.51 (dt, J=5.4, 1.8 Hz, 1H), 6.83 (dd, J=5.4, 2.4 Hz, 1H), 7.16 (d, J=7.8 Hz, 1H), 7.60 (d, J=7.8 Hz, 1H), 7.81 (s, 1H); $^{13}$C NMR (75 MHz, CDCl$_3$) δ 39.12, 89.94, 122.74, 131.75, 132.97, 134.68, 135.36, 144.53, 146.26: HRMS (TOF, APCI) m/z calcd for C$_9$H$_6$I 240.9519 [M−H]$^−$, found 240.9518.

Figure 15A:
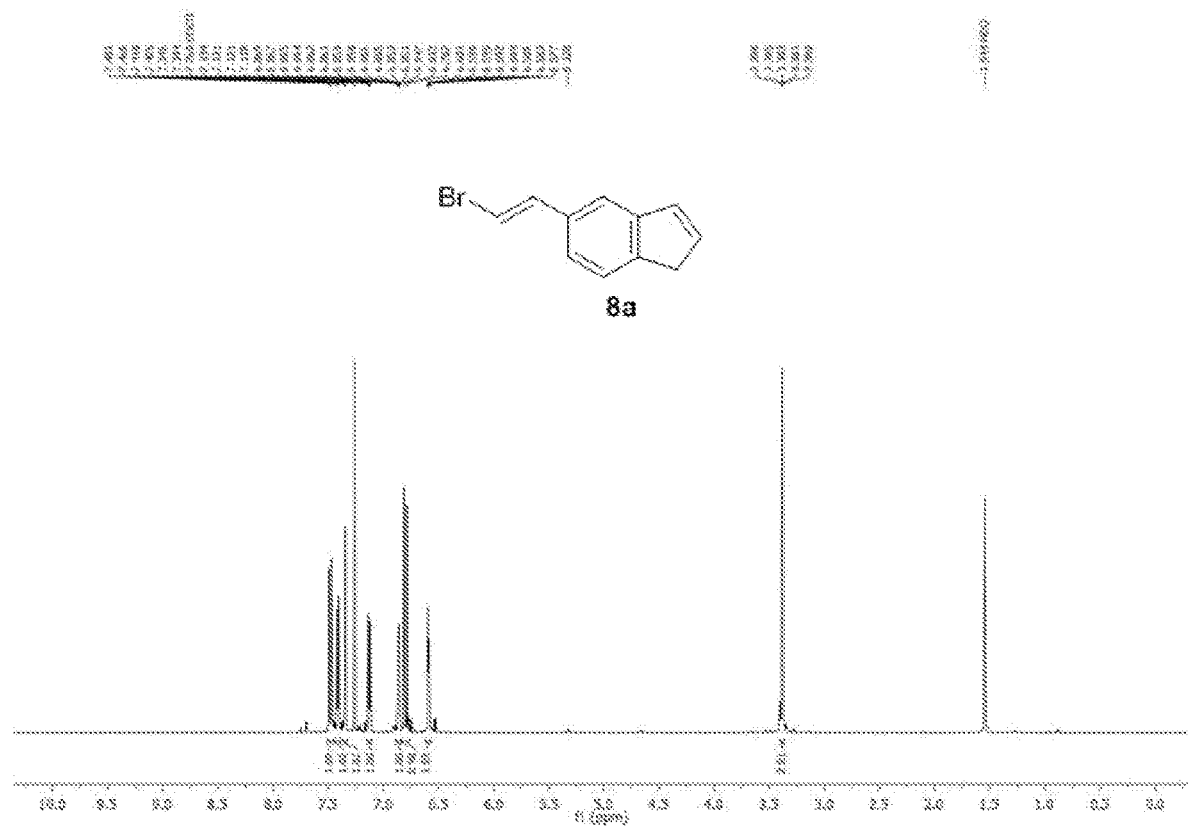
FIGS. 15A-15B show $^1$H NMR and $^{13}$C NMR spectra of compound 8a in CDCl$_3$.
Figure 15B:
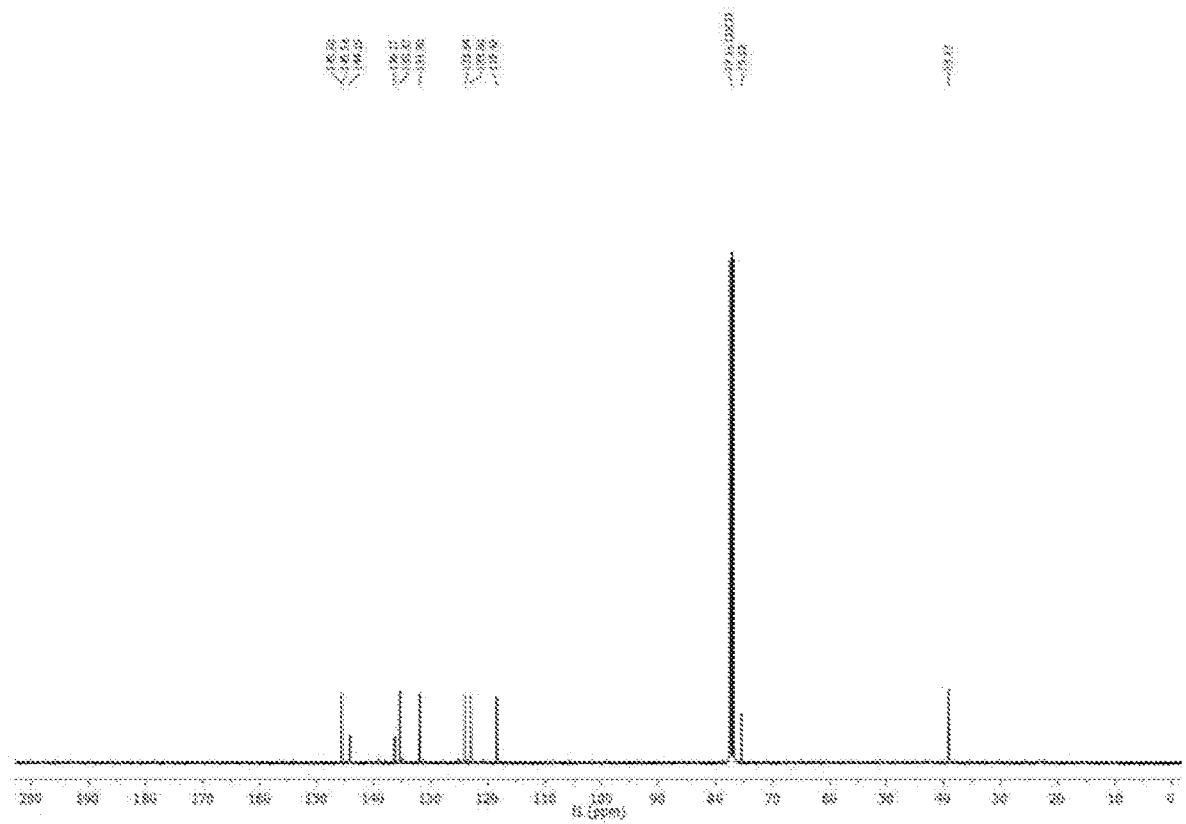

(E)-5-(2-Bromovinyl)indene (8a). Procedure E. A flame dry round bottom flask equipped with a magnetic stirrer was charged with 5-iodoindene 6a (484.1 mg, 2.0 mmol), trans-1,2-bis(tri-n-butylstannyl)ethylene (1.3 mL, 1470 mg, 2.4 mmol), dry toluene (10 mL) and Pd(PPh$_3$)$_4$ (46.2 mg, 0.04 mmol) and the resulting mixture was degassed with N$_2$ for 20 min. The reaction mixture was then heated (oil bath) at 100° C. for 1 h. Removal of volatiles under reduced pressure afforded crude (E)-5-(2-(tributylstannyl)vinyl)indene 7a, which was directly used in the next bromodestannylation step without further purification. NBS (534 mg, 3.0 mmol) was added portion wise to a stirred solution of all crude 7a in dry DCM (10 mL) at −10° C. and was stirred for 30 min. The volatiles were evaporated and the residue was purified by column chromatography (n-hexane) to give 8a (310 mg, 70%) as an off-white solid (FIG. 15): $^1$H NMR (600 MHz, CDCl$_3$) δ 3.37-3.40 (m, 2H), 6.58-6.60 (m, 1H), 6.80 (d, J=15.0 Hz, 1H), 6.85-6.87 (m, 1H), 7.13 (dd, J=7.8, 1.8 Hz, 1H), 7.35 (d, J=1.2 Hz, 1H), 7.41 (d, J=7.8 Hz, 1H), 7.48 (d, J=15.0 Hz, 1H); $^{13}$C NMR (101 MHz, CDCl$_3$) δ 39.12, 75.52, 118.42, 123.00, 123.94, 131.90, 135.32, 136.27, 144.15, 145.54, 145.60; HRMS (TOF, APCI) m/z calcd for C$_{11}$H$_8$$^{79}$Br 218.9815 [M−H]$^−$, found 218.9814.

Figure 16A:
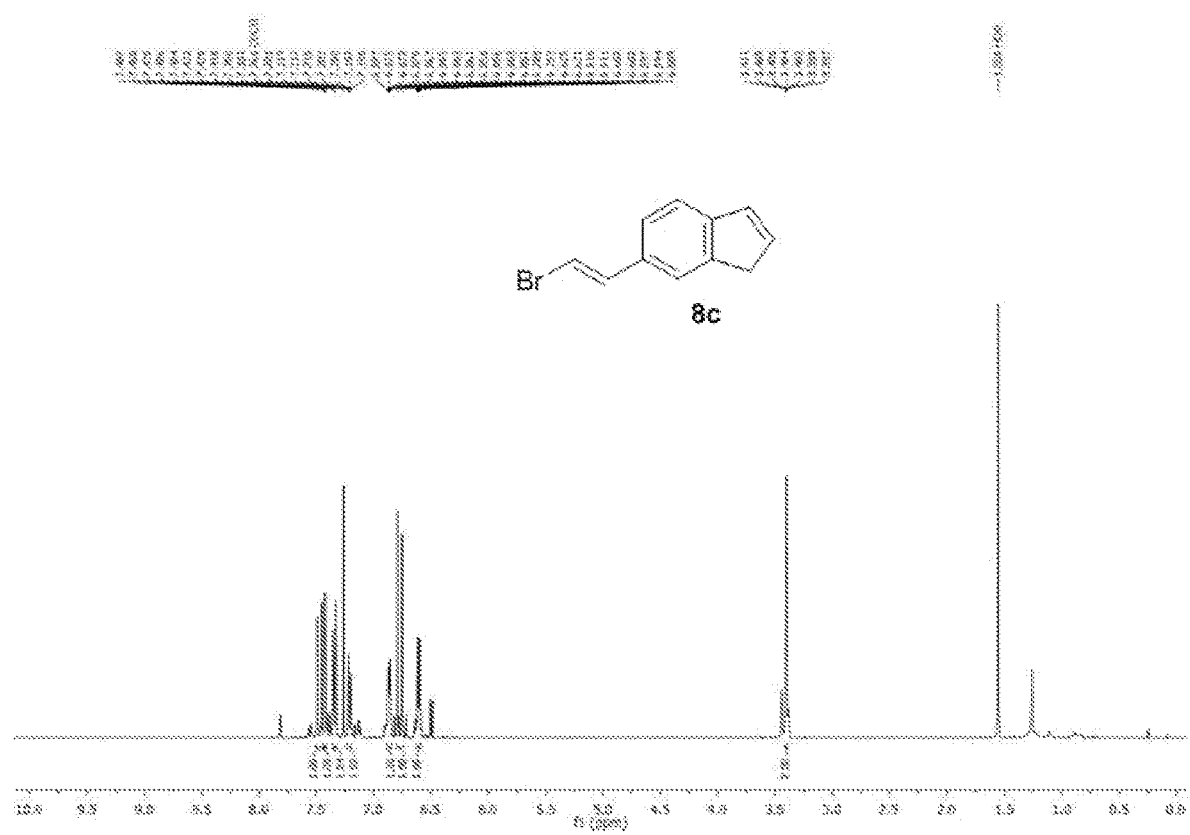
FIGS. 16A-16B show $^1$H NMR and $^{13}$C NMR spectra of compound 8c in CDCl$_3$.
Figure 16B:
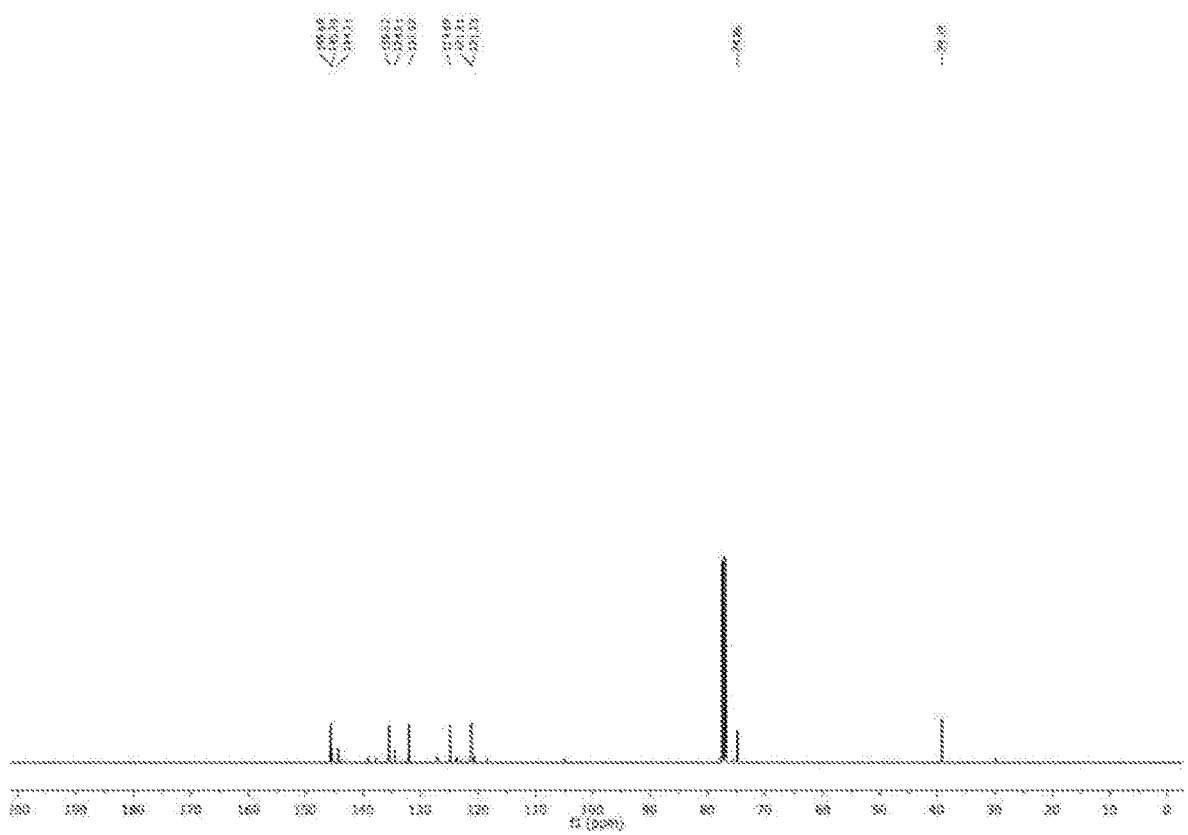

(E)-6-(2-Bromovinyl)indene (8c). Treatment of 6-iodoindene 6c (100 mg, 0.41 mmol) with trans-1,2-bis(tri-n-butyl-stannyl)ethylene and NBS by Procedure E (column chromatography; n-hexane) gave 8c (64 mg, 70%) (FIG. 16): $^1$H NMR (600 MHz, CDCl$_3$) δ 3.40-3.41 (m, 2H), 6.59-6.63 (m, 1H), 6.77 (d, J=14.8 Hz, 1H),), 6.85-6.88 (m, 1H), 7.19-7.22 (m, 1H), 7.34 (d, J=7.6 Hz, 1H), 7.42-7.43 (m, 1H), 7.47 (d, J=14.8 Hz, 1H); $^{13}$C NMR (101 MHz, CDCl$_3$) δ 39.19, 74.86. 121.13, 121.31, 124.88, 131.97, 134.51, 135.52, 144.31, 145.39, 145.60; HRMS (TOF, APCI) m/z calcd for C$_{11}$H$_8$$^{79}$Br 218.9815 [M−]$^−$, found 218.9814.

Figure 17A:
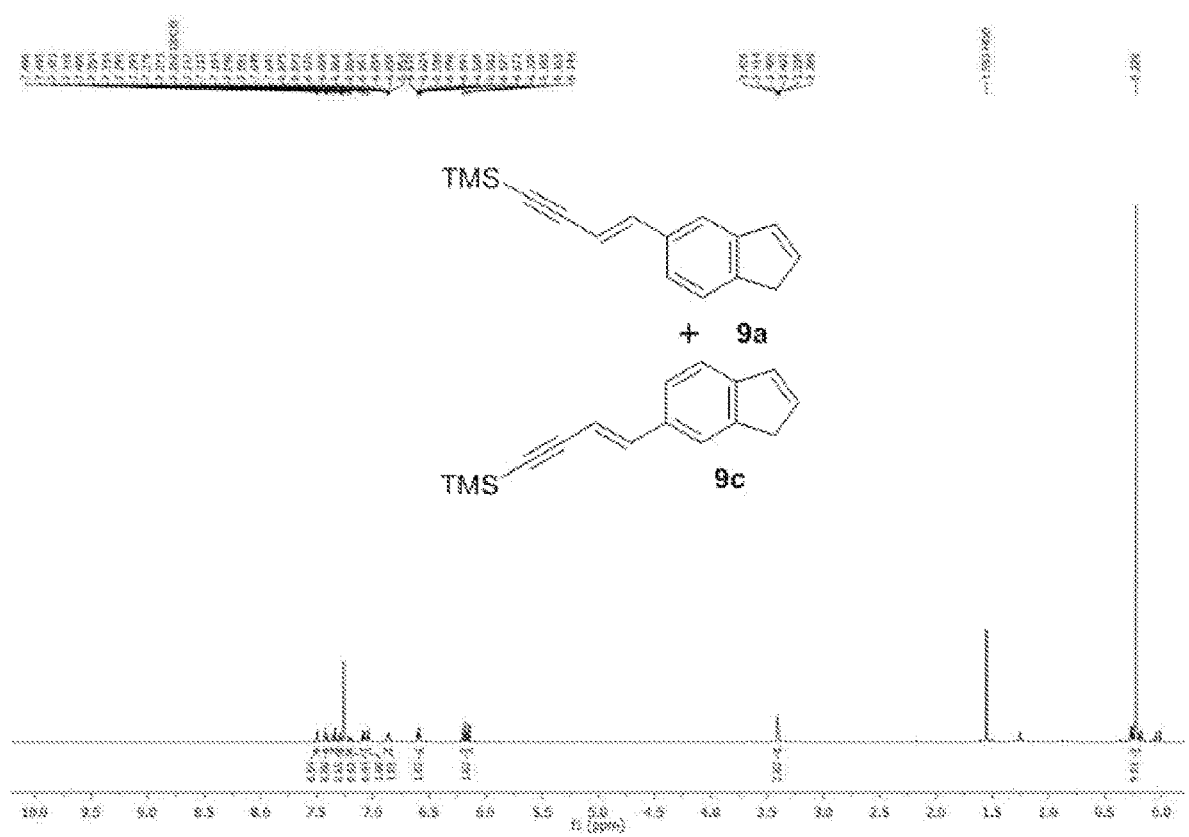
FIGS. 17A-17B show $^1$H NMR and $^{13}$C NMR spectra of mixture of 9a+9c in CDCl$_3$.
Figure 17B:
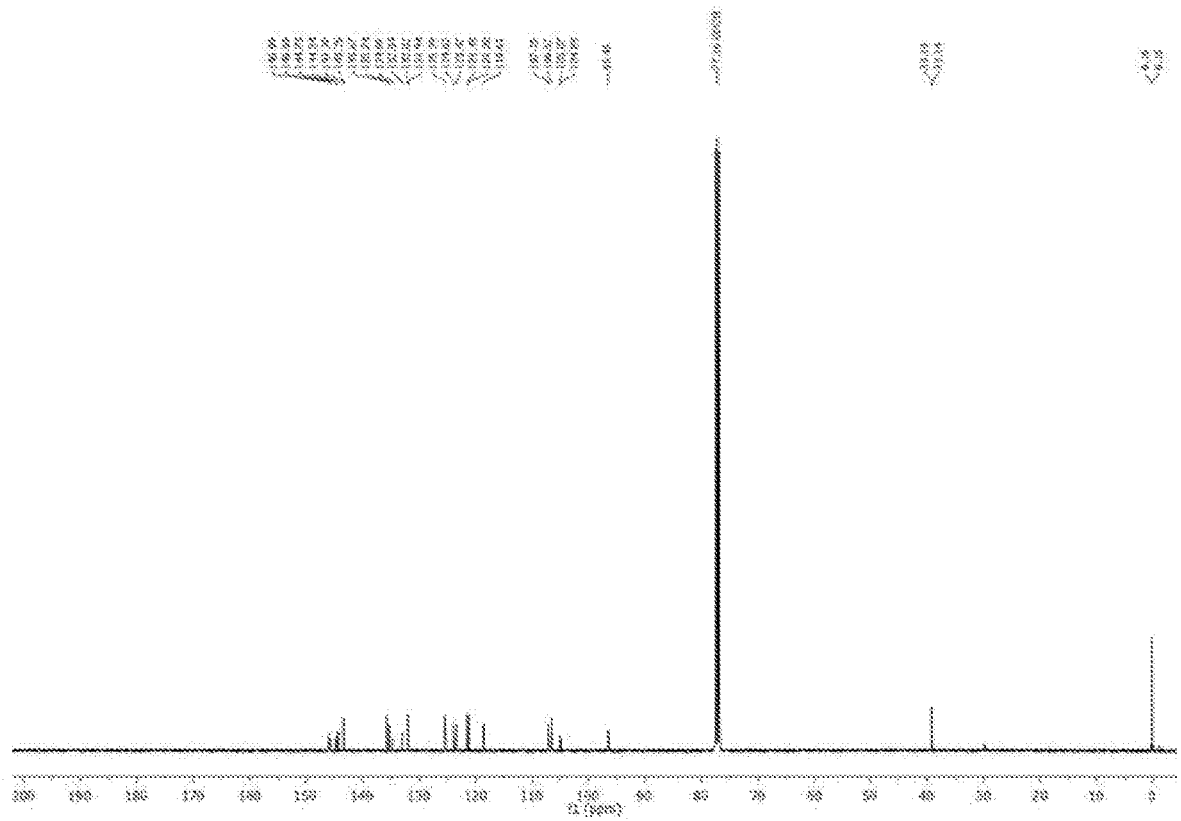

(E)-5-(But-1-en-3-yn-1-yl)indene (10a) and (E)-6-(But-1-en-3-yn-1-yl)indene (10c). Procedure F. (Step a) Pd(PPh$_3$)$_2$Cl$_2$ (31.7 mg, 0.04 mmol) and Cu(I)I (17.2 mg, 0.08 mmol) were added to dry Et$_3$N (5 mL) in a flame-dried flask equipped with a stirring bar under N$_2$ at rt. Then 8a (250 mg, 1.13 mmol) was added followed by TMS-acetylene (322 μL, 222.0 mg, 2.26 mmol). The resulting mixture was stirred for 1 h at rt [progress of the reaction was monitored by TLC (n-hexane)]. Volatiles were evaporated and the residue was purified by column chromatography (0→5% EtOAc/hexane) to give an inseparable mixture of (E)-5-[4-(trimethylsilyl)but-1-en-3-yn-1-yl]indene 9a and (E)-6-[4-(trimethylsilyl)but-1-en-3-yn-1-yl]indene 9c as light yellow liquid (245 mg, 91%; 1:1.5) (FIG. 17): $^1$H NMR (400 MHz, CDCl$_3$) δ 0.23 (s, 9H), 3.39-3.43 (m, 2H), 6.16 (d, J=16.4 Hz, 0.6H), 6.19 (d, J=16.4 Hz, 0.4H), 6.59 (tt, J=5.6, 2.0 Hz, 1H), 6.85-6.88 (m, 1H), 7.06 (d, J=16.0 Hz, 0.6H), 7.07 (d, J=16.4 Hz, 0.4H), 7.19-7.22 (m, 0.4H), 7.27-7.30 (m, 0.6H), 7.34 (d, J=7.8 Hz, 0.6H), 7.41 (d, J=7.4 Hz, 0.4H), 7.41 (d, J=0.8 Hz, 0.4H), 7.50 (d, J=0.8 Hz, 0.6H); $^{13}$C NMR (101 MHz, CDCl$_3$) δ 0.15, 0.16, 39.14, 39.19, 94.46, 104.89, 105.07, 106.57, 107.15, 118.61, 121.20, 121.49, 123.47, 124.02, 125.39, 131.94, 132.02, 132.94, 134.66, 135.24, 135.67, 143.25, 143.30, 144.34, 144.73, 145.59, 145.99.

Figure 18A:
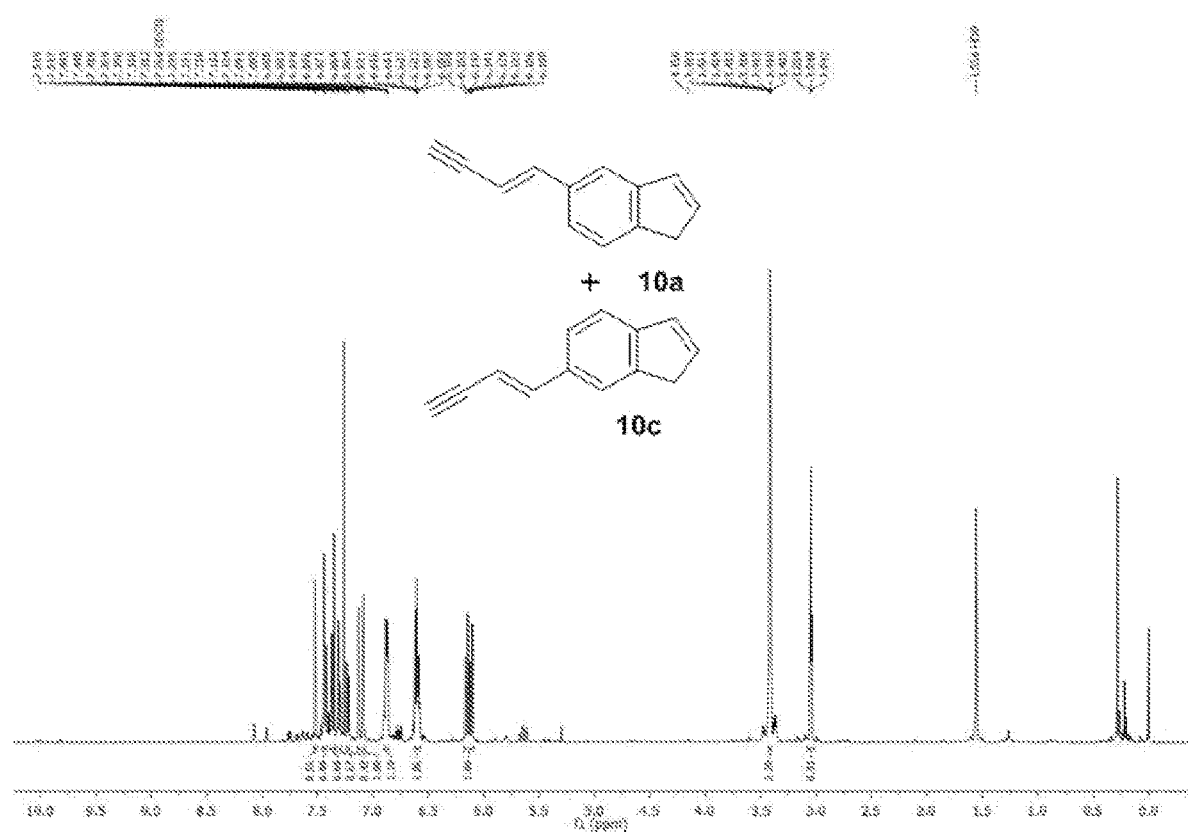
FIGS. 18A-18B show $^1$H NMR and $^{13}$C NMR spectra of mixture of 10a+10c in CDCl$_3$.
Figure 18B:
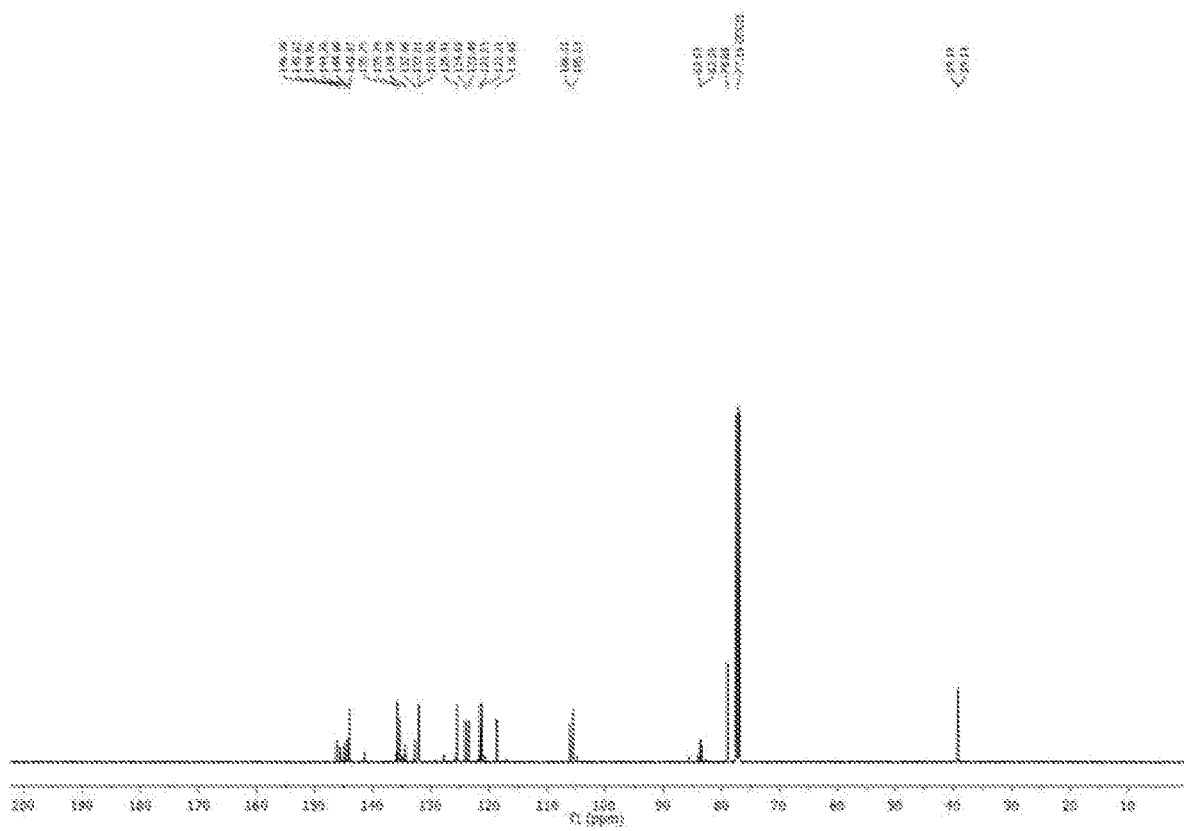

(Step b) Anhydrous K$_2$CO$_3$ (200 mg, 1.45 mmol) was added to a stirred solution of mixture of 9a and 9c (230 mg, 0.96 mmol) in dry MeOH/DCM (10 mL, 1:1) at room temperature. After 30 min, volatiles were evaporated and the residue was column chromatographed (0→5% EtOAc/hexane) to give inseparable mixture of 10a and 10c as light yellow liquid (147.5 mg, 92%; 1:1.5) (FIG. 18): $^1$H NMR (400 MHz, CDCl$_3$) δ 3.05 (t, J=2.4 Hz, 1H), 3.40-3.43 (m, 2H), 6.12 (dd, J=16.4, 2.4 Hz, 0.6H), 6.15 (dd, J=16.4, 2.4 Hz, 0.4H), 6.60 (tt, J=5.6, 2.0 Hz, 1H), 6.86-6.89 (m, 1H), 7.10 (d, J=16.4 Hz, 0.6H), 7.11 (d, J=16.4 Hz, 0.4H), 7.22 (dd, J=7.6, 1.6 Hz, 0.4H), 7.30 (dd, J=8.0, 1.6 Hz, 0.6H), 7.36 (d, J=7.6 Hz, 0.7H), 7.43 (d, J=8.4 Hz, 0.8H), 7.52 (d, J=0.8 Hz, 0.5H); $^{13}$C NMR (101 MHz, CDCl$_3$) δ 39.14, 39.18, 78.88, 83.36, 83.53, 105.53, 106.11, 118.65, 121.21, 121.53, 123.49, 124.03, 125.41, 131.90, 132.01, 132.66, 134.39, 135.29, 135.75, 143.97, 144.00, 144.36, 144.86, 146.10, 145.62; HRMS (TOF, APCI) m/z calcd for C$_{13}$H$_{11}$ 167.0855 [M+H]$^+$, found 167.0855.

Subjection of 8c (32 mg, 0.14 mmol) to Procedure F also gave mixture of 10a and 10c (19.2 mg, 80%; 1:1.5) with identical spectroscopic data.

Figure 19A:
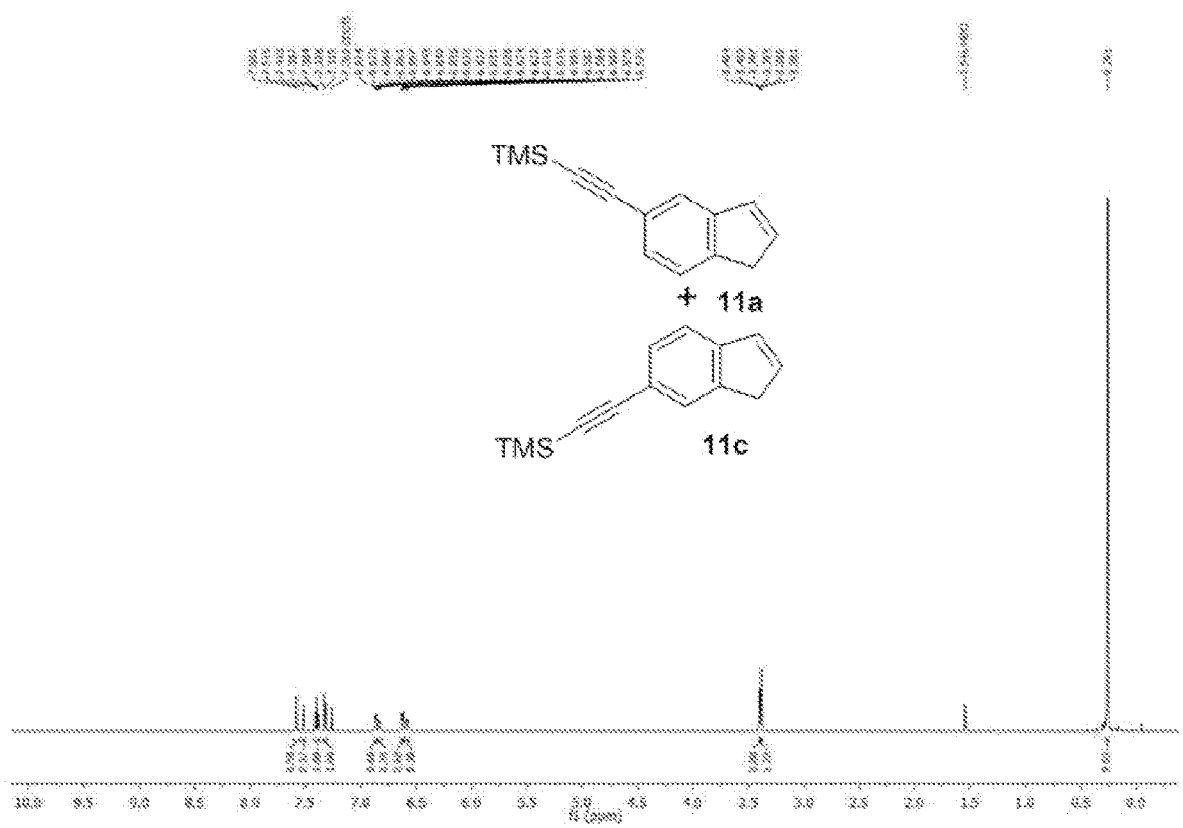
FIGS. 19A-19B show $^1$H NMR and $^{13}$C NMR spectra of mixture of 11a+11c in CDCl$_3$.
Figure 19B:
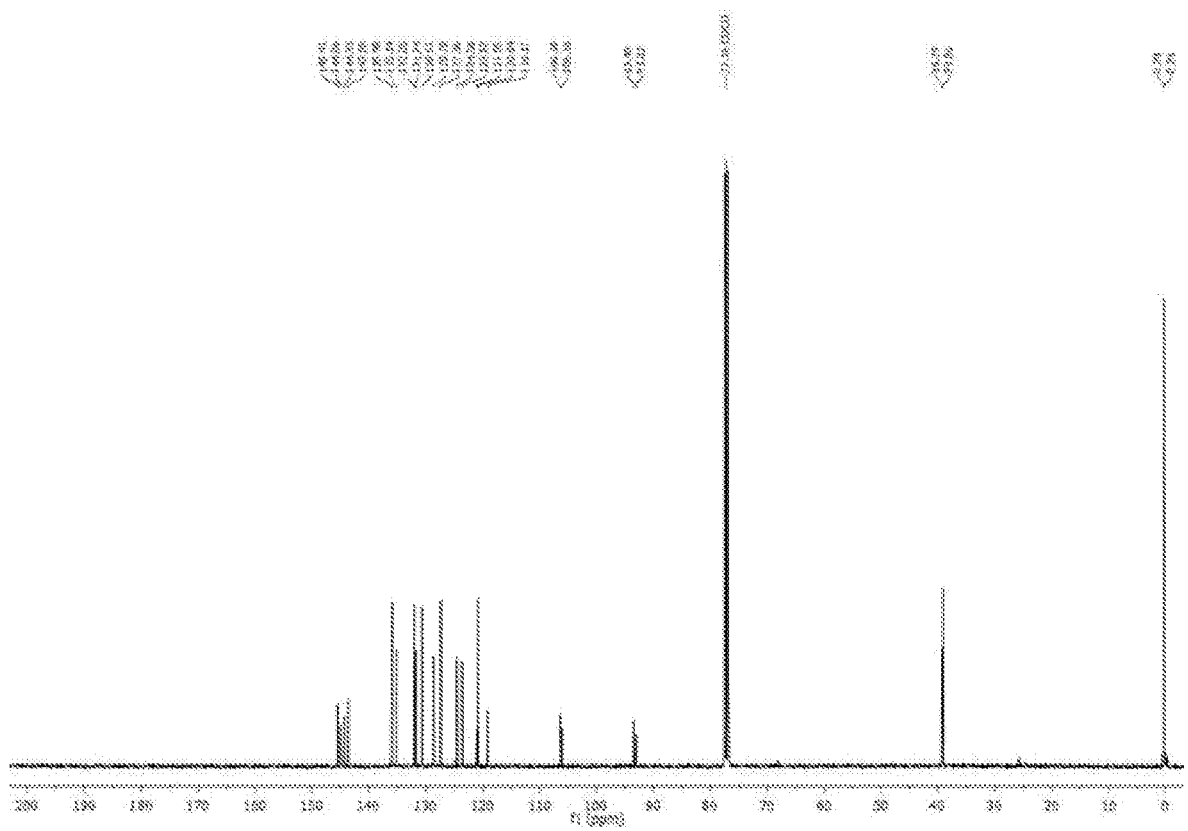

5-Ethynylindene (12a) and 6-Ethynylindene (12c). Treatment of 5-iodoindene 6a (400 mg, 1.65 mmol) with TMS-acetylene (470 μL, 324 mg, 3.3 mmol) and Pd(PPh$_3$)$_4$ by Procedure F (step a) gave a mixture of 5-[2-(trimethylsilyl)ethynyl]indene 11a and 6-[2-(trimethylsilyl)ethynyl]indene 11c as a light yellow liquid (315 mg, 90%; 1:1.5) (FIG. 19): $^1$H NMR (600 MHz, CDCl$_3$) δ 0.26 (s, 9H), 3.39 (t, J=2.2 Hz, 1.2H), 3.40 (t, J=2.2 Hz, 0.8H), 6.58 (dt, J=5.4, 1.8 Hz, 0.4H), 6.62 (dt, J=5.4, 1.8 Hz, 0.6H), 6.83-6.84 (m, 0.4H), 6.86-6.88 9 (m, 0.6H), 7.32 (d, J=7.8 Hz, 1H), 7.40 (t, J=7.8 Hz, 1H), 7.52 (s, 0.4H), 7.58 (s, 0.6H); $^{13}$C NMR (101 MHz, CDCl$_3$) δ 0.21, 0.23, 39.06, 39.29, 93.02, 93.40, 106.10, 106.38, 119.17, 102.84, 121.05, 123.62, 124.58, 127.36, 128.70, 130.61, 131.74, 132.05, 135.14, 135.90, 143.60, 144.33, 144.96, 145.41.

Figure 20A:
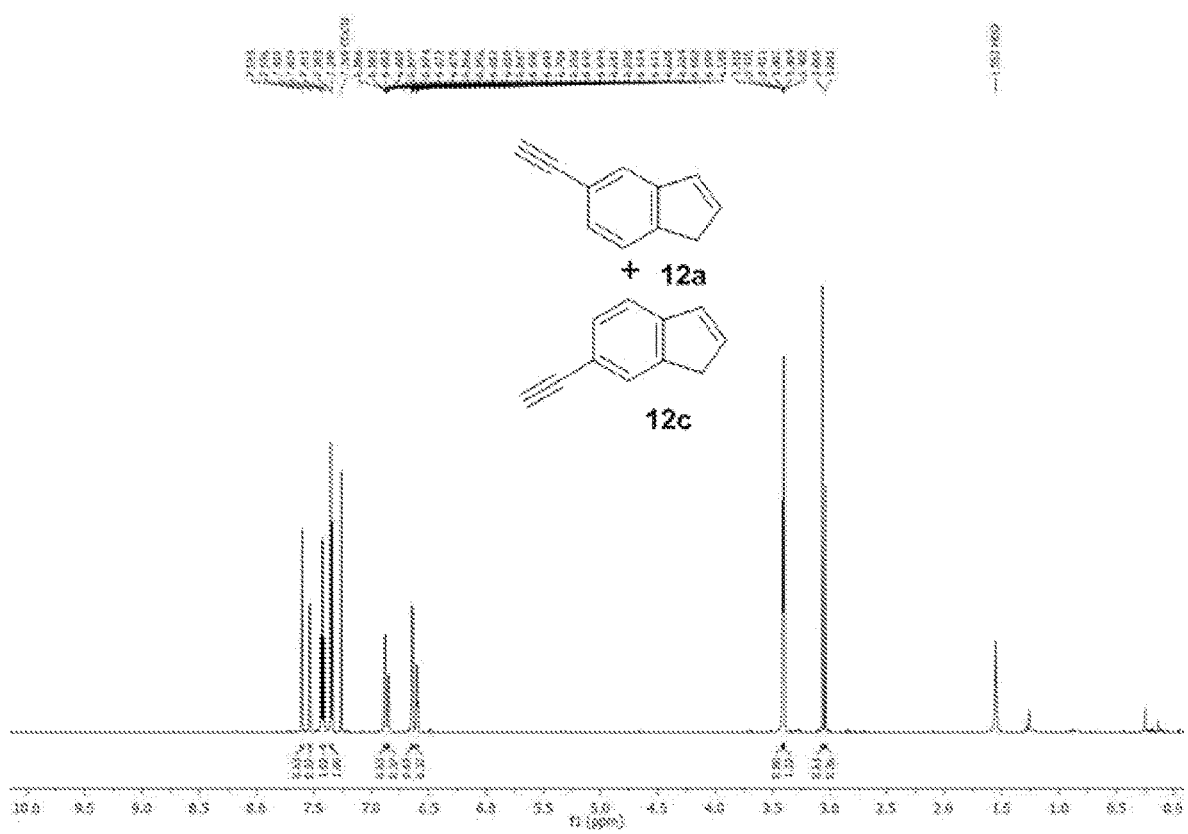
FIGS. 20A-20B show $^1$H NMR and $^{13}$C NMR spectra of mixture of 12a+12c in CDCl$_3$.
Figure 20B:
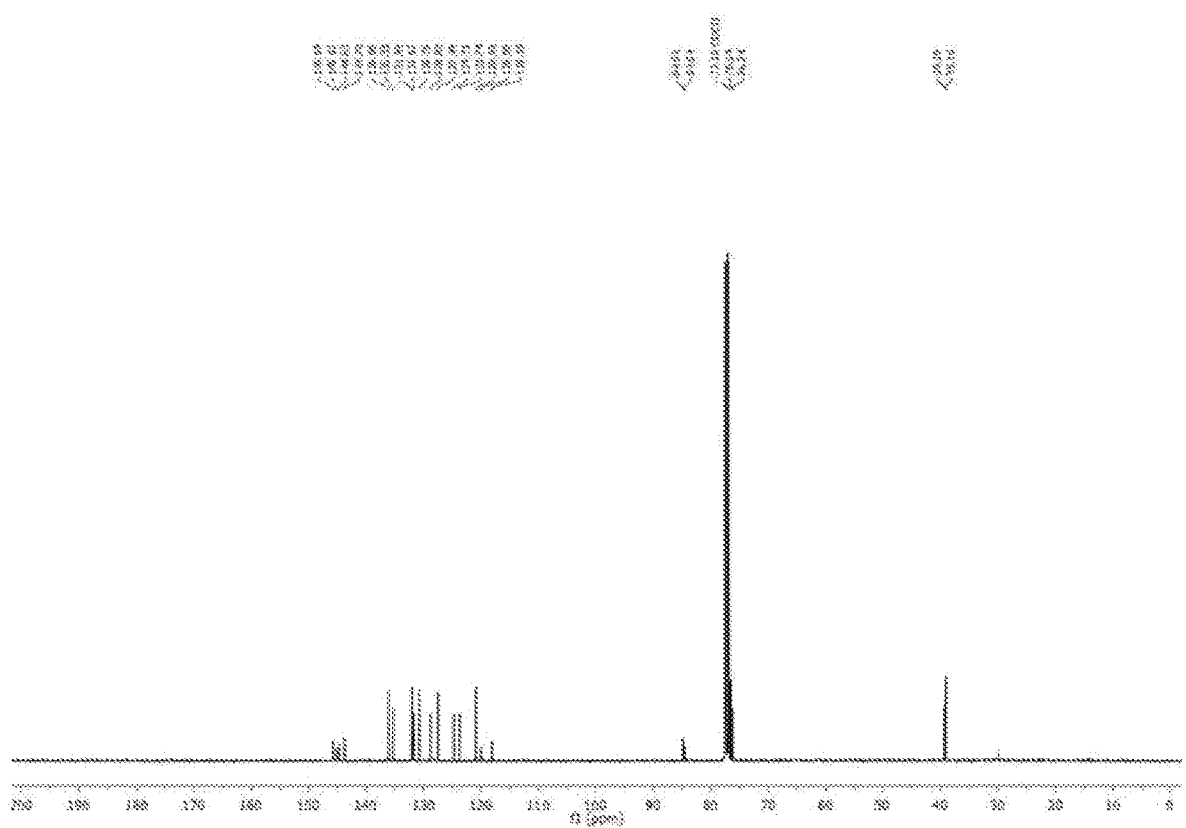

Treatment of the mixture of 11a and 11c (300 mg, 1.41 mmol) with anhydrous K$_2$CO$_3$ (293 mg, 2.12 mmol) by Procedure F (step b) gave a mixture of 12a and 12c as light yellow liquid (178 mg, 90%; 1:1.7) (FIG. 20): $^1$H NMR (600 MHz, CDCl$_3$) δ 3.04 (s, 0.39H), 3.07 (s, 0.61H), 3.40 (t, J=2.4 Hz, 1.22H), 3.42 (t, J=2.2 Hz, 0.80H), 6.60 (dt, J=5.4, 2.4 Hz, 0.37H), 6.64 (dt, J=5.4, 2.4 Hz, 0.63H), 6.84-6.86 (m, 0.37H), 6.87-6.89 (m, 0.63H), 7.35 (d, J=7.8 Hz, 1H), 7.42 (t, J=7.8 Hz, 1H), 7.54 (s, 0.37H), 7.60 (s, 0.63H); $^{13}$C NMR (101 MHz, CDCl$_3$) δ 39.10, 39.30, 76.24, 76.54, 84.54, 84.81, 118.10, 120.00, 120.93, 123.74, 124.71, 127.49, 128.82, 130.76, 131.67, 131.99, 135.33, 136.06, 143.70, 144.63, 145.07, 145.69; HRMS (TOF, APCI) m/z calcd for C$_{11}$H$_9$ 141.0699 [M+H]$^+$, found 141.0699.

Subjection of 6c (200 mg, 0.83 mmol) by Procedure F gave also mixture of 12a and 12c (89 mg, 92%; 1:1.7) with identical spectroscopic data.

Figure 21A:
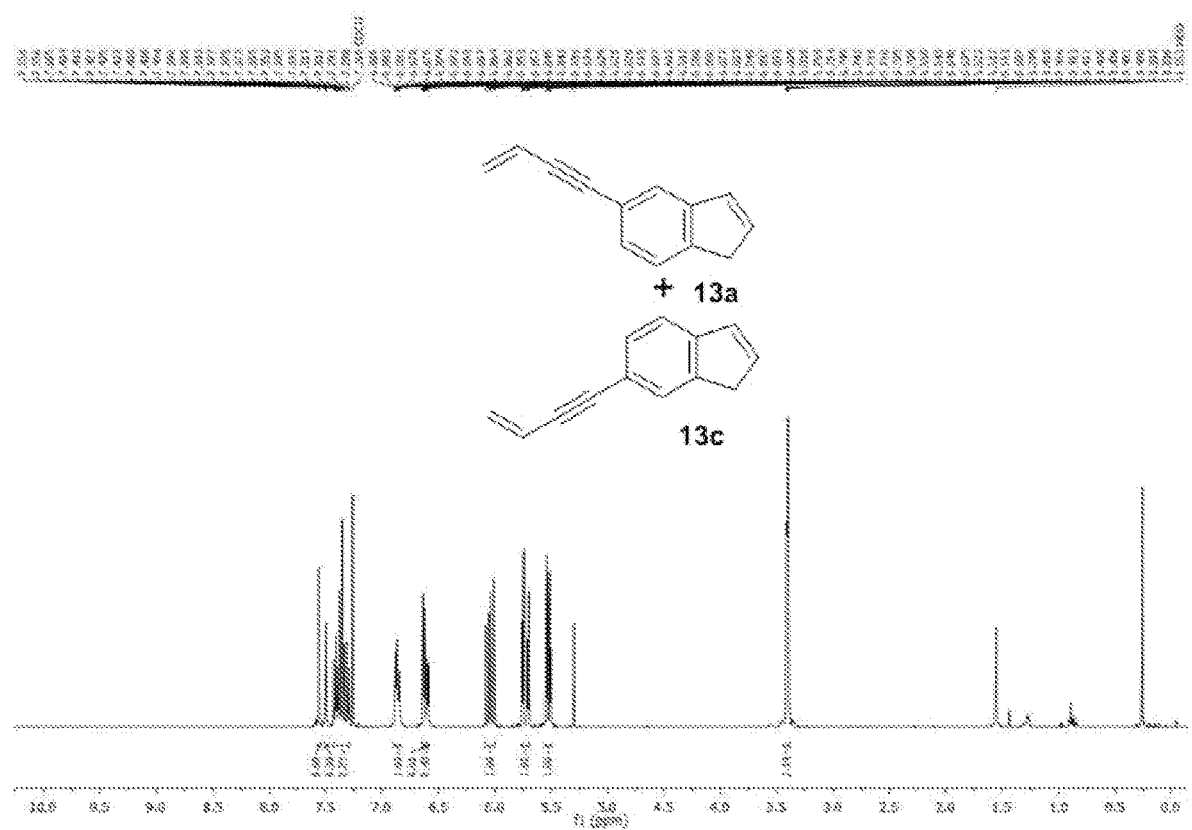
FIGS. 21A-21B show $^1$H NMR and $^{13}$C NMR spectra of mixture of 13a+13c in CDCl$_3$.
Figure 21B:
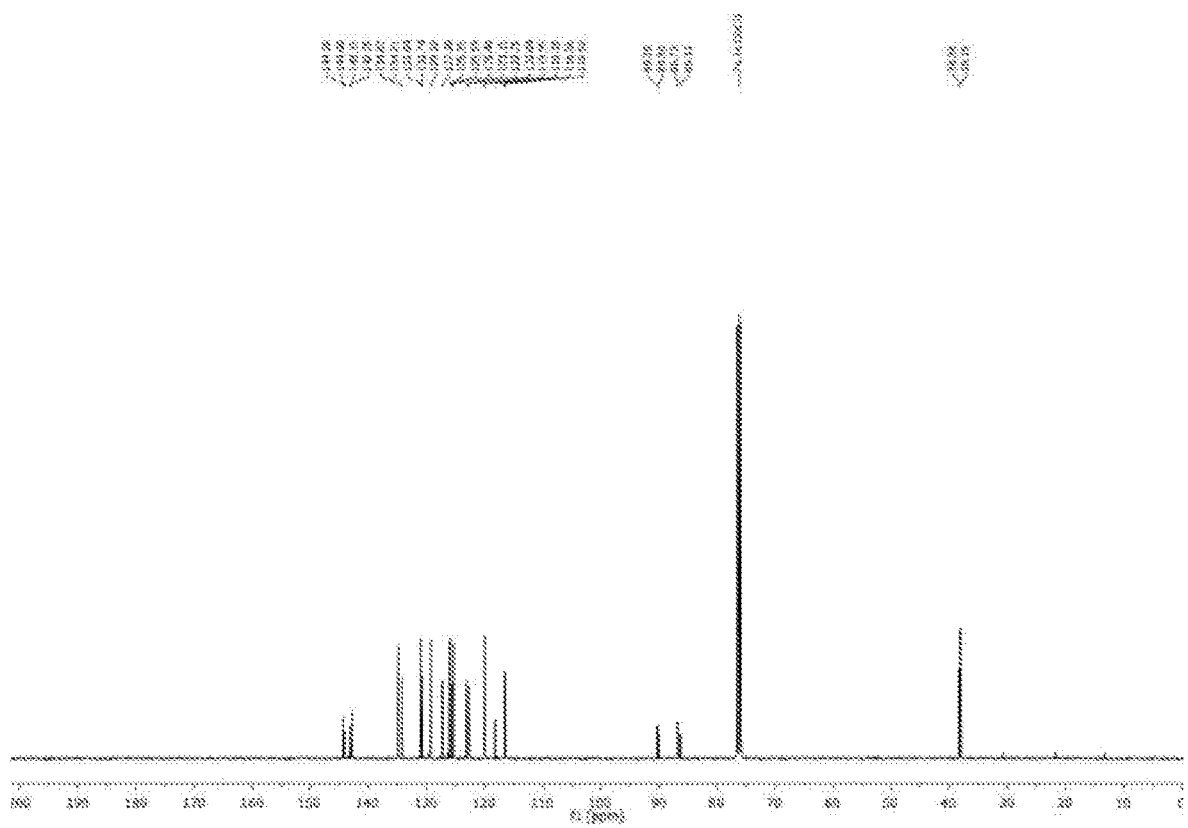

5-(But-3-en-1-yn-1-yl)indene (13a) and 6-(But-3-en-1-yn-1-yl)indene (13c). Pd(PPh$_3$)$_4$ (37.1 mg, 0.032 mmol) and Cu(I)I (12.2 mg, 0.064 mmol) were placed in the flame-dried flask under N$_2$ at 0° C. (ice-bath). Then dry Et$_3$N (5 mL) and vinyl bromide (1.0 M in THF; 1.4 mL, 1.4 mmol) were added following by slow addition of mixture of 12a and 12c (150 mg, 1.07 mmol) dissolved in dry Et$_3$N (2 mL) via a syringe pump (over 3 h). The resulting mixture was allowed to warm up to ambient temperature (30 min) and was stirred for another 2 h. Volatiles were evaporated and the residue was purified by column chromatography (hexane) to give mixture of 13a and 13c as light yellow liquid (125 mg, 70%) (FIG. 21): $^1$H NMR (400 MHz, CDCl$_3$) δ 3.40-3.42 (m, 2H), 5.53 (dd, J=11.2, 2.0 Hz, 0.6H), 5.54 (dd, J=11.2, 2.0 Hz, 0.4H), 5.72 (dd, J=17.2, 2.0 Hz, 0.6H), 5.74 (dd, J=17.6, 2.0 Hz, 0.4H), 6.04 (dd, J=17.6, 11.2 Hz, 0.4H), 6.09 (dd, J=17.6, 11.2 Hz, 0.6H), 6.60 (dt, J=5.6, 2.0 Hz, 0.4H), 6.63 (dt, J=5.6, 2.0 Hz, 0.6H), 6.84-6.89 (m, 1H), 7.29-7.43 (m, 2H), 7.49 (d, J=0.8 Hz, 0.4H), 7.54-7.57 (m, 0.6H); $^{13}$C NMR (101 MHz, CDCl$_3$) δ 38.10, 38.28, 86.31, 86.73, 89.90, 90.20, 116.52, 116.56, 118.18, 119.95, 120.04, 122.75, 123.15, 125.40, 125.59, 125.95, 127.30, 129.22, 130.74, 131.04, 134.21, 134.82, 142.75, 143.15, 144.28, 144.08; HRMS (TOF, APCI) m/z calcd for C$_{13}$H$_{11}$ 167.0855 [M+H]$^+$, found 167.0856.

Figure 22A:
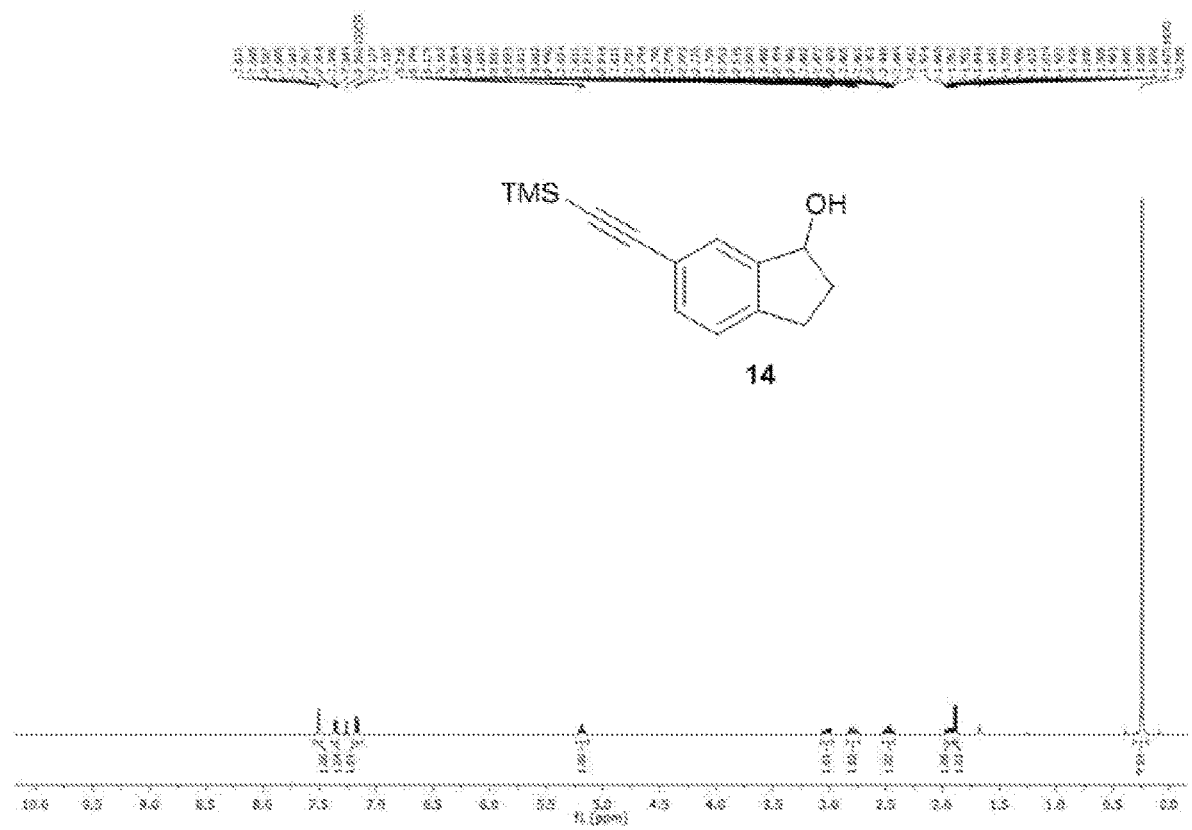
FIGS. 22A-22B show $^1$H NMR and $^{13}$C NMR spectra of compound 14 in CDCl$_3$.
Figure 22B:
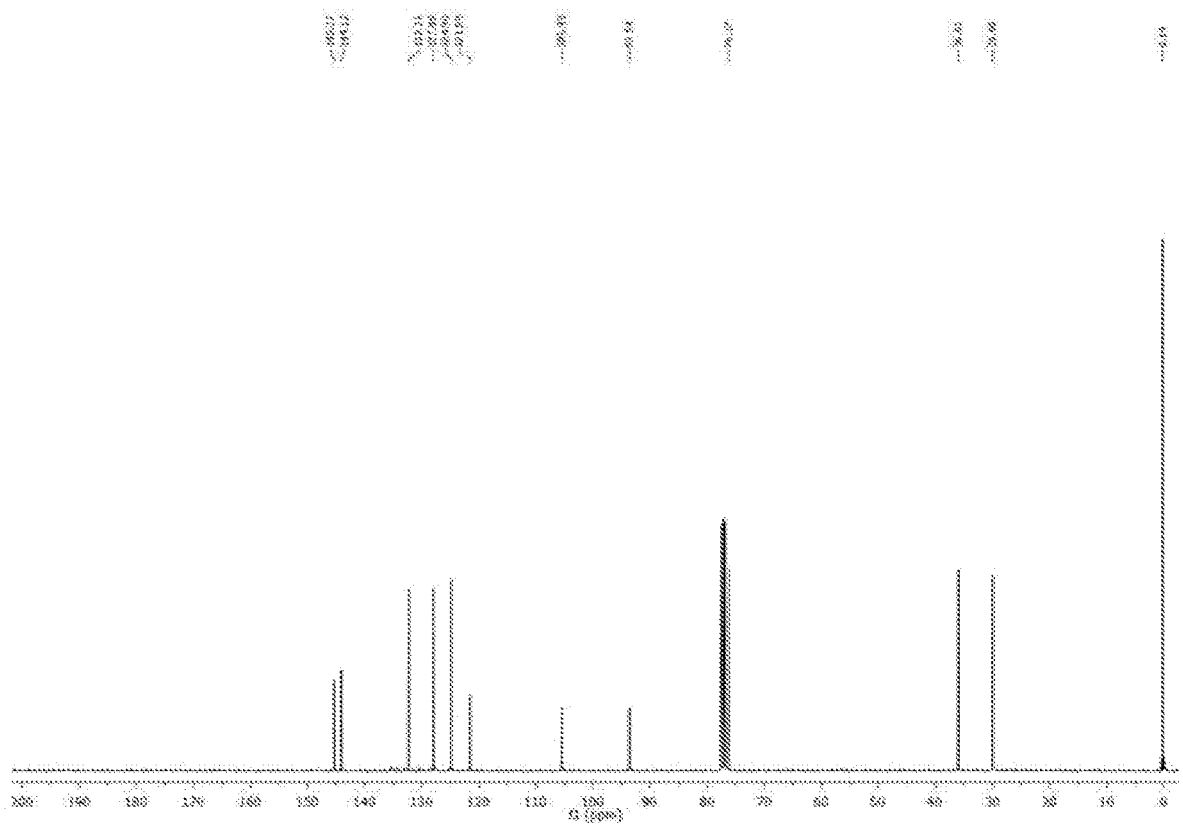

6-Ethynylindan-1-ol (15). Treatment of 5a (40 mg, 0.194 mmol) with TMS-acetylene (55 µL, 38 mg, 0.39 mmol) and Pd(PPh$_3$)$_4$ by Procedure F (step a; column chromatography (10→20% EtOAc/hexane)) gave 14 (40 mg, 90%) as light yellow gummy solid (FIG. 22): $^1$H NMR (400 MHz CDCl$_3$) δ 0.24 (s, 9H), 1.89 (d, J=6.8 Hz, 1H), 1.90-1.98 (m, 1H), 2.42-2.52 (m, 1H), 2.74-2.85 (m, 1H), 3.03 (ddd, J=16.4, 8.4, 4.8 Hz, 1H), 5.19 (q, J=6.4 Hz, 1H), 7.17 (d, J=8.0 Hz, 1H), 7.36 (dd, J=8.0, 1.6 Hz, 1H), 7.50-7.52 (m, 1H); $^{13}$C NMR (101 MHz, CDCl$_3$) δ 0.14, 29.98, 36.01, 76.17, 93.54, 105.49, 121.59, 124.90, 127.98, 132.21, 144.12, 145.27.

Figure 23A:
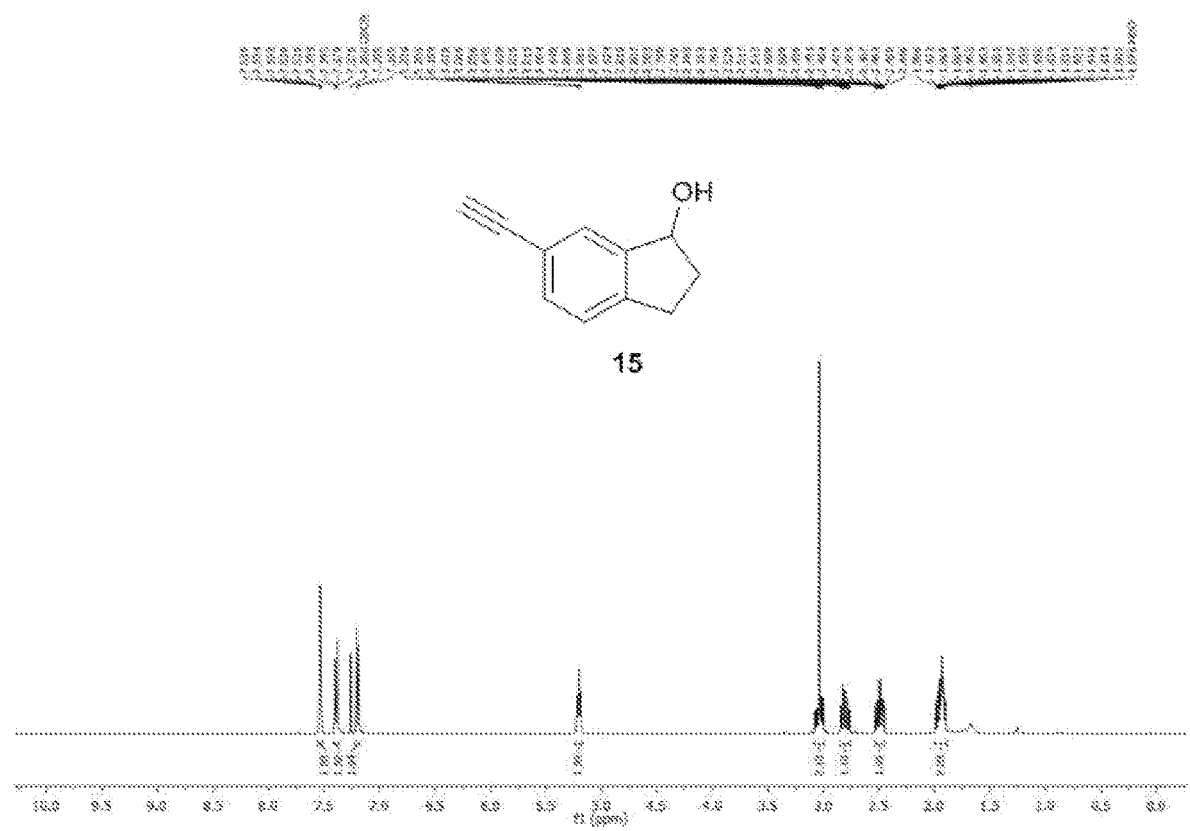
FIGS. 23A-23B show $^1$H NMR and $^{13}$C NMR spectra of compound 15 in CDCl$_3$.
Figure 23B:
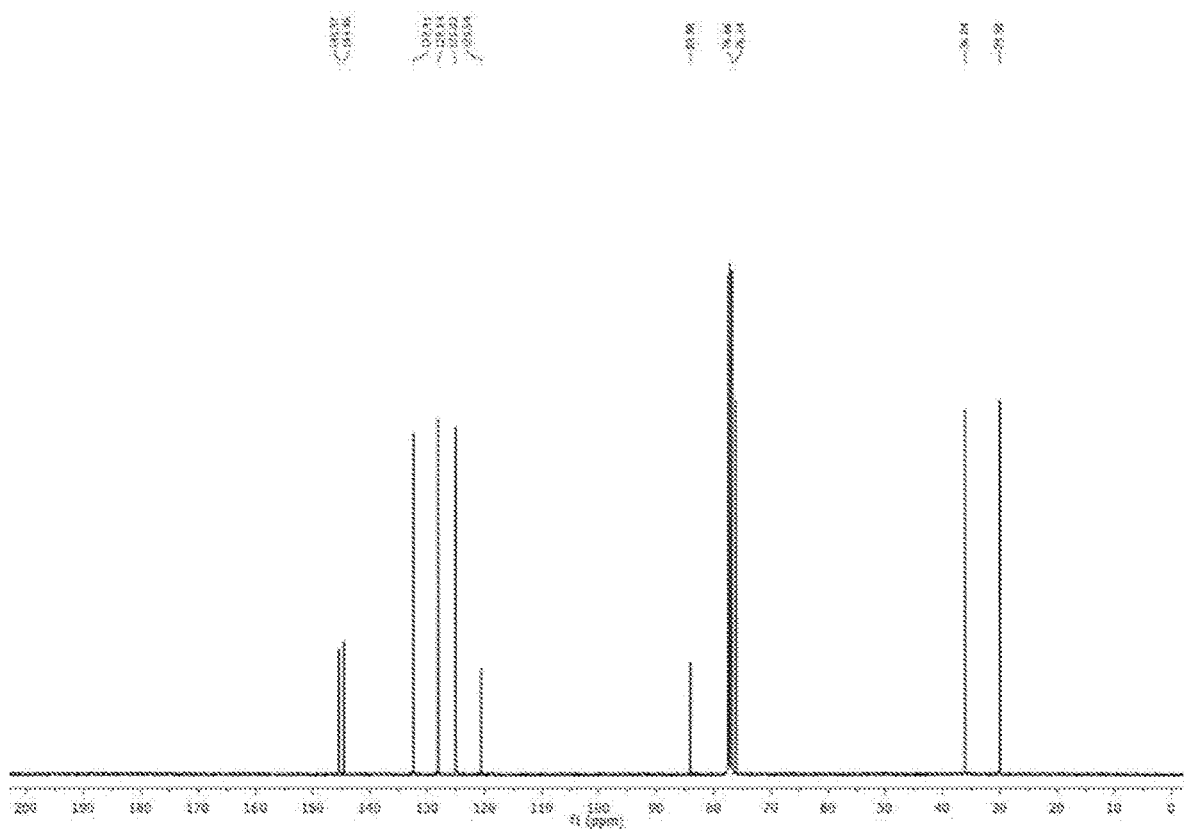

Treatment of 14 (40 mg, 0.174 mmol) with anhydrous K$_2$CO$_3$ (96 mg, 0.7 mmol) by Procedure F (step b; column chromatography (20→30% EtOAc/hexane))) gave 15 as pale yellow solid (26 mg, 95%) (FIG. 23): $^1$H NMR (400 MHz, CDCl$_3$) δ 1.90-1.99 (m, 2H), 2.45-2.53 (m, 1H), 2.76-2.86 (m, 1H), 3.00-3.08 (m, 2H), 5.20 (t, J=6.4 Hz, 1H), 7.20 (d, J=8.0 Hz, 1H), 7.39 (dd, J=8.0, 1.6 Hz, 1H), 7.51-7.55 (m, 1H); $^{13}$C NMR (101 MHz, CDCl$_3$) δ 29.98, 36.04, 76.14, 76.66, 83.98, 120.54, 125.03, 128.14, 132.41, 144.46, 145.37; HRMS (TOF, ESI) m/z calcd for C$_{11}$H$_9$ 141.0699 [M−H$_2$O+H]$^+$, found 141.0693.

Figure 24A:
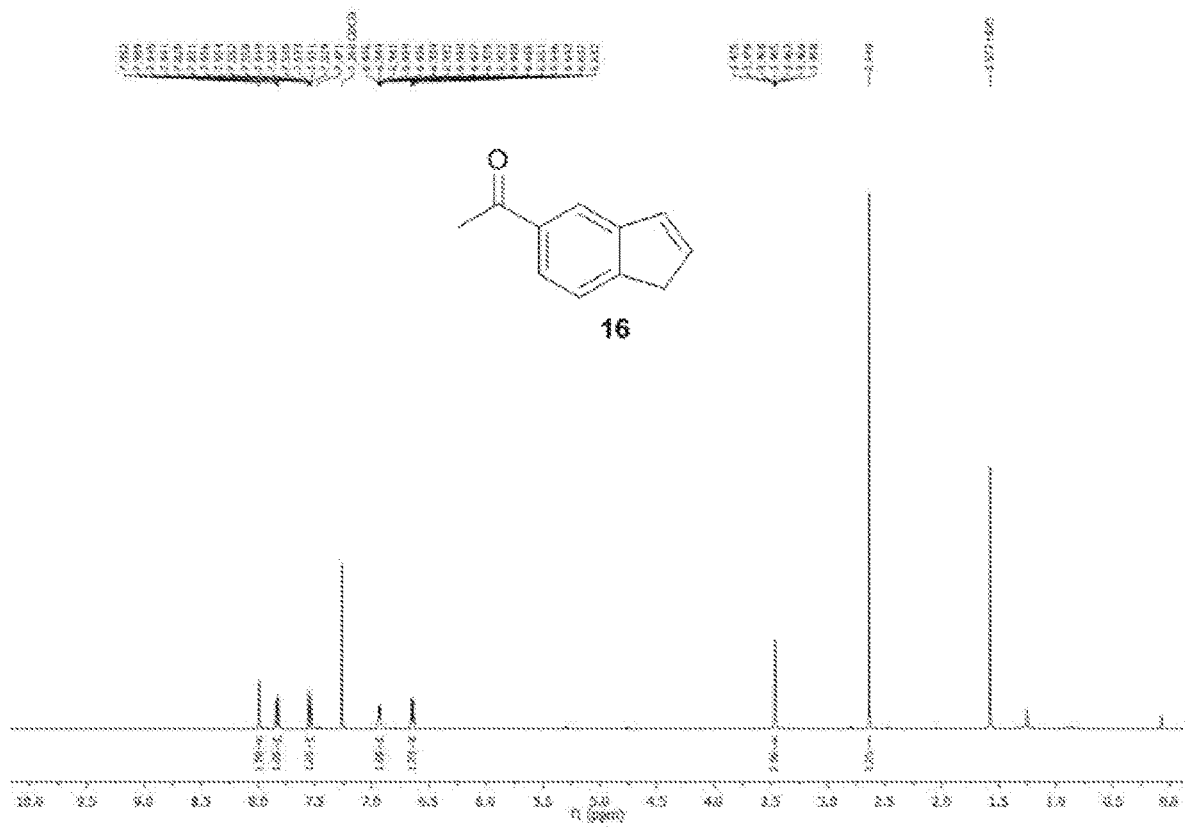
FIGS. 24A-24B show $^1$H NMR and $^{13}$C NMR spectra of compound 16 in CDCl$_3$.
Figure 24B:
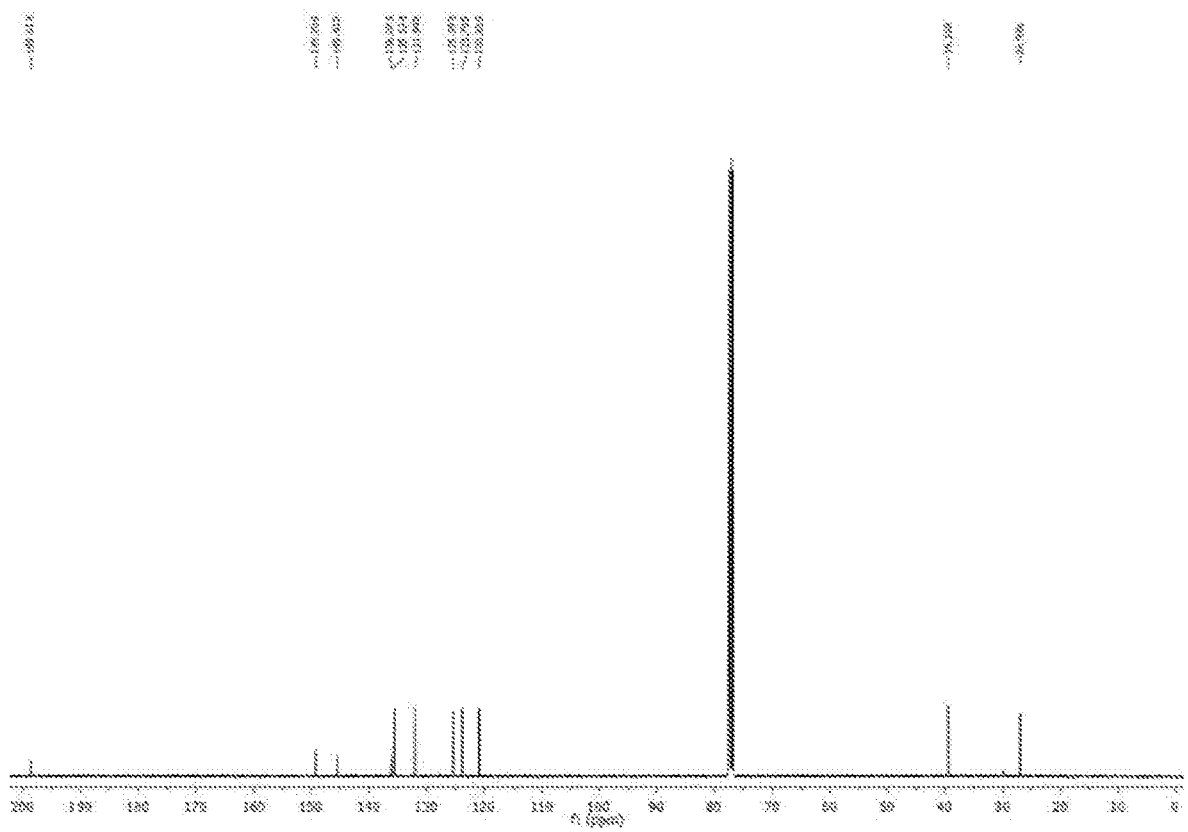
Figure 25A:
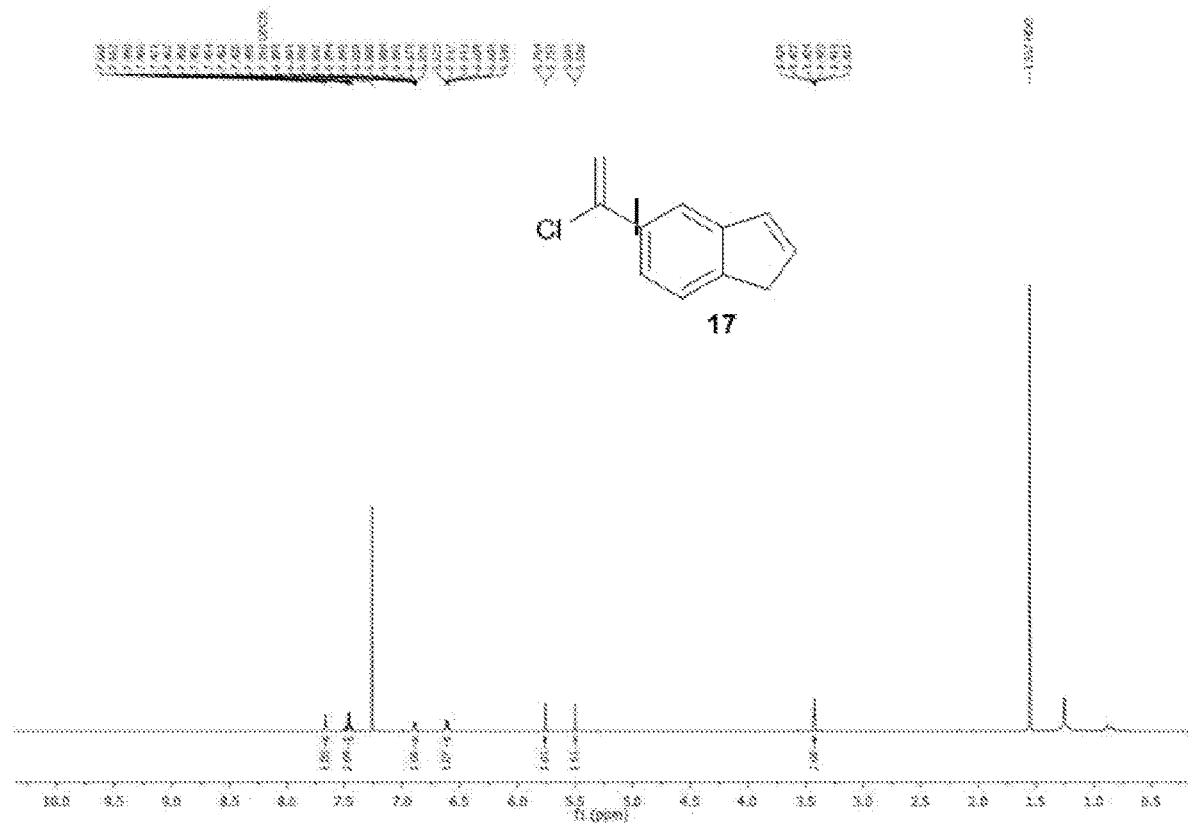
FIGS. 25A-25B show $^1$H NMR and $^{13}$C NMR spectra of compound 17 in CDCl$_3$.
Figure 25B:
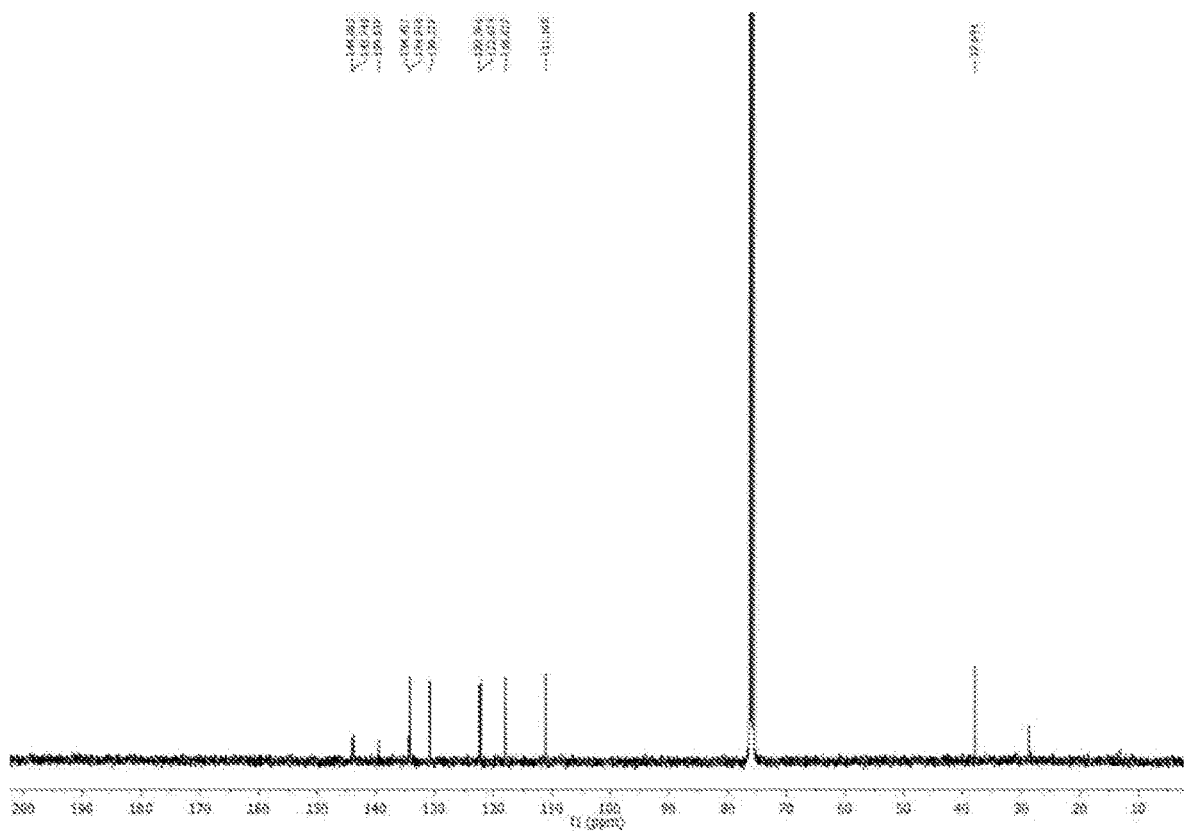

5-Acetylindene (16) and 6-(1-Chlorovinyl)indene (17). The alcohol 15 (10 mg, 0.06 mmol) was dissolved in THF/H$_2$O (4 mL, 1:1). Aqueous 6 N HCl (200 µL, 1.2 mmol) was then added and the reaction mixture was refluxed at 105° C. for 12 h. The reaction mixture was concentrated under vacuum to approximately 2 mL and extracted with EtOAc. The organic phase was separated, dried over anhydrous Na$_2$SO$_4$, filtered, and evaporated at reduced pressure. The residue was purified by column chromatography (5→10% EtOAc/ hexane) to give 16 (6 mg, 63%) (FIG. 24) and 17 (2.5 mg, 24%) (FIG. 25) as white solids. The more polar 16 had: $^1$H NMR (400 MHz, CDCl$_3$) δ 2.64 (s, 3H), 3.46 (td, J=2.0, 0.8 Hz, 2H), 6.63-6.66 (m, 1H), 6.92-6.95 (m, 1H), 7.54 (dp, J=7.6, 0.8 Hz, 1H), 7.83 (dd, J=8.0, 1.6 Hz, 1H), 7.99 (d, J=1.2 Hz, 1H); $^{13}$C NMR (101 MHz, CDCl$_3$) δ 26.99, 39.39, 120.85, 123.80, 125.39, 131.95, 135.53, 136.07, 145.44, 149.21, 198.61; HRMS (TOF, DART) m/z calcd for C$_{11}$H$_{11}$O 159.0804 [M+H]$^+$, found 159.0808. The less polar 17 had: $^1$H NMR (400 MHz, CDCl$_3$) δ 3.41-3.43 (m, 2H), 5.50 (d, J=1.6 Hz, 1H), 5.76 (d, J=2.0 Hz, 1H), 6.59-6.63 (m, 1H), 6.88-6.90 (m, 1H), 7.43-7.50 (m, 2H), 7.66 (d, J=1.2 Hz, 1H); $^{13}$C NMR (101 MHz, CDCl$_3$) δ 37.89, 111.10, 118.03, 112.07, 123.37, 130.78, 134.22, 134.46, 139.54, 143.75, 144.08; HRMS (TOF, APCI) m/z calcd for C$_{11}$H$_8^{35}$Cl 175.0320 [M−H]$^−$, found 175.0390.

Example 1—Synthesis of 5-iodoindene 6a and 7-iodoindene 6b

Figure 26:
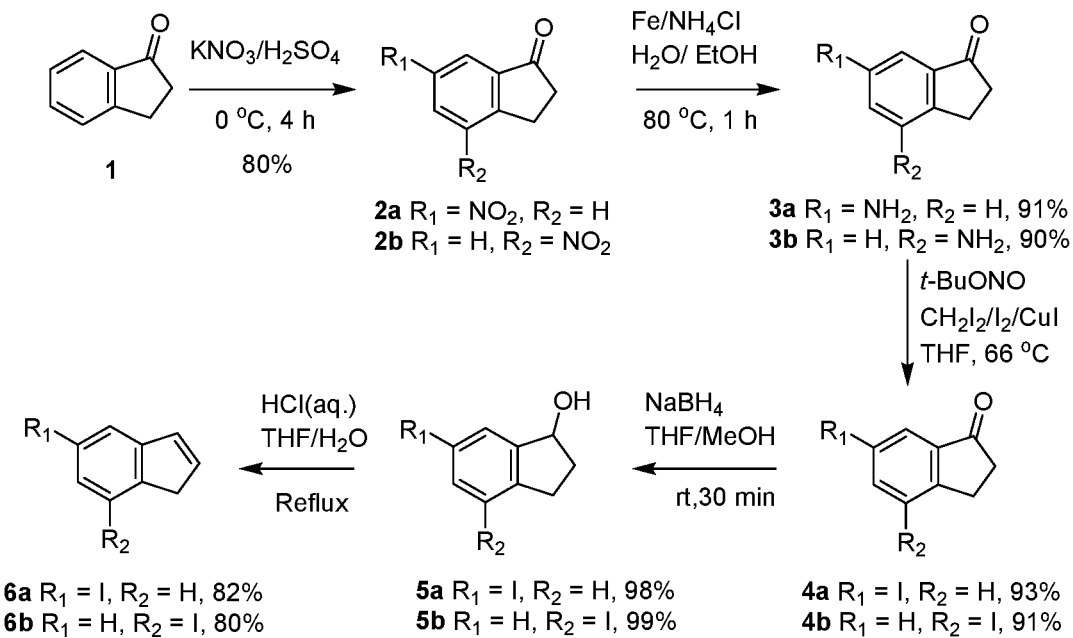
FIG. 26 shows the synthesis of 5-iodoindene 6a and 7-iodoindene 6b.

Electrophilic nitration of indan-1-one 1 with KNO$_3$/H$_2$SO$_4$ afforded separable mixture of 6-nitro- 2a and 4-nitroindan-1-one 2b (80%, 4:1 ratio; FIG. 26). Selective reduction 2a or 2b with Fe powder/NH$_4$Cl gave 6-amino- 3a and 4-aminoindan-1-one 3b in excellent yield. Subsequent, diazotization-iodination of 3a or 3b with t-BuONO/CH$_2$I$_2$/I$_2$/CuI afforded 6-iodo- 4a and 4-iodoindanones 4b (>90%) in addition to diiodo substituted by-products (~4%). Reduction of 4a or 4b with NaBH$_4$ provided secondary alcohols 5a and 5b (>98%). Subsequent dehydration with aqueous HCl in THF/H$_2$O yielded selectively 5- and 7-iodoindenes, 6a and 6b (>80%). Isomerization to different indene isomers was not observed during this reaction sequence. It is noteworthy that dehydration of 5a or 5b with p-toluenesulfonic acid in refluxed toluene, used successfully for dehydration of the corresponding nitroindanoles, failed to produce expected iodoindenes. This general method allows preparation of expensive 5-iodoindene and unreported 7-iodoindene in high yields utilizing readily available and cost-effective reagents.

Example 2—Synthesis of 6-iodoindene 6c

Figure 27:
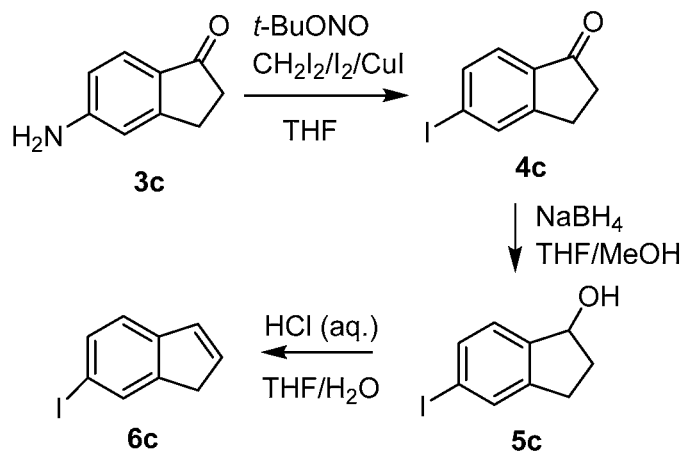
FIG. 27 shows the synthesis of 6-iodoindene 6c.

Subjection of the commercially available 5-aminoindan-1-one 3c to the same sequence of diazotization-iodination followed by the reduction and dehydration yielded 6-iodoindene 6c in 71% overall yield (FIG. 27). This represents a significant improvement to the reported five-step procedure which gave 6c from 3c in 3% overall yield. The method avoids oxidation of 3c to 5-nitroindan-1-one with trifluoroperacetic acid and does not require reduction of 6-nitroindene to unstable 6-aminoindene intermediate.

Figure 28:
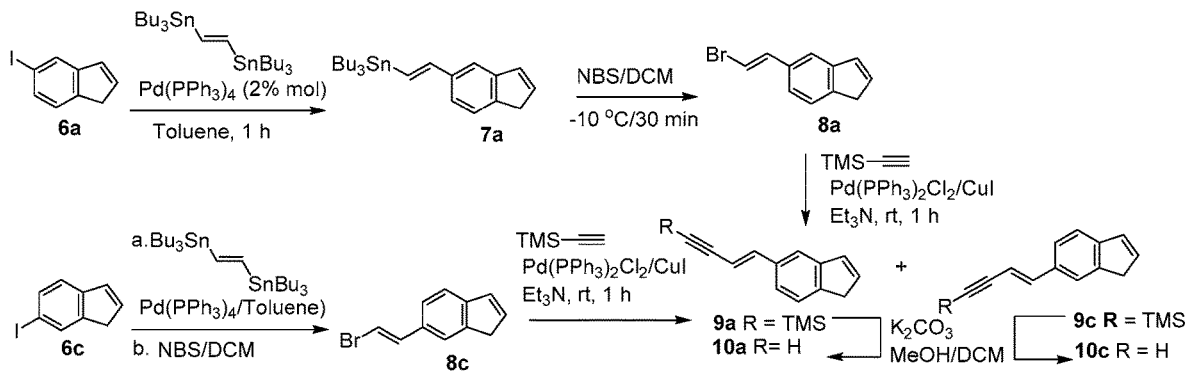
FIG. 28 shows the regioselective bromovinylation of iodoindenes 6a and 6c, and subsequent alkynylation.

Example 3—Application of Iodoindenes to the Pd-catalyzed Stille and Sonogashira Cross-Coupling reactions Iodoindenes were successfully employed in Pd-catalyzed cross-coupling to demonstrate their importance in organic synthesis. Thus, Stille coupling of 6a with trans-1,2-bis (tributylstannyl)ethylene in the presence of catalytic Pd(PPh$_3$)$_4$ in toluene (100° C./1 h) afforded regio- and stereoselectively the E-vinylstannane 7a with no isomerization of the indene five-membered double bond (FIG. 28). Compound 7a was directly used in the next step since attempted purification on silica gel column resulted in protiodestannylation yielding 5-vinylindene instead. Treatment of crude 7a with NBS in DCM (−10° C./30 min) gave 5(E)-(2-bromovinyl)indene 8a (70% from 6a) as a single product.

Similarly, Stille coupling of 6c yielded selectively 6(E)-(2-bromovinyl)indene 8c also with no isomerization that would lead to 8a. Treatment of 8a or 8c with trimethylsilylacetylene in the presence of catalytic Pd(PPh$_3$)$_2$Cl$_2$/CuI in Et$_3$N at rt gave the TMS-protected enyne as an inseparable mixture of 5-enyneindene, 9a and 6-enyneindene, 9c (91%; 1:1.5). Desilylation of mixture 9a and 9c with anhydrous K$_2$CO$_3$ in MeOH/DCM (1:1) afforded a mixture of 5- and 6-enyneindenes 10a and 10c (92%; 1:1.5). The ratio of enynes in mixtures 9a/9c or 10a/10c was assigned based on the chemical shift pattern in $^1$H NMR and differences in the chemical shift values (e.g., H4 in 6a (7.75 ppm) and H7 in 6c (7.81 Ppm)).

Figure 29:
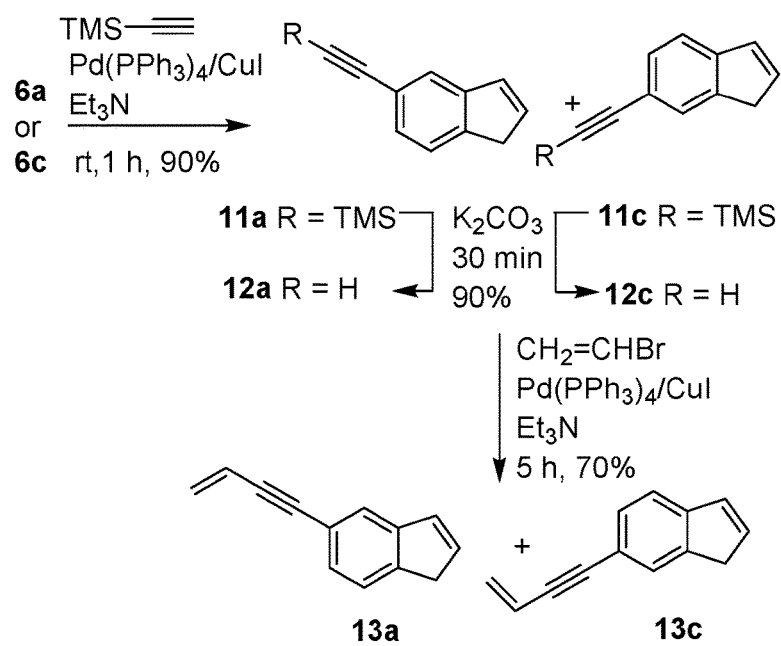
FIG. 29 shows the synthesis of isomeric enyneindenes via Sonogashira coupling.

Sonogashira alkynylation of 6a with trimethylsilylacetylene in the presence of catalytic Pd(PPh$_3$)$_4$/CuI in Et$_3$N produced 5-alkynylindene 11a and 6-alkynylindene 11c as 1:1.5 isomeric mixture in 90% yield (FIG. 29). Analogous treatment of 6c gave an identical mixture of 11a and 11c. Attempted coupling of 6a (or 6c) with TMS-acetylene in the presence of 2.0 equiv. of Et$_3$N in dry THF resulted only in the isomerization of substrate 6a (or 6c) to a 1:1 mixture of 6a/6c. Desilylation of mixture of 11a/11c (1:1.5) with anhydrous K$_2$CO$_3$ in MeOH/DCM yielded mixture of 12a/12c (90%; 1:1.7). Separations of either protected 11a/11c or deprotected 12a/12c enynes on silica gel columns were not successful because of identical mobility in several eluting systems. Pd-catalyzed coupling of 12a/12c mixture (1:1.7) with vinylbromide (CuI/Et$_3$N/rt/5 h) gave mixture of 5-enyne- 13a and 6-enyneindene 13c (70%) in 1:1.5 ratio.

Figure 14A:
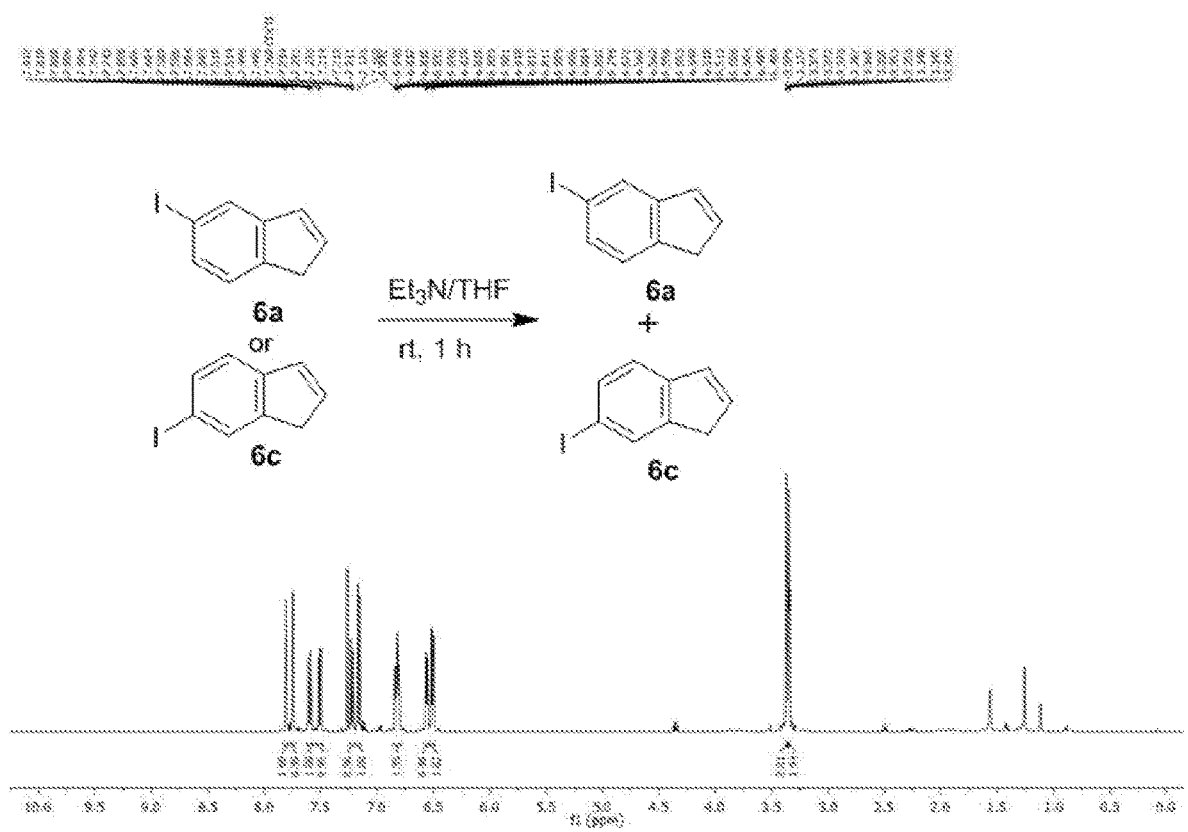
FIGS. 14A-14B show $^1$H NMR and $^{13}$C NMR spectra of the isomerization of single 6a or single 6c into the mixture of 6a+6c in CDCl$_3$.
Figure 14B:
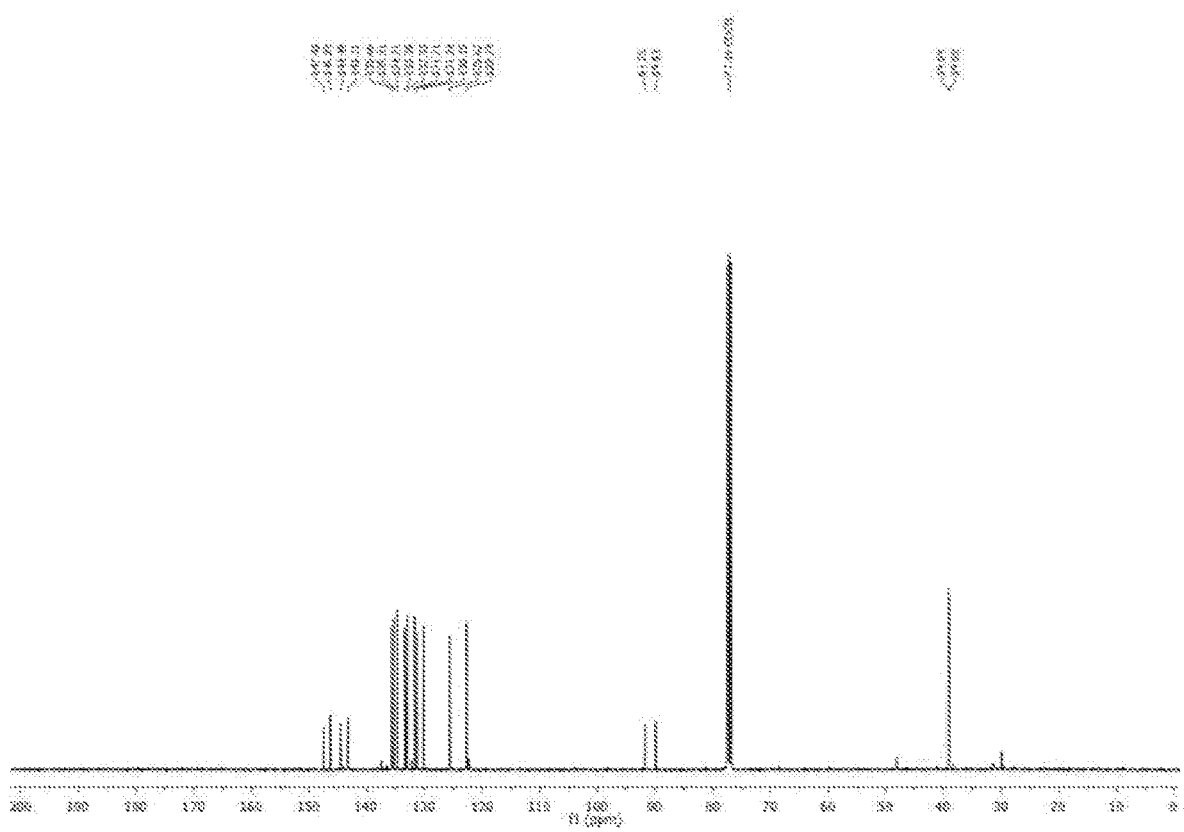

Stirring of pure 6a or 6c in the presence of Et$_3$N in THF at rt for 1 h resulted in the formation of 1:1 isomeric mixture of 6a/6c (FIG. 14) confirming that substituted indenes are prone to base-catalyzed isomerization. Moreover, when 2:1 mixture of 6a/6c was subjected to the similar experiments a 1:1 ratio was also observed at equilibrium. These results demonstrate that the double bond in the five-member ring of the substituted indenes can shift in the presence of base leading to the observed isomers under the conditions of the coupling reactions.

Example 4—General Scheme for the Synthesis of Haloindenes 6 from aminoindan-1-ones 3

The three-step general method for the synthesis of iodoindenes from aminoindan-1-ones 3 can be extended for the preparation of 4-, 5-, 6- or 7-haloindenes 6 by diazotization-halogenation of 3 with BuONO using different halogen sources such as, CuCl$_2$ for chlorination, CHBr$_3$ for bromination, and nitrosonium tetraborofluorate (NOBF$_4$) for fluorination to give haloindan-1-ones 4. Reduction of 4 and dehydration of the resulting iodoindan-1-ols 5 will provide access to variations of all possible mono haloindenes 6 (FIG. 1).

Example 5—Regioselective Synthesis of Indene Derivatives

Figure 30:
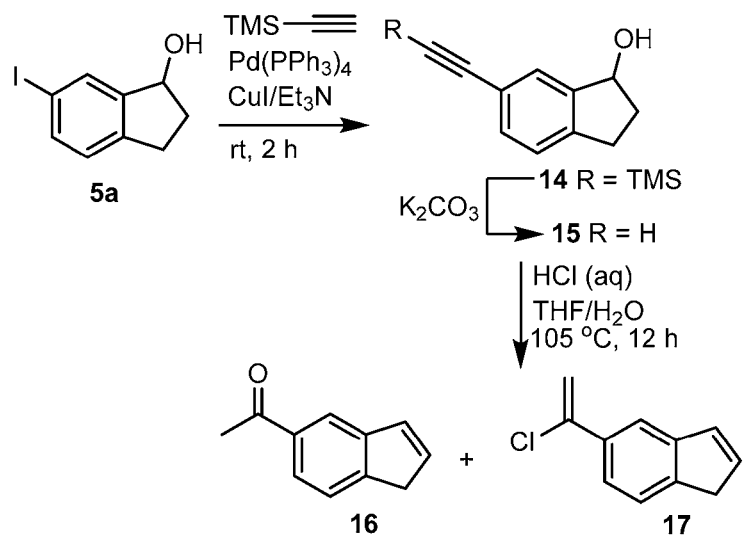
FIG. 30 shows the regioselective synthesis of indene derivatives.

To avoid isomerization of the indene ring during Sonogashira coupling and in order to get regioselective access to indenyl alkynes, synthesis of single 12a from 6-iodoindan-1-ol 5a was attempted. Thus, coupling of 5a with trimethylsilylacetylene provided the trimethylsilylalkyne 14 (90%) as the sole product from which the trimethylsilyl group was removed with K$_2$CO$_3$ to give 6-ethynylindan-1-ol 15. (FIG. 30). Dehydration of either 14 or 15 with aqueous HCl led to the formation of indene products without isomerization of a double bond in cyclopentadiene ring of indene but the simultaneous addition of water or HCl to the triple bond gave acetyl 16 (80%) and 1-chlorovinyl 17 (20%) products.

Figure 31:
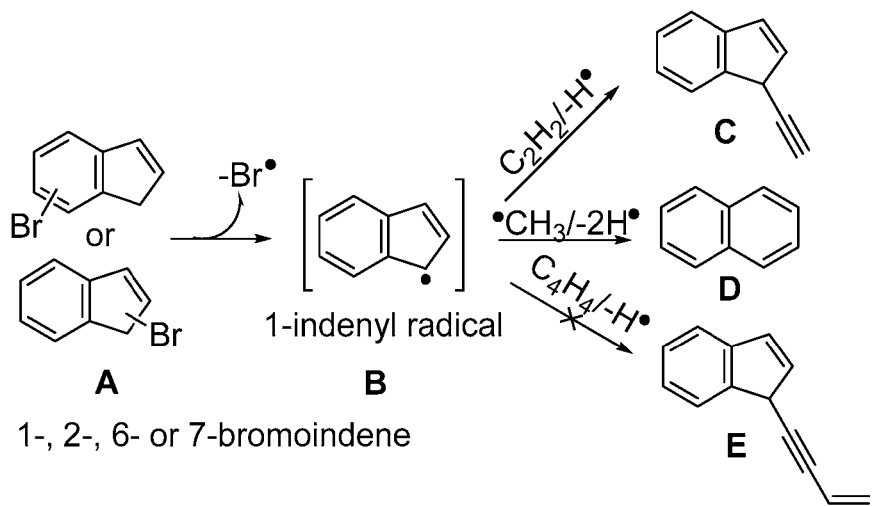
FIG. 31 shows the generation of 1-indenyl π radical from bromoindenes and its further reactions.

Mechanisms of gas phase synthesis and molecular mass growth processes of polycyclic aromatic hydrocarbons (PAH) in extraterrestrial and combustion environments were studied. Pyrolysis of different bromoindenes A at 1500 K produced resonance-stabilized and thermodynamically most stable 1-indenyl π radical B, which was found not to be an effective precursor for the further growth of PAH through the hydrogen abstraction-acetylene (or vinylacetylene) addition (FIG. 31).

The underlying reason for the predominant formation of B from all A appeared to be the fact that the C—Br bond in bromoindenes other than 1-bromoindene is stronger than the C—H bond in the CH$_2$ group in the five-member ring and the mechanism of the formation of B from A was proposed in the previous work. Thus, the radical B reacts with acetylene molecule in gas phase yielding 1-ethynylindene C. Furthermore, reaction between radical B and vinylacetylene exhibits very high reaction barriers for the formation of enyne E or its but-1-en-3-yn-1-yl isomer. However, 1-indenyl radical B reacts with methyl radical to form naphthalene D through the radical-radical reaction, acting, therefore, as effective precursor for growing of planar PAH rings.

Figure 32:
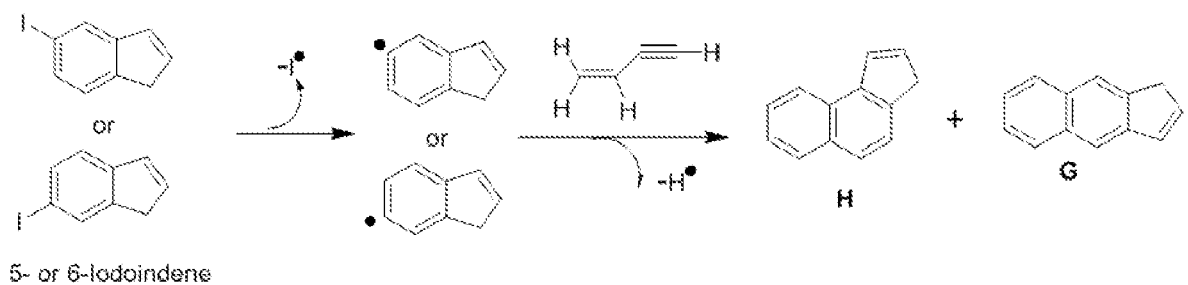
FIG. 32 shows the generation of 5-, or 6-indenyl σ radical from iodoindenes and its further reactions.

Thus, pyrolysis of 5-, or 6-iodoindene isomers can lead to the formation of σ radicals localized in the phenyl ring of indene because C—I bond is weaker than C—Br bond. These 5- and 6-indenyl radicals nay then act as precursors for growth of non-planar PAH molecules, e.g., H and G, containing five-member rings (FIG. 32).

In summary, the subject invention provides an expeditious synthesis of 5, 6, and 7-iodoindenes isomers from the corresponding aminoindan-1-ones utilizing readily available reagents. A three-step sequence involves diazotization-iodination of aminoindan-1-ones followed by the reduction and dehydration. The iodoindenes were regio- and stereoselectively converted to the corresponding (E)-bromovinylindenes utilizing Stille coupling with trans-1,2-bis(tributylstannyl)ethylene followed by bromodestannylation with NBS. Sonogashira coupling of iodoindenes with terminal alkyne in the presence of Et$_3$N gave isomeric ethynylindenes.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

We claim:

1. A method for synthesizing a haloindene comprising:
   mixing a nitrite compound and one or more halogen sources with aminoindan-1-one to produce haloindanone;
   adding a reducing agent to said haloindanone to produce haloindanol; and
   adding an acid to said haloindanol.

2. The method of claim 1, the haloindene being 4-, 5-, 6-, or 7-chloroindene, bromoindene, fluoroinfene or iodoindene.

3. The method of claim 1, the one or more halogen sources being selected from I$_2$, CuI, CuCl$_2$, CH$_2$I$_2$, CHBr$_3$, NOBF$_4$, KX and HX; and X=Cl, F, Br, or I.

4. The method of claim 1, the reducing agent being NaBH$_4$.

5. The method of claim 1, the acid being HCl.

6. The method of claim 1, the nitrite compound being t-BuONO.

7. A method for synthesizing an iodoindene comprising:

mixing a nitrite compound and one or more iodine sources with aminoindan-1-one to produce iodoindanone;

adding a reducing agent to said iodoindanone to produce iodoindanol; and adding an acid to said iodoindanol.

8. The method of claim 7, the iodoindene being 4-, 5-, 6-, or 7-iodoindene.

9. The method of claim 7, the one or more iodine sources being selected from $I_2$, CuI, $CH_2I_2$, KI and HI.

10. The method of claim 7, the reducing agent being $NaBH_4$.

11. The method of claim 7, the acid being HCl.

12. The method of claim 7, the nitrite compound being t-BuONO.

13. The method of claim 7, aminoindan-1-one being selected from 4-, 5-, 6-, and 7-aminoindan-1-one.

14. The method of claim 7, which has a yield of at least 70%.

15. The method of claim 7, the method consisting of:

mixing a nitrite compound and one or more iodine sources with aminoindan-1-one to produce iodoindanone;

adding a reducing agent to said iodoindanone to produce iodoindanol; and adding an acid to said iodoindanol.

16. A composition comprising 4-iodoindene or 7-iodoindene in solid or powder form or in a solvent, carrier, vehicle and/or excipient.

* * * * *